US010407462B2

(12) United States Patent
Zampella et al.

(10) Patent No.: US 10,407,462 B2
(45) Date of Patent: Sep. 10, 2019

(54) CHOLANE DERIVATIVES FOR USE IN THE TREATMENT AND/OR PREVENTION OF FXR AND TGR5/GPBAR1 MEDIATED DISEASES

(71) Applicant: BAR PHARMACEUTICALS S.R.L., Reggio Emilia (IT)

(72) Inventors: Angela Zampella, Naples (IT); Stefano Fiorucci, Perugia (IT)

(73) Assignee: BAR PHARMACEUTICALS S.R.L., Reggio Emilia (IT)

(*) Notice: Subject to any disclaimer, the term of this patent is extended or adjusted under 35 U.S.C. 154(b) by 89 days.

(21) Appl. No.: 15/314,771

(22) PCT Filed: May 28, 2015

(86) PCT No.: PCT/EP2015/061802
§ 371 (c)(1),
(2) Date: Nov. 29, 2016

(87) PCT Pub. No.: WO2015/181275
PCT Pub. Date: Dec. 3, 2015

(65) Prior Publication Data

US 2017/0190731 A1 Jul. 6, 2017

(30) Foreign Application Priority Data

May 29, 2014 (IT) ................................ FI2014A0130

(51) Int. Cl.

| | |
|---|---|
| ***C07J 31/00*** | (2006.01) |
| ***C07J 9/00*** | (2006.01) |
| ***C07J 41/00*** | (2006.01) |
| ***C07J 11/00*** | (2006.01) |

(52) U.S. Cl.
CPC ............... *C07J 31/006* (2013.01); *C07J 9/00* (2013.01); *C07J 9/005* (2013.01); *C07J 11/00* (2013.01); *C07J 41/0094* (2013.01)

(58) Field of Classification Search
CPC ...... C07J 31/006; C07J 9/005; C07J 41/0094; C07J 11/00
See application file for complete search history.

(56) References Cited

U.S. PATENT DOCUMENTS

| | | | | |
|---|---|---|---|---|
| 7,138,390 B2* | 11/2006 | Pellicciari | C07J 9/00 | 514/182 |
| 7,812,011 B2* | 10/2010 | Pellicciari | C07J 9/005 | 514/182 |
| 7,932,244 B2* | 4/2011 | Pellicciari | C07J 9/00 | 514/182 |
| 7,994,352 B2* | 8/2011 | Ferrari | C07J 9/005 | 552/551 |
| 8,410,083 B2* | 4/2013 | Pellicciari | C07J 9/005 | 514/182 |
| 8,546,365 B2* | 10/2013 | Pellicciari | C07J 9/00 | 514/182 |
| 8,796,249 B2* | 8/2014 | Pellicciari | C07J 31/006 | 514/182 |
| 9,090,652 B2* | 7/2015 | Pellicciari | C07J 9/00 | |
| 9,498,484 B2* | 11/2016 | Fiorucci | A61K 31/575 | |
| 9,763,964 B2* | 9/2017 | Pellicciari | C07J 9/00 | |
| 9,777,038 B2* | 10/2017 | Pellicciari | C07J 9/00 | |
| 2008/0119443 A1 | 5/2008 | Li et al. | | |
| 2011/0003782 A1* | 1/2011 | Pellicciari | C07J 9/005 | 514/182 |
| 2011/0263555 A1* | 10/2011 | Pellicciari | C07J 9/005 | 514/182 |
| 2013/0261317 A1* | 10/2013 | Moriarty | A61K 45/06 | 549/334 |
| 2014/0206657 A1* | 7/2014 | Yu | C07J 9/005 | 514/177 |
| 2014/0371190 A1* | 12/2014 | Pellicciari | C07J 9/005 | 514/182 |

(Continued)

FOREIGN PATENT DOCUMENTS

| | | | |
|---|---|---|---|
| CA | 2440680 A1 * | 9/2002 | C07J 9/00 |
| CA | 2948585 A1 * | 12/2015 | C07J 9/00 |
| CN | 103143021 A * | 6/2013 | |

(Continued)

OTHER PUBLICATIONS

Schaik et al. PLoS ONE 7(11):e49706 (2012) (Year: 2012).*
Lian et al. Rheumatol. Int. 32: 1705-1710 (2012). (Year: 2012).*
Iguchi et al. Steroids 75 (2010) 95-100. (Year: 2010).*
Pellicciari et al. ACS Medicinal Letters 3(4) 273-277 (2012) (Year: 2012).*
Monte et al. World J. Gastroenterology 15(7): 804-816 (2009) (Year: 2009).*
D'Amore, Claudio, et al., Design, Synthesis, and Biological Evaluation of Potent Dual Agonists of Nuclear and Membrane Bile Acide Receptors, Journal of Medicinal Chemistry, 57(3):937-954, Feb. 13, 2014.

(Continued)

*Primary Examiner* — Nyeemah A Grazier
(74) *Attorney, Agent, or Firm* — McCarter & English, LLP; David R. Burns; Wei Song

(57) ABSTRACT

The present invention relates to compounds having cholane scaffolds of formula (I), said compounds for use in the treatment and/or prevention of FXR and TGR5/GPBAR1 mediated diseases.

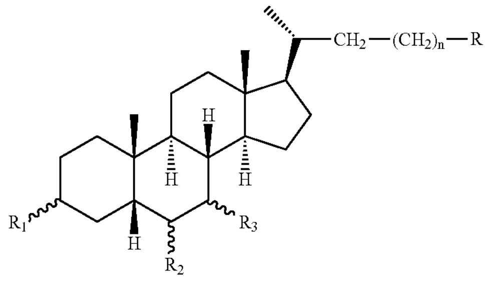

11 Claims, No Drawings

(56) References Cited

U.S. PATENT DOCUMENTS

| | | | | |
|---|---|---|---|---|
| 2017/0196890 | A1* | 7/2017 | Yu | C07J 9/005 |
| 2017/0233431 | A1* | 8/2017 | Yu | C07J 9/005<br>514/182 |

FOREIGN PATENT DOCUMENTS

| | | | | | |
|---|---|---|---|---|---|
| EP | 1568706 | A1 | * | 8/2005 | C07J 9/005 |
| EP | 1947108 | A1 | * | 7/2008 | C07J 9/005 |
| FR | 2908310 | A1 | * | 5/2008 | A61K 31/19 |
| WO | WO-2008091540 | A2 | * | 7/2008 | C07J 9/005 |
| WO | WO-2010059853 | A1 | * | 5/2010 | C07J 9/00 |
| WO | WO-2010059859 | A1 | * | 5/2010 | C07J 9/005 |
| WO | WO-2013192097 | A1 | * | 12/2013 | A61K 9/2054 |
| WO | WO-2015017813 | A2 | * | 2/2015 | C07J 9/005 |
| WO | WO-2015183794 | A1 | * | 12/2015 | C07J 9/005 |

OTHER PUBLICATIONS

Festa, Carmen, et al., Exploitation of Cholane Scaffold for the Discovery of Potent and Selective Famesoid X Receptor (FXR) and G-Protein Coupled Bile Acid Receptor 1 (GP-BAR1) Ligands, Journal of Medicinal Chemistry, 57 (20):8477-8495, Oct. 23, 2014.

Fujino, T., et al., Structure-activity relationship of bile acids and bile acid analogs in regard to FXR activation, Journal of Lipid Research, 45(1):132-138, Jan. 1, 2004.

Fukuchi, J., et al., 5beta-Cholane activators of the farnesol X receptor, Journal of Steroid Biochemistry and Molecular Biology, Elsevier Science Ltd., Oxford, GB, 94(4):311-318, Mar. 1, 2005.

Hsieh, H-P, et al., Synthesis and DNA Binding Properties of C3-, C12-, AND C24- Substituted Amino-Steroids Derived from Bile Acids, Bioorganic & Medicinal Chemistry, Pergamon, GB, 3(6):823-838, Jun. 1, 1995.

Iguchi, Y., et al., Bile alcohols function as the ligands of membrane-type bile acid-activated G protein-coupled receptor, The Journal of Lipid Research, 51(6):1432-1441, Dec. 18, 2009.

Pellicciari, R., et al., 6alpha-Ethyl-Chenodeoxycholic Acid (6-ECDCA), a potent and selective FXR agonist endowed with anticholestatic activity, Journal of Medicinal Chemistry, American Chemical Society, US, 45 (17):3569-3572, Jan. 1, 2002.

Sato, Hiroyuki, et al., Novel potent and selective bile acid derivatives as TGR5 agonists: biological screening, structure-activity relationships, and molecular modeling studies, Journal of Medicinal Chemistry, American Chemical Society, US, 51(6):1831-1841, Mar. 27, 2008.

Sepe, Valentina, et al., Modification on Ursodeoxycholic Acid (UDCA) Scaffold, Discovery of Bile Acid Derivatives as Selective Agonists of Cell-Surface G-Protein Coupled Bile Acid Receptor 1 (GP-BAR1), Journal of Medicinal Chemistry, 57(18):7687-7701, Sep. 25, 2014.

* cited by examiner

CHOLANE DERIVATIVES FOR USE IN THE TREATMENT AND/OR PREVENTION OF FXR AND TGR5/GPBAR1 MEDIATED DISEASES

CROSS-REFERENCE TO RELATED APPLICATIONS

This application is a U.S. national stage application filed under 35 U.S.C. § 371(c), of International Application No. PCT/EP2015/061802, filed on May 28, 2015, which claims foreign priority to Italian Patent Application No. FI2014A00130, filed on May 29, 2014. The entire contents of each of the aforementioned applications are incorporated herein by reference.

FIELD OF THE INVENTION

The present invention relates to compounds having cholane scaffolds, said compounds for use in the treatment and/or prevention of FXR and TGR5/GPBAR1 mediated diseases.

STATE OF THE ART

Bile acids (BAs) are signaling molecules interacting with two type of dedicated cellular receptors, intracellular nuclear receptors and cell-surface receptors. Nuclear receptors include farnesoid X receptor (FXR), identified as the endogenous bile acid sensor (Makishima et al *Science* 1999, 284, 1362; Parks et al. Science 1999, 284, 1365).

Highly expressed in entero-hepatic tissues (liver and intestine), FXR regulates bile acid homeostasis, metabolic pathways also including lipid and glucose homeostasis (Zhang et al. Proc. *Natl.* Acad. Sci. USA 2006, 103, 1006). Additionally FXR agonists provides anti-inflammatory and anti-fibrotic and anticancer effects (Renga et al. FASEB J=2012, 26, 3021-3031).

Bile acid cell-surface receptor (GPBAR1, M-BAR1, GP-BAR1, TGR5) belongs to the rhodopsin-like superfamily of G protein coupled receptors (Takeda et al. FEBS Lett. 2002, 520, 97; Kawamata et al. J. Biol. Chem. 2003, 278, 9435).

Ligand binding to TGR5/GPBAR1 results in elevation of intracellular cAMP levels with consequently activation of a signaling cascade. GPBAR1 is highly expressed in the liver and in the intestine but also muscles, brain, adipose tissue, macrophages and endothelial cells. In muscle and brown adipose tissue, TGR5/GPBAR1 increases energy expenditure and oxygen consumption (Watanabe et al. Nature 2006, 439, 484) in entero-endocrine L cells, TGR5/GPBAR1 activation stimulates the secretion of glucagon-like peptide (GLP)-1, an incretin that improves pancreas insulin release, thus regulating glucose blood levels, gastrointestinal motility and appetite (Thomas, et al. Cell. Metab. 2009, 10, 167).

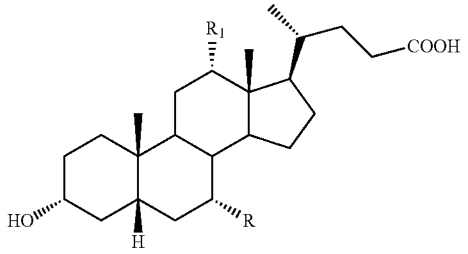

| | | |
|---|---|---|
| R = OH | R1 = H | CDCA |
| R = OH | R1 = OH | CA |
| R = H | R1 = OH | DCA |
| R = H | R1 = H | LCA |

-continued

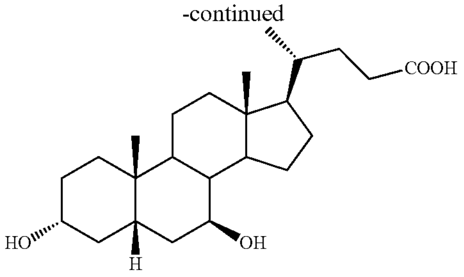

UDCA

Chemically BAs are truncated cholesterol side chain derivatives. Their molecular repertoire is generated firstly in the liver with the production of primary bile acids, cholic acid (CA) and chenodeoxycholic acid (CDCA). Microbiotransformation in the intestine generates secondary bile acids, deoxycholic acid (DCA) and lithocholic acid (LCA), In human body bile acids are conjugated to glycine and taurine. The activity towards the two BA receptors is structure dependent with CDCA the most potent endogenous FXR activator, and LCA and TLCA the strongest natural agonists of TGR5/GPBAR1.

Cholestatic pruritus has been noted as a severe side-effect associated with the use of FXR agonists in PBC and a recent study indicated TGR5/GPBAR1 as the molecular target involved in the development of this side effect (Alemi et al. J. Clin. Invest. 2013, 123, 1513-1530).

WO2013192097 describes 6-alpha-ethyl-chenodeoxycholic acid (6-ECDCA), a potent and selective FXR agonist endowed with anticholestatic effect.

WO2008002573 describes bile acid derivatives as FXR ligands for the prevention or treatment of FXR-mediated diseases or conditions.

WO2010014836 and Sato H. (J Med Chem. 2008, 51, 4849) describes TGR5 modulators.

D'Amore C. et al. (J. Med. Chem. 2014, 57, 937) describes Design, synthesis, and biological evaluation of GP-BAR1/FXR dual agonists. D'Amore et al. describes compounds BAR502 and BAR504 as synthesis intermediates.

Iguchi Y. et al. (J Lipid Res. 2010, 51, 1432) describes bile alcohols function as the ligands of TGR5.

Compounds BAR107 is disclosed as synthesis intermediate by Kihira K. et al. (Steroids 1992, 57(4), 193-198).

Swaan P. W. et al. (J. Comp.-Aid. Mol. Des. 1997, 11, 581-588) in a molecular modeling of the intestinal bile acid carrier tested ursocholate (therein compound 15, herein BARn406) among a set of bile acid-conjugates. BARn406 resulted to have an undetectable ability to inhibit taurocholic acid transport in CaCo-2 cells.

Burns et al. (Steroids 2011, 76(3), 291-300) describes synthesis and olfactory activity of unnatural, sulfated 5-bile acid derivatives in the sea lamprey (*Petromyzon marinus*). Therein disclosed compound 9e (herein compound BAR407) did not to elicit an olfactory response.

Aim of the present invention is the identification of novel compounds containing the cholane chemical scaffold and that modulate FXR and/or TGR5/GPBAR1.

SUMMARY OF THE INVENTION

Subject-matter of the present invention is a compound of formula (I)

(I)

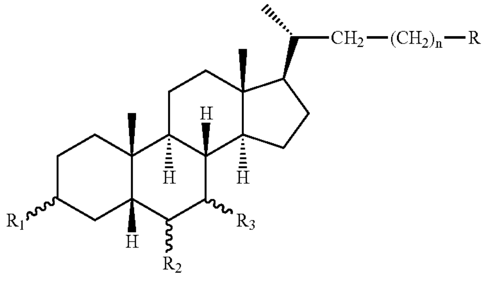

wherein $R_1$ is OH or H;

$R_2$ is Et, $=CH-CH_3$ or H;

$R_3$ is OH or H;

n is 0, 1, or 3;

R is $CH_2OH$, COOH, $CH_2OSO_3H$ or CN;

proviso that when $R_2$ is Et or $=CH-CH_3$ and $R_3$ is OH:

if n is 0 or 1 then R is $CH_2OH$ or CN when $R_1$ is alpha-OH or R is COOH, $CH_2OH$ or $CH_2OSO_3H$ when $R_1$ is beta-OH or H;

if n is 3 then $R_1$ and R are as defined above;

when $R_2$ is H:

if $R_1$ is alpha-OH and $R_3$ is beta-OH then R is $CH_2OH$ or $CH_2OSO_3H$ when n is 0 or R is $CH_2OH$ or COOH when n is 3;

if $R_1$ is H, n is 1 and $R_3$ is alpha-OH then R is $CH_2OSO_3H$;

if $R_1$ and $R_3$ are H then R is $CH_2OSO_3H$ or COOH when n is 0 or R is $CH_2OSO_3H$ when n is 1;

including inorganic and organic pharmaceutically acceptable salts, solvates and amino acid conjugates thereof;

excluding a compound wherein

| Compound ID | n | $R_1$ | $R_2$ | $R_3$ | R |
|---|---|---|---|---|---|
| BAR107 | 0 | alpha-OH | H | beta-OH | CH2OH |
| BARn406 | 0 | H | H | H | COOH |
| BAR504 | 1 | alpha-OH | alpha-Et | alpha-OH | CH2OH |
| BAR407 | 1 | H | H | H | CH2OSO3H |
| BAR502 | 0 | alpha-OH | alpha-Et | alpha-OH | CH2OH |

Compounds as above described have been found to be FXR or/and TGR5/GPBAR1 modulators and are therefore useful for the treatment of FXR and TGR5/GPBAR1 mediated diseases.

Therefore for an aspect the present invention relates to a compound for use as medicament, said compound of formula (I)

wherein $R_1$ is OH or H;

$R_2$ is Et, $=CH-CH_3$ or H;

$R_3$ is OH or H;

n is 0, 1, or 3;

R is $CH_2OH$, COOH, $CH_2OSO_3H$ or CN proviso that when $R_2$ is Et or $=CH-CH_3$ and $R_3$ is OH:

if n is 0 or 1 then R is $CH_2OH$ or CN when $R_1$ is alpha-OH or R is COOH, $CH_2OH$ or $CH_2OSO_3H$ when $R_1$ is beta-OH or H;

if n is 3 then $R_1$ and R are as defined above;

when $R_2$ is H:

if $R_1$ is alpha-OH and $R_3$ is beta-OH then R is $CH_2OH$ or $CH_2OSO_3H$ when n is 0 or R is $CH_2OH$ or COOH when n is 3;

if $R_1$ is H, n is 1 and $R_3$ is alpha-OH then R is $CH_2OSO_3H$;

if $R_1$ and $R_3$ are H then R is $CH_2OSO_3H$ or COOH when n is 0 or R is $CH_2OSO_3H$ when n is 1;

including inorganic and organic pharmaceutically acceptable salts, solvates and amino acid conjugates thereof.

For a further aspect the present invention relates to a compound of formula (I) as above described, including compounds BAR107, BARn406, BAR504, BAR407 and BAR502, for use in the prevention and/or treatment of gastrointestinal disorders, liver diseases, cardiovascular diseases, atherosclerosis, metabolic diseases, infectious diseases, cancer, renal disorders, inflammatory disorders, and neurological disorders (such as stroke), said compound of formula (I) as above described.

The present invention also relates to a process for preparing a compound as above described.

DETAILED DESCRIPTION OF THE INVENTION

According to the invention are preferred those compounds wherein $R_2$ is Et or $=CH-CH_3$ and $R_3$ is OH; more preferably those compounds wherein n is 0 or 1, R is $CH_2OH$ or CN and $R_1$ is alpha-OH or n is 0 or 1, R is COOH, $CH_2OH$ or $CH_2OSO_3H$ and $R_1$ is beta-OH or H.

When $R_2$ is Et or $=CH-CH_3$ and $R_3$ is OH preferred is a compound selected in the group consisting of

BAR501

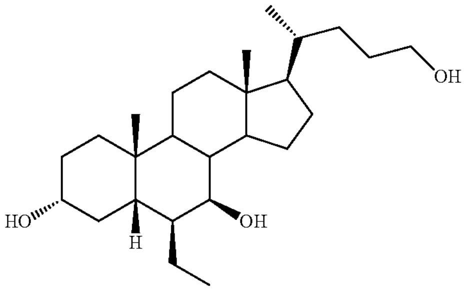

BARn501

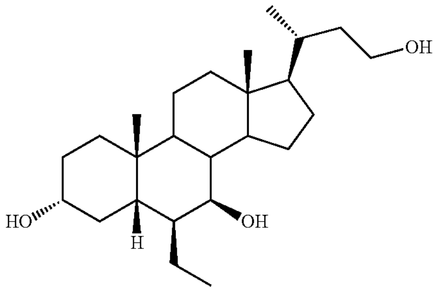

-continued
BAR501-6a
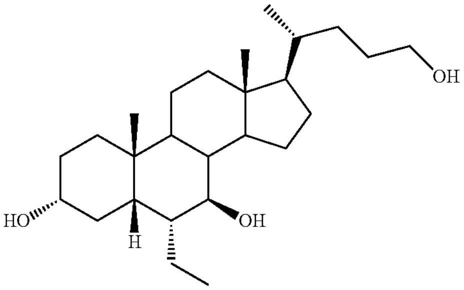
BAR502
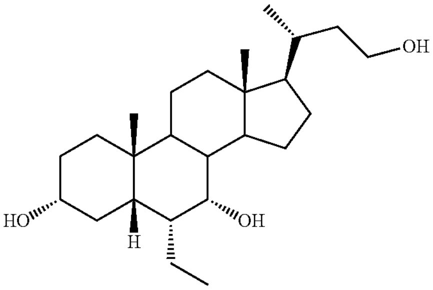
BAR503
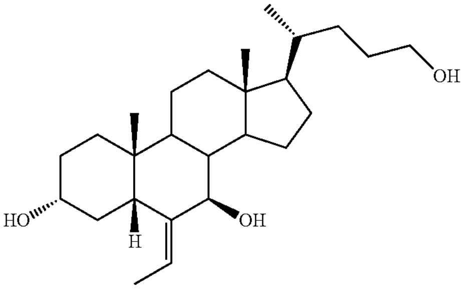
BAR504
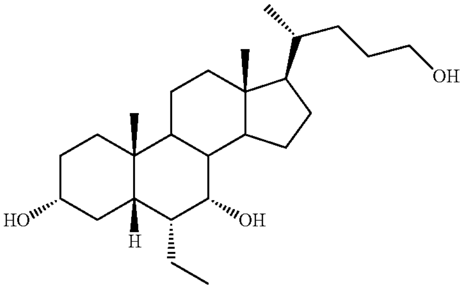
BAR504-6b
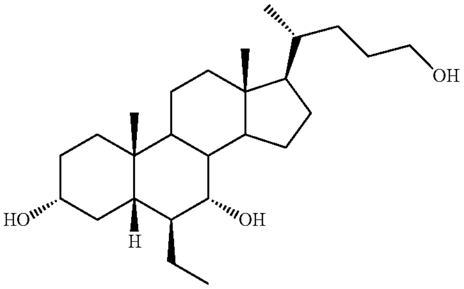
-continued
BAR506
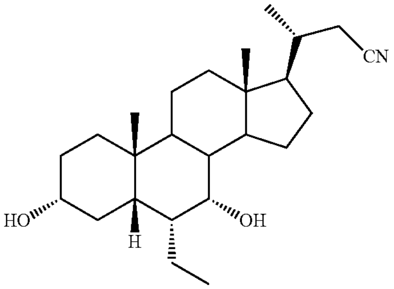
BAR701
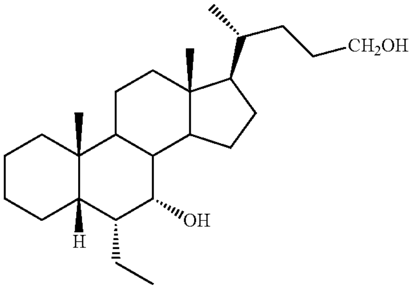
BAR701solf
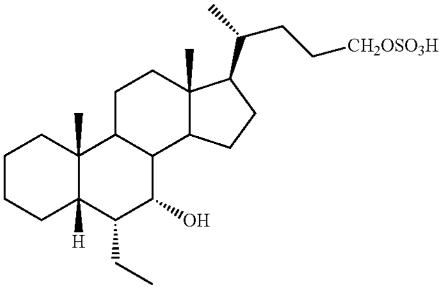
BARn701
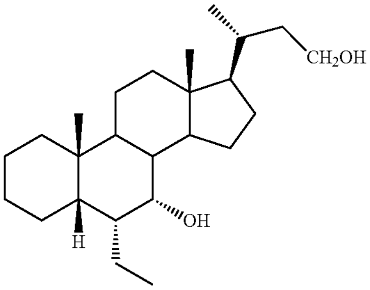
BAR702
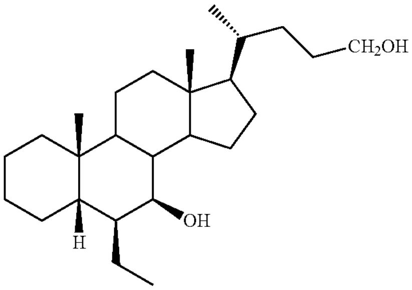

-continued
BAR703
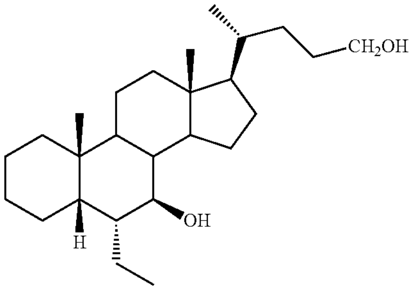
BAR704
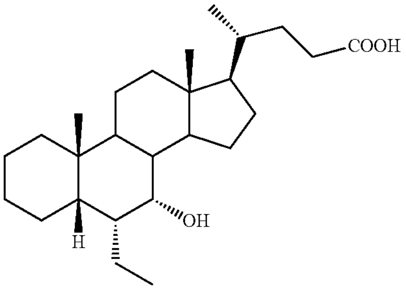
BARn704
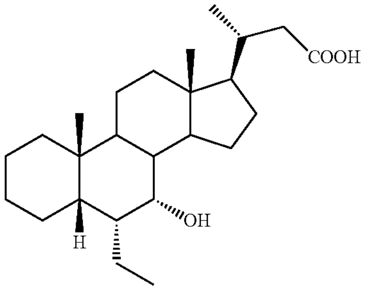
BAR705
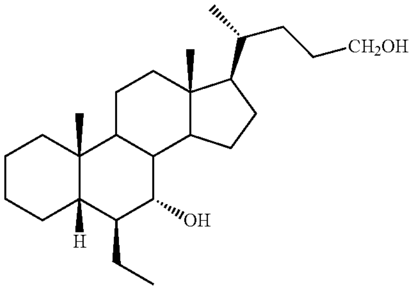
BAR706
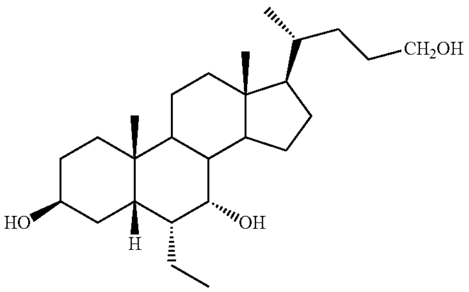
-continued
BARn706
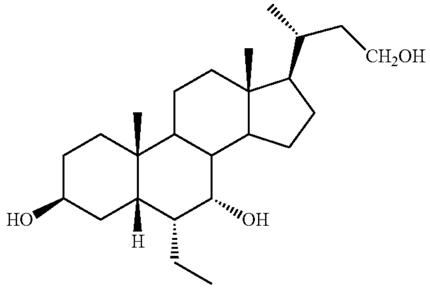
BARn706solf
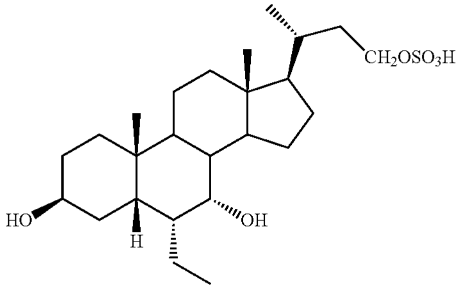
BAR707
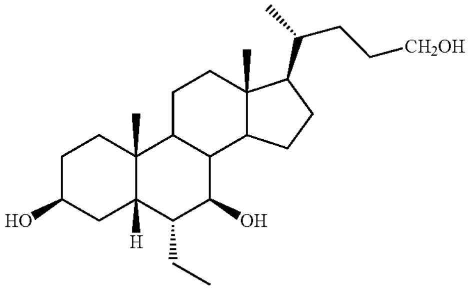
BAR708
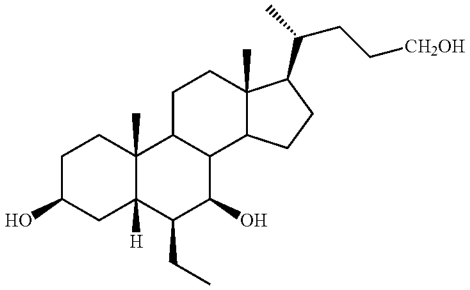
BAR709
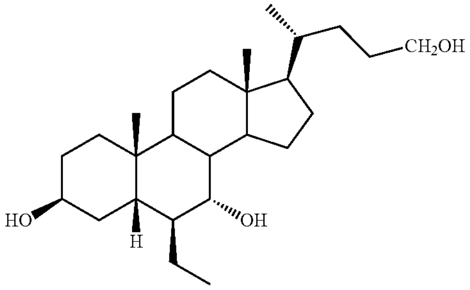

-continued

BAR710

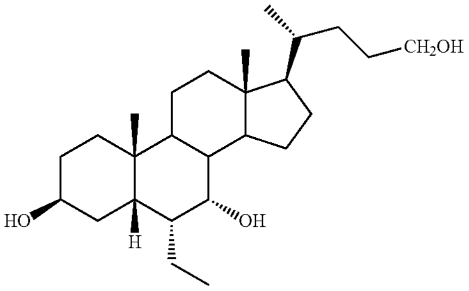

BARn710

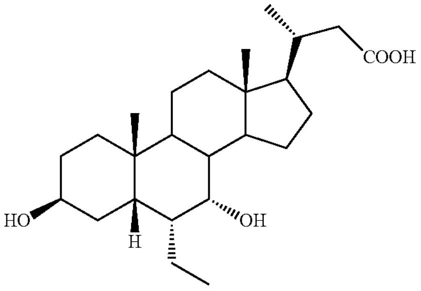

BAR712

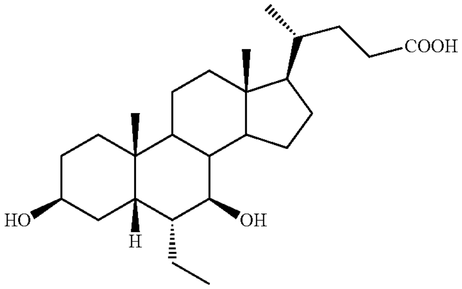

According to the invention are preferred also those compounds wherein $R_2$ is Et or =CH—$CH_3$, $R_3$ is OH, n is 3 and $R_1$ and R are as defined above; more preferred are those compound wherein $R_2$ is Et, $R_3$ is alpha-OH, n is 3 and $R_1$ is alpha-OH and R is as defined above.

Preferred is a compound selected in the group consisting of

BAR802

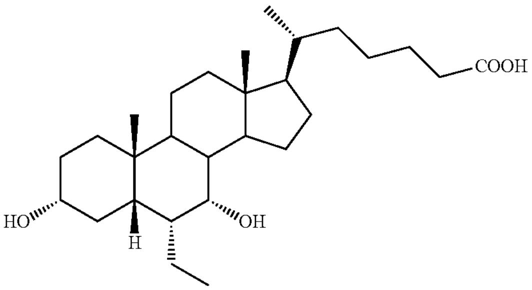

-continued

BAR803

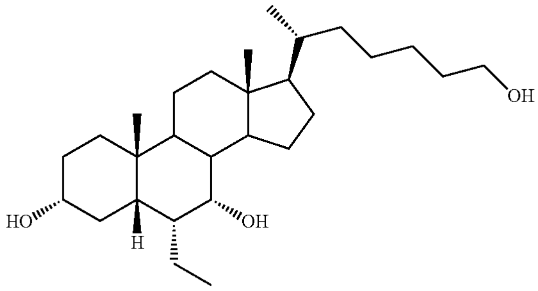

BAR804

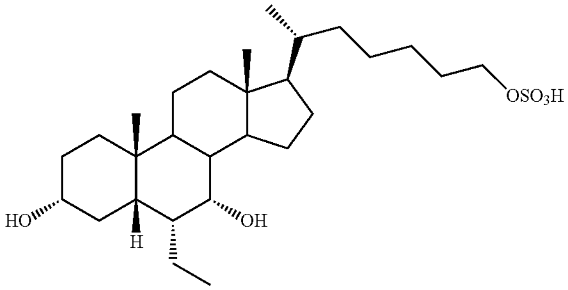

According to the invention are also preferred those compounds wherein $R_2$ is H and if $R_1$ is alpha-OH and $R_3$ is beta-OH then R is $CH_2OH$ or $CH_2OSO_3H$ when n is 0 or R is $CH_2OH$ or COOH when n is 3;

if $R_1$ is H, n is 1 and $R_3$ is alpha-OH then R is $CH_2OSO_3H$;

if $R_1$ and $R_3$ are H then R is $CH_2OSO_3H$ or COOH when n is 0 or R is $CH_2OSO_3H$ when n is 1;

among these is preferred a compound selected in the group consisting of

BAR106

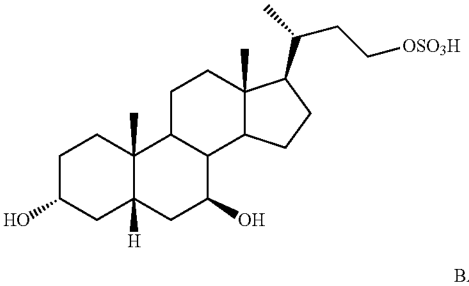

BAR107

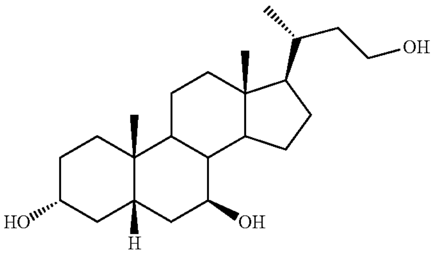

-continued
BAR304
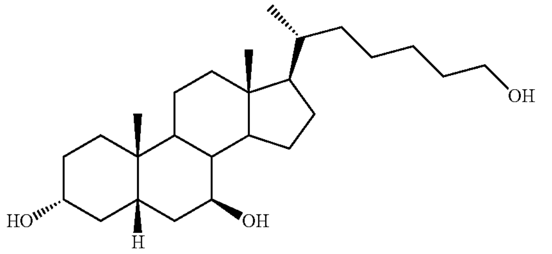
BAR305
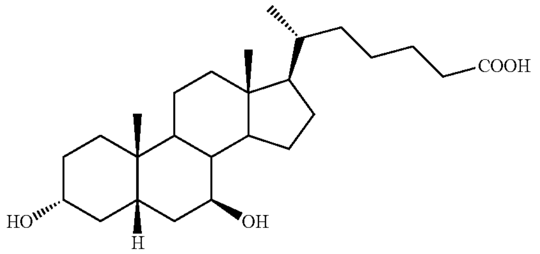
BAR402
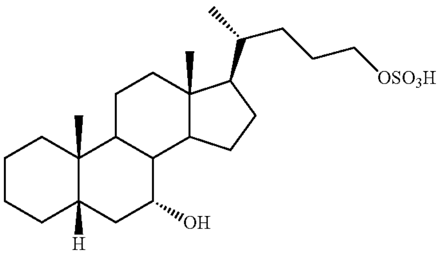
BARn406
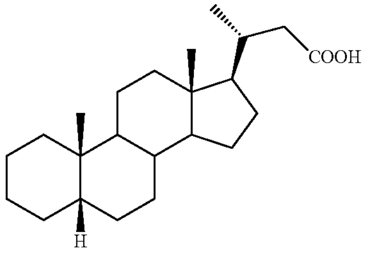
BAR407
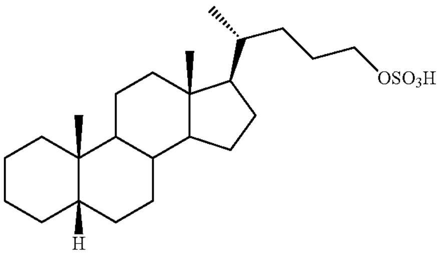
Particularly preferred is a compound according to the invention which is selected in the group consisting of:
BAR106
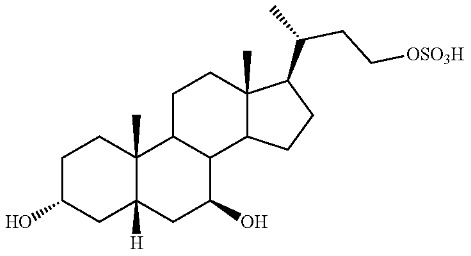
BAR107
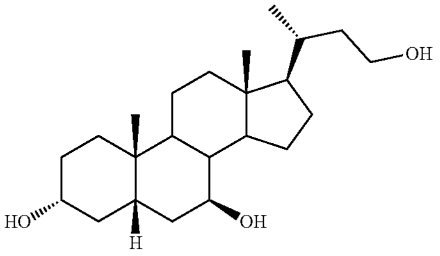
BAR304
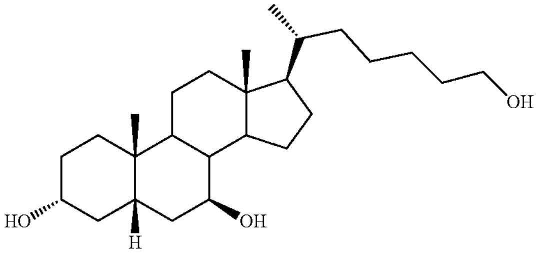
BAR305
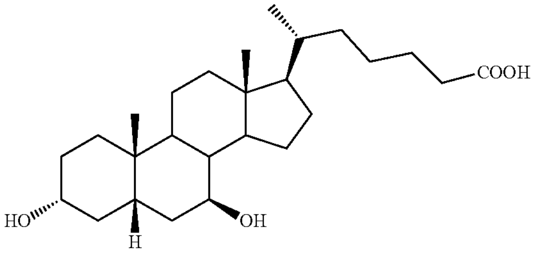
BAR402
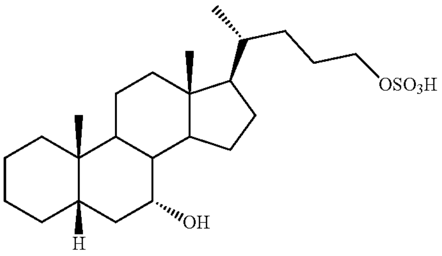
BARn406
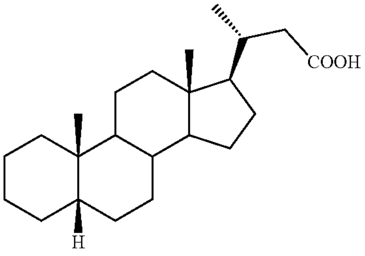

-continued
BAR407
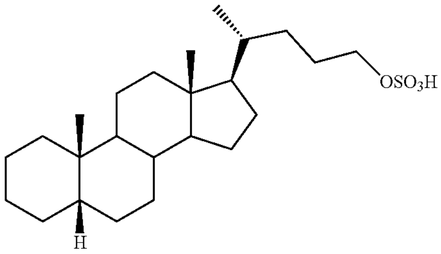
BAR501
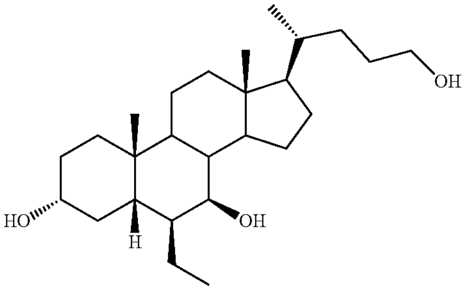
BARn501
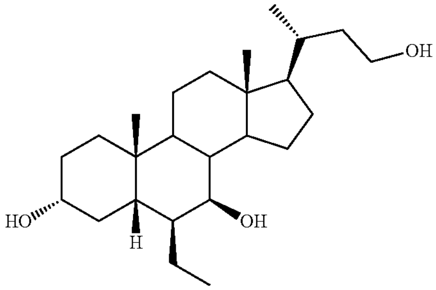
BAR501-6a
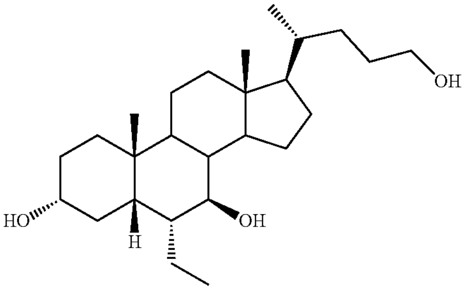
BAR502
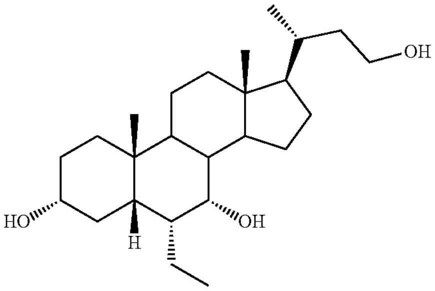
-continued
BAR503
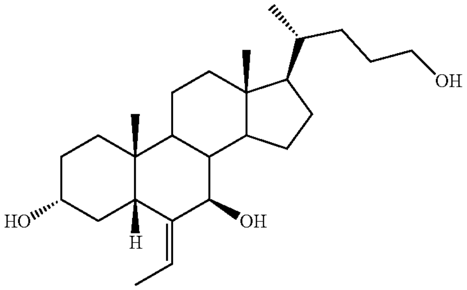
BAR504
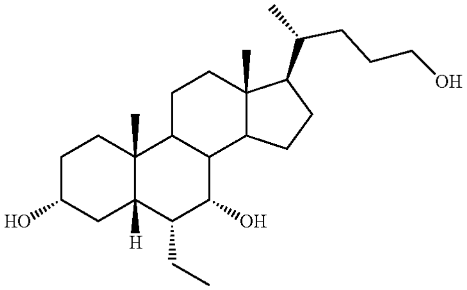
BAR504-6b
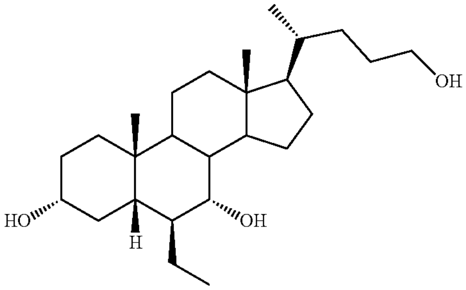
BAR506
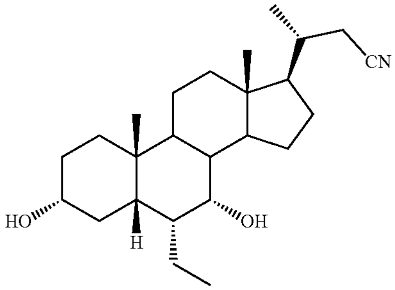
BAR701
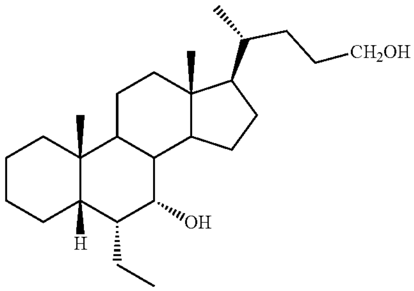

-continued
BAR701solf
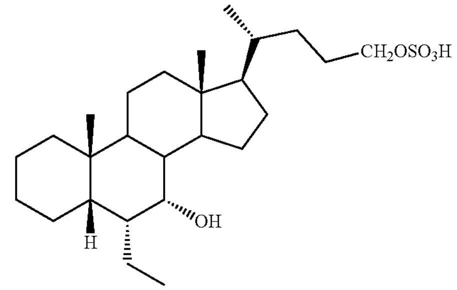
BARn701
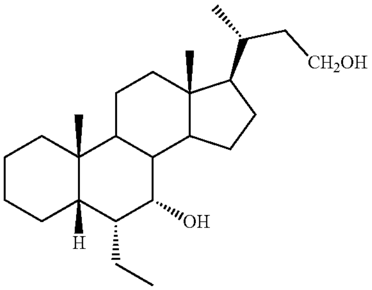
BAR702
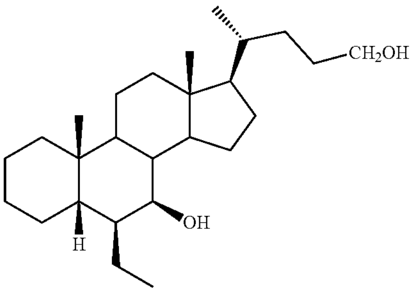
BAR703
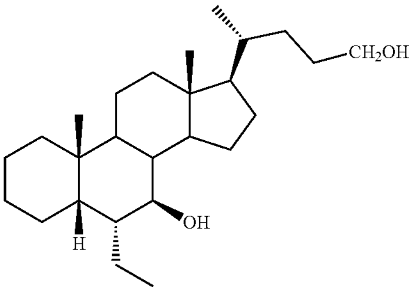
BAR704
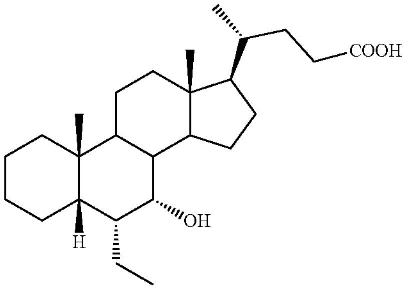
-continued
BARn704
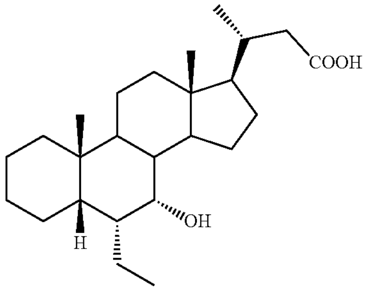
BAR705
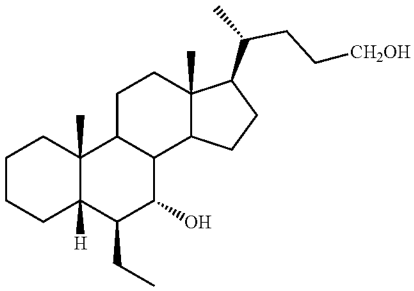
BAR706
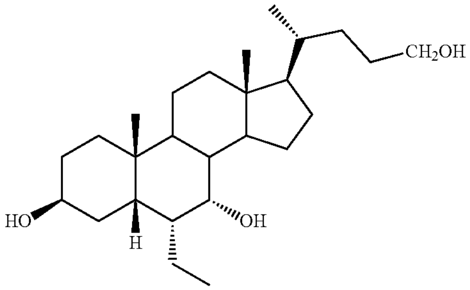
BARn706
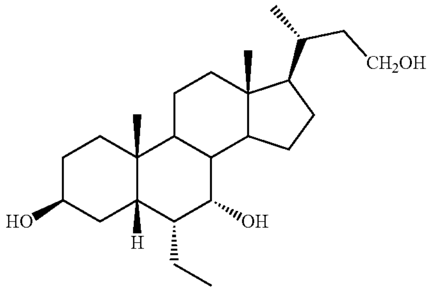
BARn706solf
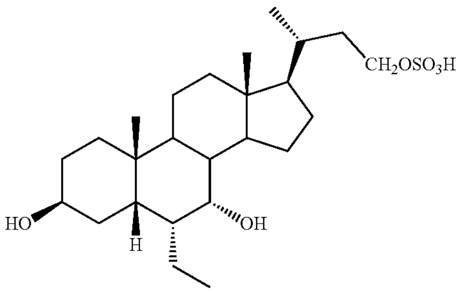

-continued
BAR707
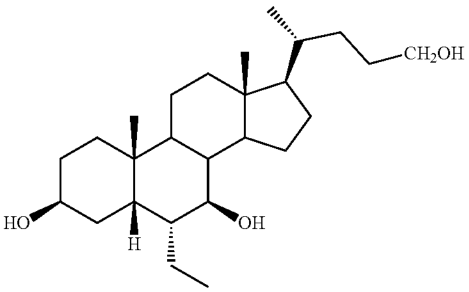
BAR708
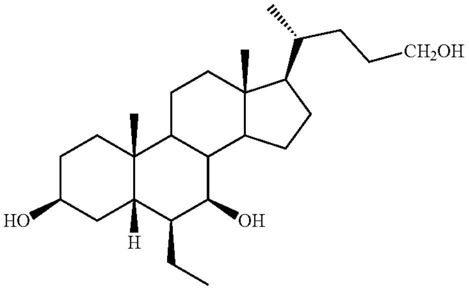
BAR709
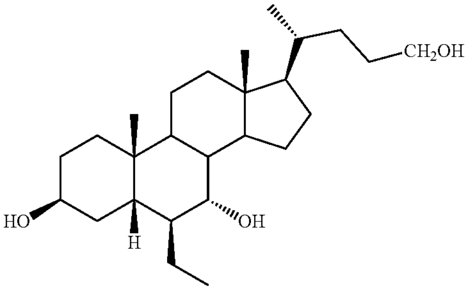
BAR710
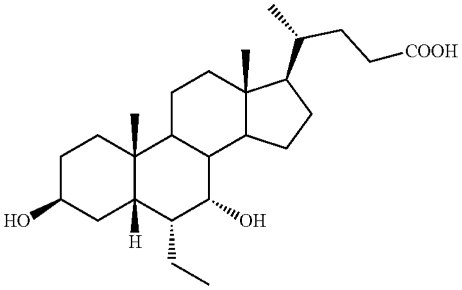
BARn710
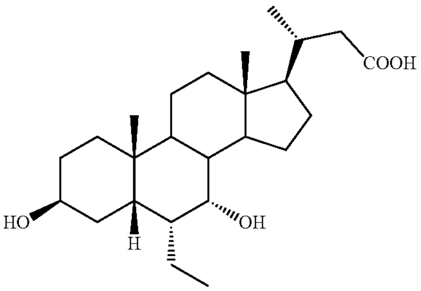
-continued
BAR711
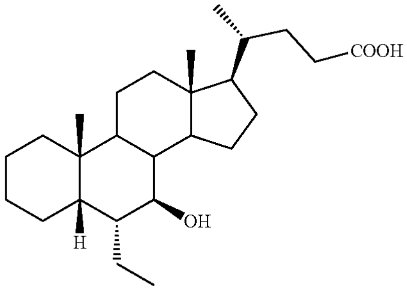
BAR712
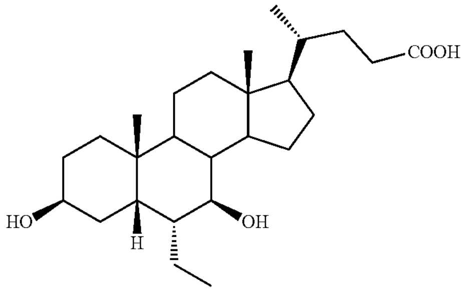
BAR802
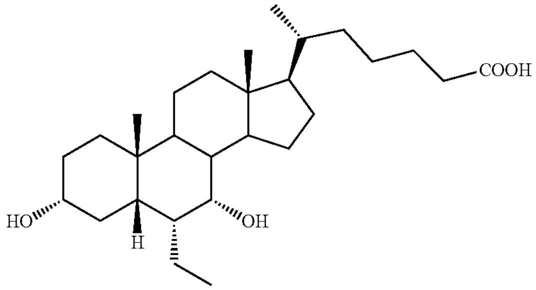
BAR803
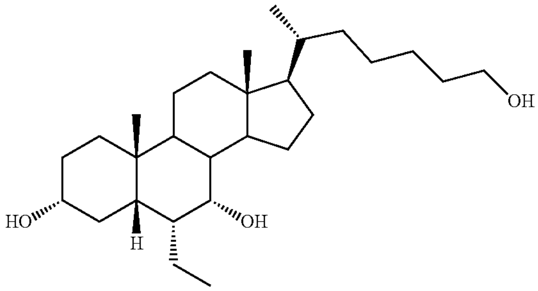
BAR804
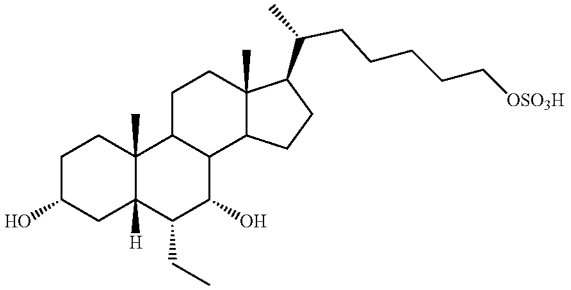
The compounds according to the invention, including compounds BAR107, BARn406, BAR504, BAR407 and BAR502, have been found to be highly selective FXR or TGR5/GPBAR1 modulators or dual FXR and TGR5/GPBAR1 modulators and are therefore useful as medicaments in particular for use in the prevention and/or treatment of gastrointestinal disorders, liver diseases, cardiovascular diseases, atherosclerosis, metabolic diseases, metabolic disorders, infectious diseases, cancer, renal disorders, inflammatory disorders, and neurological disorders such as stroke.

In certain embodiments the liver disease is selected in the group consisting of chronic liver diseases including primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant, liver regeneration, congenital hepatic fibrosis, granulomatous liver disease, intra- or extra-hepatic malignancy, Wilson's disease, hemochromatosis, and alpha 1-antitrypsin deficiency.

In certain embodiments the gastrointestinal disease is selected in the group consisting of inflammatory bowel disease (IBD) (including Crohn's disease, ulcerative colitis and undetermined colitis), irritable bowel syndrome (IBS), bacterial overgrowth, acute and chronic pancreatitis, malabsorption, post-radiation colitis, and microscopic colitis.

In certain embodiments the renal disease is selected in the group consisting of diabetic nephropathy, hypertensive nephropathy, chronic glomerular disease, including chronic glomerulonephritis and chronic transplant glomerulopathy, chronic tubulointerstitial diseases and vascular disorders of the kidney.

In certain embodiments the cardiovascular disease is selected in the group consisting of atherosclerosis, dyslipidemia, hypercholesterolemia, hypertriglyceridemia, hypertension also known as arterial hypertension, inflammatory heart disease including myocarditis and endocarditis, ischemic heart disease stable angina, unstable angina, myocardial infarction, cerebrovascular disease including ischemic stroke, pulmonary heart disease including pulmonary hypertension, peripheral artery disease (PAD), also known as peripheral vascular disease (PVD) peripheral artery occlusive disease, and peripheral obliterative arteriopathy.

In certain embodiments the metabolic disease is selected in the group consisting of insulin resistance, metabolic syndrome, Type I and Type II diabetes, hypoglycemia, disorders of adrenal cortex including adrenal cortex insufficiency.

In certain embodiments metabolic disorder is selected in the group consisting of obesity and conditions associated to bariatric surgery.

In certain embodiments cancer is selected in the group of liver cancer, bile duct cancers, pancreatic cancer, gastric cancer, colon-rectal cancer, breast cancer, ovary cancer and condition associated with chemotherapy resistance.

In certain embodiments infectious disorder is selected in the group of human immunodeficiency associated disease (AIDS) and related disorders, virus B and Virus C infection.

In certain embodiments inflammatory disorder is selected in the group of rheumatoid arthritis, fibromyalgia, Syogren's syndrome, scleroderma, Behcet's syndrome, vasculitis and systemic lupus erythematosus.

The data on the activity of certain compounds of the invention on FXR and TGR5/GPBAR1 are described in the following table. In this table, activities for compounds of the invention on FXR and GPBAR1 was compared to those of reference compounds: i.e. CDCA for FXR and TLCA for TGR5/GPBAR1. Each compound was tested at the concentration of 10 microM and transactivation activity of CDCA on FXR and TLCA on CRE (i.e. TGR5/GPBAR1) was considered equal to 100%.

TABLE 1

| Compounds of formula (I) | FXR (% of activity in comparison to 10 μM CDCA) | GPBAR1 (% of activity in comparison to 10 μM TLCA) |
|---|---|---|
| BAR106 | 0 | 19.0 ± 1.3 |
| BAR107 | 1.8 ± 0.3 | 9.9 ± 1.7 |
| BAR305 | 0 | 23.9 ± 4.0 |
| BAR304 | 0 | 55.1 ± 12.5 |
| BAR402 | 336.4 ± 20.8 | 28.0 ± 1.8 |
| BARn406 | 27.0 ± 1.5 | 4.8 ± 1.8 |
| BAR407 | 177.1 ± 3.5 | 37.3 ± 2.5 |
| BAR501 | 9.9 ± 0.1 | 64.5 ± 0.5 |
| BAR501-6a | 15.4 ± 1.2 | 46.6 ± 6.7 |
| BARn501 | 8.5 ± 1.4 | 83.1 ± 7.4 |
| BAR502 | 263.0 ± 32.0 | 74.5 ± 6.4 |
| BAR503 | 68.8 ± 26.6 | 59.8 ± 0.1 |
| BAR504 | 488.5 ± 17.5 | 103.0 ± 12.1 |
| BAR504-6b | 32.4 ± 14.1 | 75.3 ± 3.4 |
| BAR506 | 411.5 ± 36.5 | 80.9 ± 9.5 |
| BAR701 | 101.3 ± 10.1 | 50.2 ± 2.3 |
| BARn701 | 90 ± 22 | 55 ± 1.0 |
| BAR701solf | 229 ± 2.0 | 63.5 ± 0.5 |
| BAR702 | 11.7 ± 0.8 | 35.8 ± 1.2 |
| BAR703 | 8.6 ± 0.8 | 47.7 ± 1.0 |
| BAR704 | 220.5 ± 37.5 | 27.9 ± 6.3 |
| BARn704 | 202.5 ± 1.5 | 64 ± 2.0 |
| BAR705 | 43.7 ± 3.9 | 67.0 ± 9.9 |
| BAR706 | 153 ± 9.0 | 66.05 ± 7.6 |
| BARn706 | 197.5 ± 4.5 | 69.5 ± 6.5 |
| BARn706solf | 120 ± 9.5 | 71.5 ± 0.5 |
| BAR707 | 92.5 ± 7.5 | 65 ± 6.0 |
| BAR708 | 6.4 ± 0.8 | 57.6 ± 4.6 |
| BAR709 | 33.7 ± 2.0 | 54.2 ± 0.3 |
| BAR710 | 179 ± 43 | 49.5 ± 0.5 |
| BARn710 | 142 ± 1.0 | 75 ± 8.0 |
| BAR712 | 33.0 ± 0.15 | 49.7 ± 1.2 |
| BAR802 | 11.5 ± 8.5 | 56 ± 5.0 |
| BAR803 | 122.5 ± 5.5 | 80.5 ± 5.0 |
| BAR804 | 196.5 ± 6.5 | 52.5 ± 3.5 |

For one aspect, the present invention relates to compounds of formula (I) wherein the compounds are FXR and TGR5/GPBAR1 dual agonists. A selected example in this group is BAR502. Surprisingly, BAR502 does not induce itching when administered to animals rendered cholestatic by administration of ANIT or Estrogen. In cholestatic syndromes, body accumulation of bile acids is thought to cause itching. Recently, TGR5/GPBAR1 shown to mediate itching caused by intradermal administration of DCA and LCA (Alemi et al. J. Clin. Invest. 2013, 123, 1513-1530). In clinical trials, administration of patients suffering from primary biliary cirrhosis (PBC) with obeticholic acid has resulted in severe itching in approximately 80% of patients. One specific and surprising advantage of BAR502 is that this agent do not induce itching when administered to animals rendered cholestatic by administration of α-naphthyl-isothiocyanate (ANIT) or 17α-ethynylestradiol (two validated model of cholestasis). In these experimental setting BAR502 administration increases survival, attenuates serum alkaline phosphatase levels and robustly modulates the liver expression of canonical FXR target genes including OSTα, BSEP, SHP and MDR1, without inducing pruritus. In the 17α-ethynylestradiol model, BAR502 attenuates cholestasis and reshapes bile acid pool without inducing itching, demonstrating that in models of non-obstructive cholestasis, BAR502 attenuates liver injury without causing itching.

In one aspect, the present invention relates to compounds of formula (I) wherein the compounds are high selective FXR agonists without effects on GPBAR1 when administered alone but effective in inhibiting GPBAR1 activation caused by TLCA (10 μM), thus behaving as GPBAR1 antagonists. In one aspect, the present invention relates to compounds of formula (I) wherein the compounds are high selective GPBAR1 agonists without effects on FXR. In one aspect, the present invention relates to compounds of formula (I) wherein the compounds are high selective GPBAR1 antagonists without effects on FXR.

The present invention relates also to processes for preparing a compound of formula (I) as above described.

For an aspect the present invention relates to a process for preparing a compound of formula (I) as above described wherein R is $CH_2OH$, said process comprising contacting a corresponding compound of formula (I) wherein R is COOMe with $LiBH_4$.

For an aspect the present invention relates to a process for preparing a compound of formula (I) as above described wherein R is COOH, said process comprising subjecting a corresponding compound of formula (I) wherein R is COOMe to alkaline hydrolysis; preferably with NaOH 5% in $MeOH/H_2O$.

For an aspect the present invention relates to a process for preparing a compound of formula (I) as above described wherein R is $CH_2OSO_3H$ and salts thereof, said process comprising contacting a corresponding compound of formula (II)

(II)

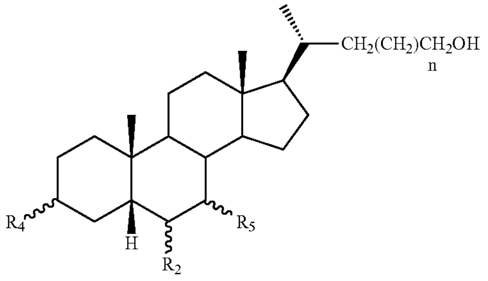

wherein n and $R_2$ are as above described and $R_4$ and $R_5$, if different from H, are OP, wherein P is an alcoholic protecting function, with a trialkylamine-sulfur trioxide for obtaining a compound of formula (III)

(III)

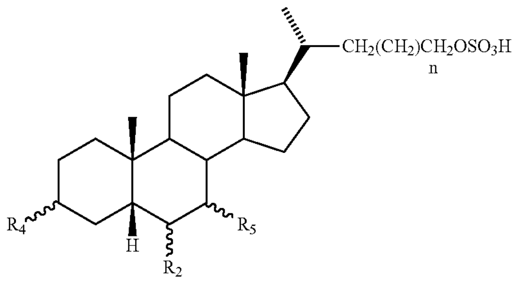

wherein n, $R_2$, $R_4$ and $R_5$ are as above described.

Then, from a compound of formula (III) as above described, the corresponding compound of formula (I) can be obtained by deprotection of the hydroxyl functions at C3 and C7.

For an aspect the present invention relates to a process for preparing a compound of formula (I) as above described, wherein n=3 said process comprising subjecting a corresponding compound of formula (IV)

(IV)

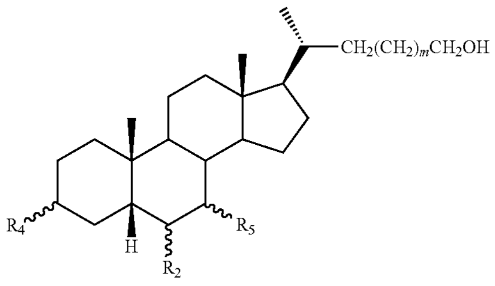

wherein m=n−2=1, $R_4$ and $R_5$, if other than H, are OP, wherein P is an alcoholic protecting function, and $R_2$ is as above described (preferably $R_2$ is H or alpha Et), to a one pot Swern oxidation/Wittig C2 homologation for obtaining a protected methyl ester of formula (V)

(V)

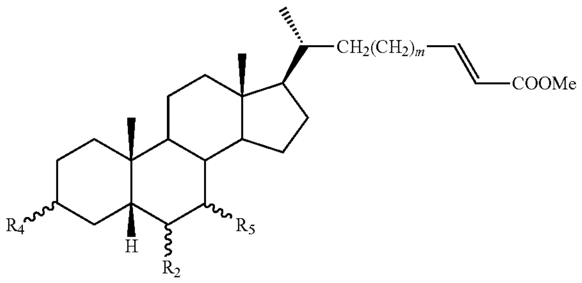

wherein m=1, $R_2$ is as above described (preferably $R_2$ is H or alpha-Et), $R_4$ and $R_5$, if other than H, are OP, wherein P is an alcoholic protecting function.

The Swern oxidation, is a chemical reaction whereby a primary or secondary alcohol is oxidized to an aldehyde or ketone using oxalyl chloride, dimethyl sulfoxide (DMSO) and an organic base, such as triethylamine.

The Wittig reaction, or Wittig olefination, is a chemical reaction of an aldehyde or ketone with a triphenyl phosphonium ylide (often called a Wittig reagent) to give an alkene and triphenylphosphine oxide. The triphenyl phosphonium ylide is preferably methyl(triphenylphosphoranylidene)acetate.

Preferably, the above process, can further comprising subjecting a compound of formula (V) as above described, to a catalytic hydrogenation thus affording a compound of formula (VI)

(VI)

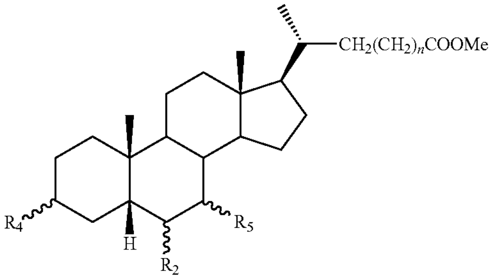

wherein n=m+2=3, $R_2$ is as above described, $R_4$ and $R_5$, if other than H, are OP, wherein P is an alcoholic protecting function.

Preferably OP is a silyl ether, more preferably t-butyldimethylsilyl ether. Therefore deprotection is preferably performed by acidic hydrolysis, preferably by treatment with HCl.

For an aspect the present invention relates to a process for preparing a compound of formula (I) as above described wherein n=0, said process comprising contacting a compound of formula (XII)

(XII)

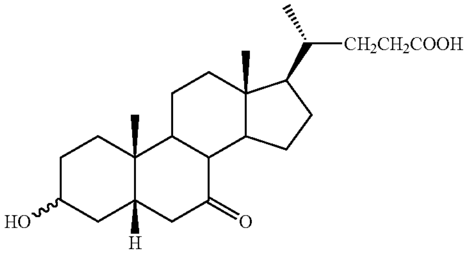

with HCOOH and $HClO_4$ and subsequently contacting the resulting compound with TFA, trifluoroacetic anhydride and $NaNO_2$ for obtaining a compound of formula (VII)

(VII)

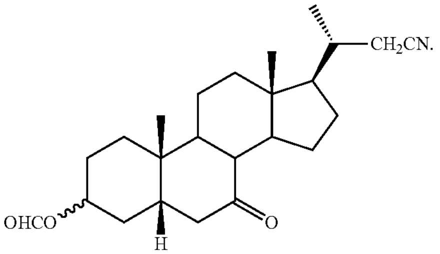

Simple and well known chemical transformations can then bring from a compound of formula (VII) to a compound of formula (I) as above described, so that the —CN group can be hydrolyzed to COOH, as well as the OCHO group can be hydrolyzed to hydroxyl group or =O group can be reduced to hydroxyl group.

For an aspect the present invention relates to a process for preparing a compound of formula (I) as above described wherein $R_2$ is =CH—$CH_3$ or Et and $R_3$ is not H, said process comprising subjecting a compound of formula (VIII) to an aldol condensation thus contacting a compound of formula (VIII)

(VIII)

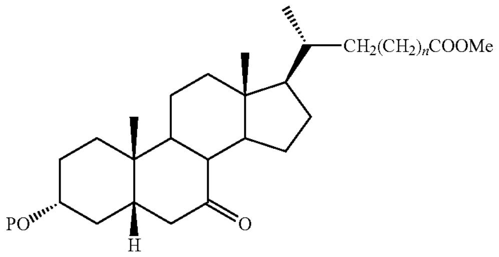

wherein n=0, 1, P is an alcoholic protecting function, preferably OAc, with alkyl lithium, such as nBuLi, and subsequently with acetaldehyde, preferably in presence also of $BF_3(OEt)_2$, for obtaining a compound of formula (IX)

(IX)

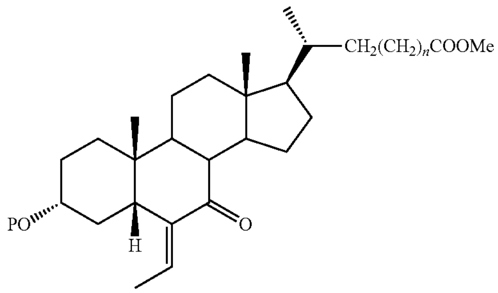

wherein n and P are as above described.

An aldol condensation is an aldol addition reaction, that might involve the nucleophilic addition of a ketone enolate to an aldehyde, wherein once formed, the aldol product loses a molecule of water to form an α,β-unsaturated carbonyl compound.

Subjecting a compound of formula (IX) to a catalytic hydrogenation, preferably with $H_2$ in presence of $Pd(OH)_2$/C, it can be obtained a compound of formula (X)

(X)

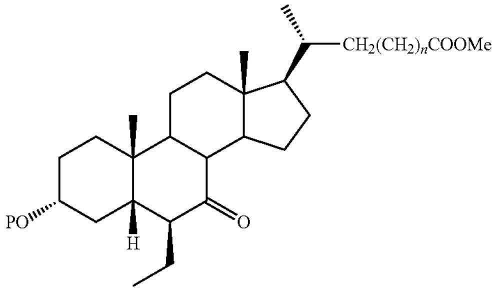

For an aspect the present invention relates to a process for preparing a compound of formula (I) wherein $R_2$ is alpha-Et, said process comprising contacting a compound of formula (XIV)

(XIV)

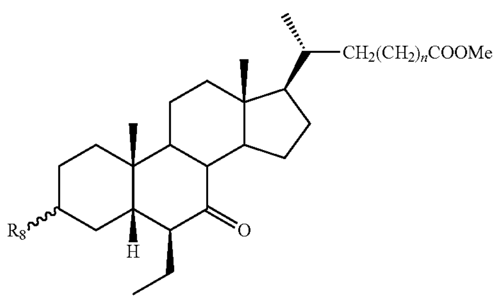

wherein n is 0 or 1, $R_8$ is beta-OH, OAc or H;

with MeONa/MeOH for obtaining epimerization of the C6 stereocenter thus obtaining a compound of formula (XI)

(XI)

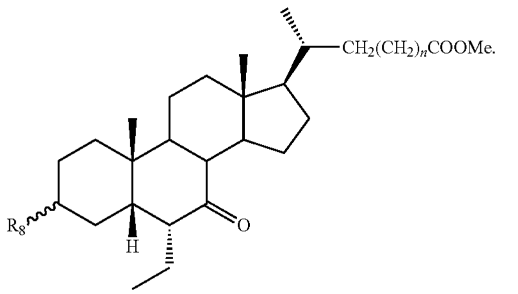

wherein n is 0 or 1, $R_8$ is as above described. In case $R_8$ is OAc the treatment with MeONa/MeOH afford simultaneously the C3 acetoxy group hydrolysis, thus obtaining a compound of formula (XI) wherein $R_8$ is OH.

Reduction of carbonyl at C7 can be obtained contacting a compound of formula (X) with $NaBH_4$ or $Ca(BH_4)_2$ for obtaining a mixture of beta-OH (up to 70% in case of compound BAR501 and BARn501) and alpha-OH at C7. Subsequent treatment with $LiBH_4$ reduces, if present, the methyl ester function in side chain to —$CH_2OH$ and the OAc protecting group at C3 to OH.

Reduction of carbonyl at C7 can be obtained contacting a compound of formula (XI) or corresponding compound having COOH at the side chain, with $LiBH_4$ obtaining almost exclusively alpha-OH at C7. Simultaneously the treatment with $LiBH_4$ reduces, if present, the methyl ester function in side chain to —$CH_2OH$ and the OAc protecting group at C3 to OH. Subjecting a compound of formula (IX) to a $NaBH_4$ reduction followed by treatment with $LiBH_4$, produced the reduction at C7 and at side chain with simultaneous deprotection, in particular deacetylation, at C3, for obtaining a compound of formula (I) wherein $R_1$ is alpha-OH, $R_2$ is =CH—$CH_3$, $R_3$ is beta-OH, n=0, 1 and R is CH2OH.

Subjecting the above compound of formula (I) wherein $R_1$ is alpha-OH, $R_2$ is =CH—$CH_3$, $R_3$ is beta-OH, n=0, 1 and R is $CH_2OH$ to a catalytic hydrogenation, preferably with $H_2$ and $Pd(OH)_2/C$, it can be obtained a compound of formula (I) wherein R1 is alpha-OH, $R_2$ is alpha-Et, $R_3$ is beta-OH, n=0, 1 and R is CH2OH For an aspect, the present invention relates to a process for preparing a compound of formula (I) wherein R1 is beta-OH, said process comprising starting from a compound of formula (XIII)

(XIII)

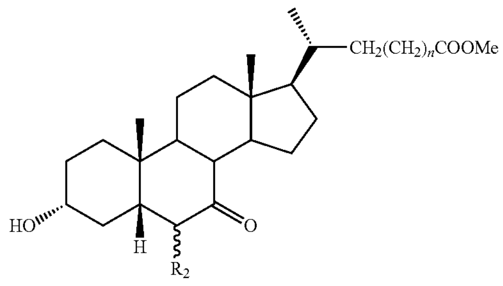

wherein $R_2$ is Et or H, preferably Et, and inverting the C3 hydroxy configuration by treatment with tosyl chloride in presence of a base then followed by a treatment with $CH_3COOK$.

For an aspect, the present invention relates to a process for preparing a compound of formula (I) wherein $R_1$ is H, said process comprising subjecting a compound of formula (XIII) (XIII) as above described to tosylation and elimination at C-3 hydroxyl group followed by double bond reduction.

Tosylation is preferably performed with TsCl and pyridine.

Elimination is preferably performed with LiBr and $Li_2CO_3$ in DMF at reflux temperature.

Double bond reduction is preferably performed by catalytic hydrogenation, preferably with $H_2$ and $Pd(OH)_2/C$.

The present invention could be better understood in light of the examples and experimental section below.

EXPERIMENTAL SECTION

Chemistry

Example 1. Preparation of Compounds of Formula (I) Wherein $R_2$=H

Example 1A. Synthesis of Bis-Homoursodeoxycholane Derivatives

A four-steps reaction sequence on 1, including protection of alcoholic functions at C3 and C7, reduction of the side chain methyl ester, and subsequent one pot Swern oxidation/Wittig C2 homologation gave the protected methyl ester of $\Delta^{24,25}$-bis-homoUDCA. Side chain double bond hydrogenation and alcoholic function deprotection gave bis-homoUDCA methyl ester 4, that was used as starting material in the preparation of BAR305 and it corresponding alcohol, BAR304, through treatment with LiOH and $LiBH_4$, respectively.

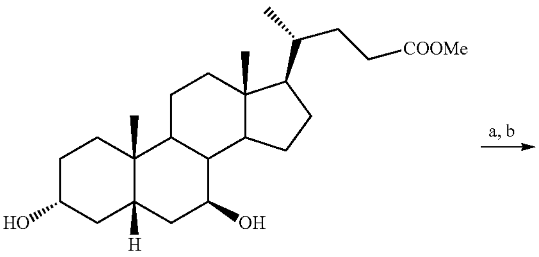

1

-continued

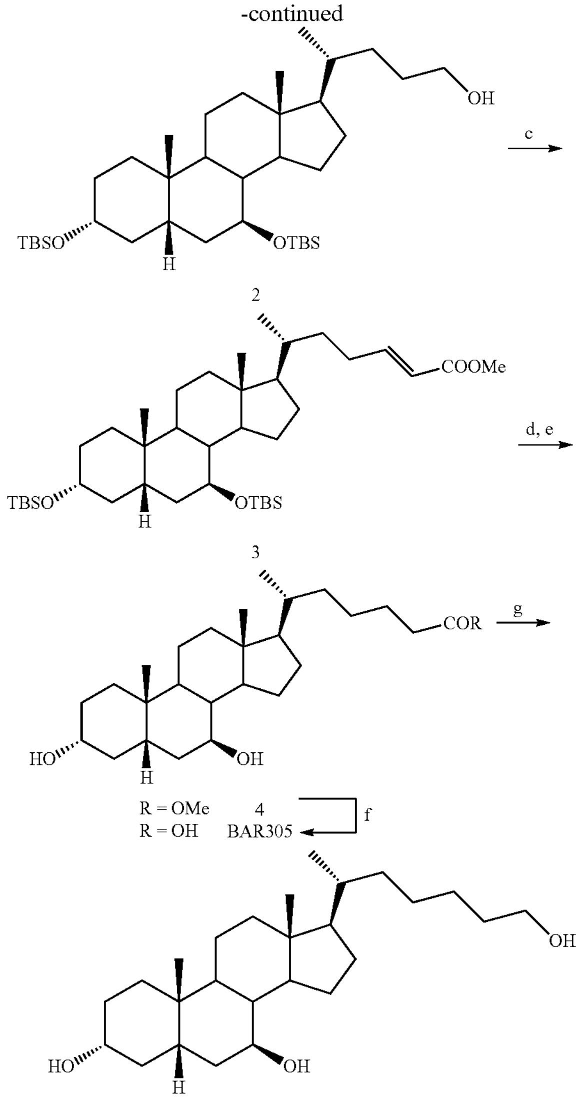

2

3

R = OMe 4

R = OH BAR305

BAR304 a) 2,6-lutidine, t-butyldimethylsilyl trifluoromethanesulfonate, $CH_2Cl_2$, 0° C.; b) $LiBH_4$, MeOH dry, THF, 0° C., quantitative yield over two steps; c) DMSO, oxalyl chloride, TEA dry, $CH_2Cl_2$, -78° C. then methyl(triphenylphosphoranylidene)acetate, 76%; d) $H_2$, $Pd(OH)_2/C$ Degussa type, THF/MeOH 1:1, quantitative yield; e) HCl 37%, MeOH, quantitative yield; f) NaOH 5% in $MeOH/H_2O$ 1:1 v/v, 60%; g) $LiBH_4$, MeOH dry, THF, 0° C., 77%.

Step a,b) Preparation of 3α, 7β-di(tert-butyldimethylsilyloxy)-5β-cholan-24-ol (2)

Compound 1 (1.2 g, 3 mmol) was protected at the two alcoholic function following the same synthetic procedure described in J. Med. Chem. 2014, 57, 937 to obtain 1.9 g of methyl 3α, 7β-di(tert-butyldimethylsilyloxy)-5□-cholan-24-oate (quantitative yield) in the form of colorless needles, that was subjected to next step without any purification.

Methanol (850 μL, 21 mmol) and $LiBH_4$ (10.5 mL, 2M in THF, 21 mmol) were added to a solution of methyl ester (1.9 g, 3 mmol) in dry THF (30 mL) at 0° C. following the same synthetic procedure described in J. Med. Chem. 2014, 57, 937. Purification by silica gel (hexane/ethyl acetate 99:1 and 0.5% TEA) gave 2 as a white solid (1.8 g, quantitative yield).

Step c) One pot preparation of methyl 3α, 7β-di(tert-butyldimethylsilyloxy)-25, 26-bishomo-5β-chol-24-en-26-oate (3)

DMSO (2.1 mL, 30 mmol) was added dropwise for 15 min to a solution of oxalyl chloride (7.5 mL, 15 mmol) in dry dichloromethane (30 mL) at −78° C. under argon atmosphere. After 30 min a solution of 2 (1.8 g, 3 mmol) in dry $CH_2Cl_2$ was added via cannula and the mixture was stirred at −78° C. for 30 min. $Et_3N$ (2.5 mL, 18 mmol) was added dropwise. After 1 h methyl(triphenylphosphoranylidene) acetate (2.0 g, 6 mmol) was added and the mixture was allowed to warm to room temperature. NaCl saturated solution was added and the aqueous phase was extracted with diethyl ether (3×100 mL). The combined organic phases were washed with water, dried ($Na_2SO_4$) and concentrated. Purification by silica gel (hexane-ethyl acetate 95:5 and 0.5% TEA) gave compound 3 as a colorless oil (1.5 g, 76%).

Step d) Preparation of methyl 3α, 7β-di(tert-butyldimethylsilyloxy)-25, 26-bishomo-5β-cholan-26-oate A solution of compound 3 (1.5 g, 2.3 mmol) in THF dry/MeOH dry (25 mL/25 mL, v/v) was hydrogenated in presence of $Pd(OH)_2$ 5% wt on activated carbon Degussa type (20 mg) following the same synthetic procedure described in J. Med. Chem. 2014, 57, 937 affording methyl 3α, 7β-di(tert-butyldimethylsilyloxy)-25, 26-bishomo-5β-cholan-26-oate (1.5 g, quantitative yield) that was subjected to step e) without purification.

Step e) Preparation of methyl 3α, 7β-dihydroxy-25, 26-bishomo-5β-cholan-26-oate (4)

Methyl 3α, 7β-di(tert-butyldimethylsilyloxy)-25, 26-bishomo-5β-cholan-26-oate (1.5 g) was dissolved in methanol (70 mL). At the solution HCl (2 mL, 37% v/v) was added following the same synthetic procedure described in J. Med. Chem. 2014, 57, 937 affording 4 as colorless amorphous solid (1.0 g, quantitative yield).

Step f) Preparation of 3α, 7β-dihydroxy-25, 26-bishomo-5β-cholan-26-oic acid (BAR305)

A portion of compound 4 (430 mg, 1 mmol) was hydrolyzed with NaOH (400 mg, 10 mmol) in a solution of MeOH: $H_2O$ 1:1 v/v (20 mL) for 4 h at reflux. An analytic sample was purified by HPLC on a Nucleodur 100-5 C18 (5 μm; 4.6 mm i.d.×250 mm) with $MeOH/H_2O$ (95:5) as eluent (flow rate 1 mL/min) ($t_R$=5 min).

BAR305: $C_{26}H_{44}O_4$

The $^1H$ NMR was recorded on Varian Inova 400 MHz, using $CD_3OD$ as solvent: δ 3.47 (2H, m, H-3 and H-7), 2.27 (2H, t, J=7.2 Hz, $H_2$-25), 0.96 (3H, s, $H_3$-19), 0.94 (3H, d, J=6.5 Hz, $H_3$-21), 0.70 (3H, s, $H_3$-18).

The $^{13}C$ NMR was recorded on Varian Inova 100 MHz, using $CD_3OD$ as solvent: δ 178.2, 72.1, 71.9, 57.6, 56.7, 44.8, 44.5, 44.0, 41.6, 40.7, 38.6, 38.0, 36.9, 36.8, 36.1, 35.3, 35.2, 30.9, 29.8, 27.9, 26.7, 26.6, 23.9, 22.4, 19.3, 12.7.

Step g) 25, 26-bishomo-5β-cholan-3α, 7β, 26-triol (BAR304)

Compound 4 (500 mg, 1.2 mmol) was reduced in the same operative condition described in step b). Purification by silica gel ($CH_2Cl_2$/methanol 9:1) gave BAR304 as a colorless oil (375 mg, 77%). An analytic sample was purified by HPLC on a Nucleodur 100-5 C18 (5 μm; 4.6 mm i.d.×250 mm) with MeOH/$H_2O$ (85:15) as eluent (flow rate 1 mL/min) ($t_R$=9 min).

BAR 304: $C_{26}H_{46}O_3$

The $^1H$ NMR was recorded on Varian Inova 400 MHz, using $CD_3OD$ as solvent: δ 3.53 (2H, t, J=6.5 Hz, $H_2$-26), 3.48 (2H, m, H-3 and H-7), 0.95 (3H, s, $H_3$-19), 0.93 (3H, d, J=6.5 Hz, $H_3$-21), 0.70 (3H, s, $H_3$-18).

The $^{13}C$ NMR was recorded on Varian Inova 100 MHz, using $CD_3OD$ as solvent: δ 72.1, 71.9, 63.0, 57.5, 56.7, 44.7, 44.4, 44.0, 41.6, 40.7, 38.5, 37.9, 37.2, 37.0, 36.1, 35.2, 33.7, 30.9, 29.8, 27.9, 27.4, 27.1, 23.9, 22.4, 19.4, 12.7.

Example 1B. Synthesis of 3α,7β-dihydroxy-24-nor-5β-cholan-23-yl-23-sodium sulfate (BAR106) and 3α,7β-dihydroxy-24-nor-5β-cholan-23-ol (BAR107)

BAR106 was prepared starting from UDCA by a reaction sequence comprising performylation at the hydroxyl groups, Beckmann one carbon degradation at C24 and transformation of the C23 carboxyl group into the corresponding methyl ester intermediate. Protection at the hydroxyl groups at C-3 and C-7 as silyl ethers, reduction at C23 methyl ester, sulfation at C23 primary alcoholic function and finally deprotection furnished crude BAR106 as ammonium salt. Purification on Amberlite and then by HPLC gave title BAR106 as sodium salt.

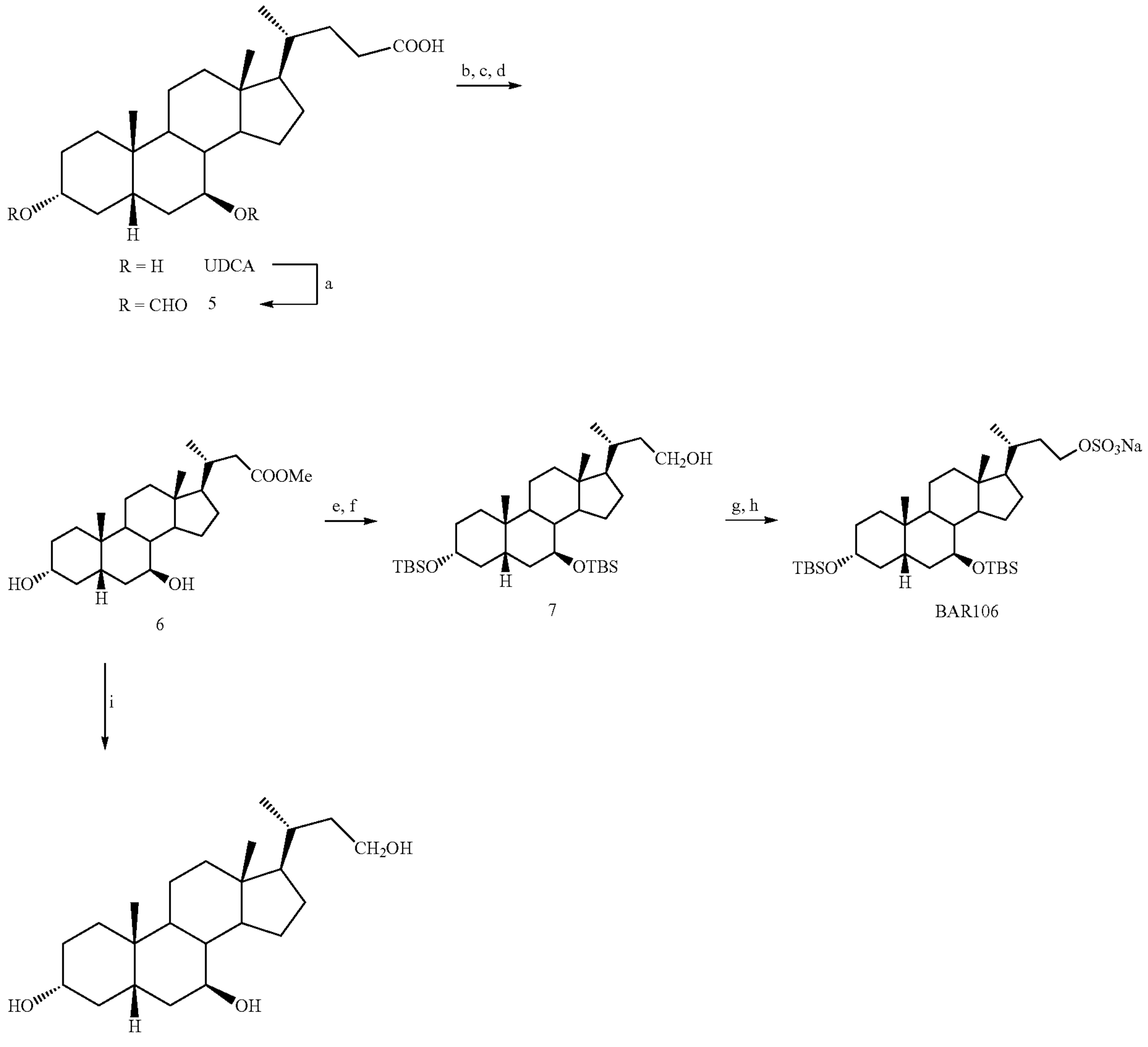

R = H UDCA
R = CHO 5
6
7
BAR106
BAR107 a) HCOOH, $HClO_4$, 96%; b) TFA, trifluoroacetic arhydride, $NaNO_2$, 96%; c) KOH 30% in MeOH/$H_2O$ 1:1 v/v, 97%; d) p-TsOH, MeOH dry, 98%; e) 2.6-lutidine, t-butyldimethylsily trifluoromethanesulfonate, $CH_2Cl_2$, 0° C., 88%; f) $LiBH_4$, MeOH dry, THF, 0° C., quantitative yield; g) $Et_3N$•$SO_3$, DMF, 95° C.; h) HCl 37%, MeOH, then Amberlite CG-120, MeOH, 86% over two steps; i) $LiBH_4$, MeOH dry, THF, 0° C., quantitative yield.

Steps a,d) Preparation of methyl 3α,7β-dihydroxy-24-nor-5β-cholan-23-oate (6)

Ursodeoxycholic acid (2.0 g, 5.1 mmol) was transformed in methyl 3α,7β-dihydroxy-24-nor-5β-cholan-23-oate (6, 1.6 g, 87%) following the same synthetic procedure described in J. Med. Chem. 2014, 57, 937.

Step e) Preparation of methyl 3α, 7β-di(tert-butyldimethylsilyloxy)-5β-cholan-24-oate Compound 6 (1.2 g, 3.0 mmol) was protected at the hydroxyl groups in the same operative condition described in example 1A step a). Purification by flash chromatography on silica gel using hexane/ethyl acetate 9:1 and 0.5% of triethylamine as eluent, gave protected methyl ester (1.6 g, 88%).

Step f) Preparation of 3α, 7β-di(tert-butyldimethylsilyloxy)-5β-cholan-24-ol (7)

Side chain methyl ester (818 mg, 1.3 mmol) was reduced in the same operative condition described in example 1A step b). Purification by flash chromatography on silica gel using hexane/ethyl acetate 98:2 and 0.5% of triethylamine as eluent, gave 7 (770 mg, quantitative yield).

Steps g, h) Preparation of 3α,7β-dihydroxy-24-nor-5β-cholan-23-yl-23-sodium sulfate (BAR106)

The triethylamine-sulfur trioxide complex (2.0 g, 11 mmol) was added to a solution of 7 (660 mg, 1.1 mmol) in DMF dry (25 mL) following the same synthetic procedure described in J. Med. Chem. 2014, 57, 937. HPLC on a Nucleodur 100-5 C18 (5 μm; 10 mm i.d.×250 mm) with $MeOH/H_2O$ (65:35) as eluent (flow rate 3 mL/min), gave 442 mg (86% over two steps) of BAR106 ($t_R$=8.4 min).

BAR 106: $C_{23}H_{39}NaO_6S$

The $^1H$ NMR was recorded on Varian Inova 400 MHz, using $CD_3OD$ as solvent: δ 4.04 (2H, m, $H_2$-23), 3.48 (2H, m, H-3 and H-7), 1.00 (3H, d, J=6.5 Hz, $H_3$-21), 0.97 (3H, s, $H_3$-19), 0.72 (3H, s, $H_3$-18).

Step i) Preparation of 3α, 7β-dihydroxy-24-nor-5β-cholan-23-ol (BAR107)

Compound 6 was transformed in BAR107 in the same operative condition described in step f.

BAR107: $C_{23}H_{40}O_3$

The $^1H$ NMR was recorded on Varian Inova 400 MHz, using $CD_3OD$ as solvent: δ 3.60 (1H, m, H-7), 3.51 (1H, m, H-3), 3.50 (2H, m, $H_2$-23), 0.97 (3H, d, ovl, $H_3$-21), 0.96 (3H, s, $H_3$-19), 0.72 (3H, s, $H_3$-18).

The $^{13}C$ NMR was recorded on Varian Inova 100 MHz, using $CD_3OD$ as solvent: δ 72.1, 71.9, 60.8, 57.5, 57.1, 44.8, 44.5, 44.0, 41.6, 40.7, 39.9, 38.6, 38.0, 36.1, 35.2, 34.1, 31.0, 29.8, 27.9, 23.9, 22.4, 19.5, 12.6;

Example 1C. Synthesis of 7α-hydroxy-5β-cholan-24-yl-24-sodium sulfate (BAR402)

Tosylation and elimination at C-3 hydroxyl group on methyl ester 8 followed by double bond reduction, subsequent $LiBH_4$ treatment and regioselective sulfation at C-24 primary hydroxyl group gave BAR402.

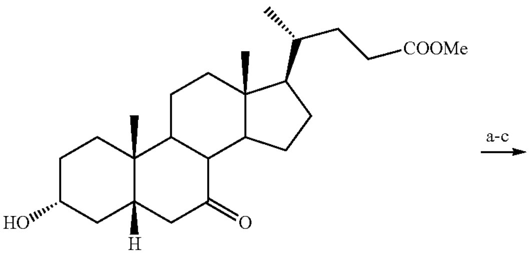

8

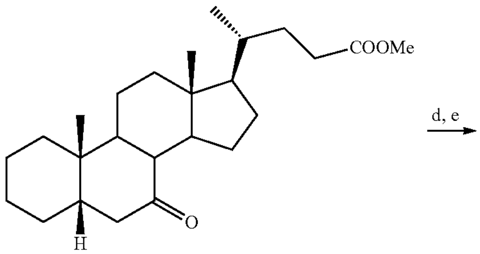

9

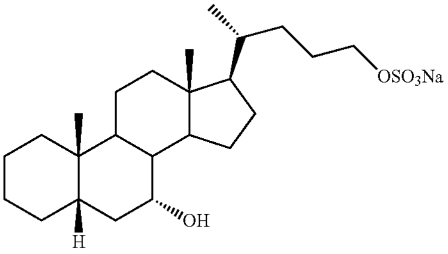

BAR402 a) p-TsCl, pyridine, quantitative yield; b) LiBr, $Li_2CO_3$, DMF, reflux, c) $H_2$, $Pd(OH)_2$, THF/MeOH 1:1, room temperature, quantitative yield; d) $LiBH_4$, MeOH dry, THF, 0° C., 79%; e) $Et_3N$•$SO_3$, DMF, 95° C.

Steps a-c) Preparation of methyl 7-keto-5β-cholan-24-oate (9)

To a solution of 8 (965 mg, 2.5 mmol) in dry pyridine (100 mL), tosyl chloride (4.7 g, 25.0 mmol) was added, and the mixture was stirred at room temperature for 4 h. It was poured into cold water (150 mL) and extracted with $CH_2Cl_2$ (3×150 mL). The combined organic layer was washed with saturated $NaHCO_3$ solution (150 mL), and water (150 mL), and then dried over anhydrous $MgSO_4$ and evaporated in vacuo to give 1.4 g of methyl 3α-tosyloxy-7-keto-5β-cholan-24-oate (quantitative yield). Lithium bromide (434 mg, 5.0 mmol) and lithium carbonate (370 mg, 5.0 mmol) were added to a solution of 3α-tosyloxy-7-keto-5β-cholan-24-oate (1.4 g, 2.5 mmol) in dry DMF (30 mL), and the mixture was refluxed for 2 h. After cooling to room temperature, the mixture was slowly poured into 10% HCl solution (20 mL) and extracted with $CH_2Cl_2$ (3×50 mL). The combined organic layer was washed successively with water, saturated $NaHCO_3$ solution and water, and then dried over anhydrous $MgSO_4$ and evaporated to dryness to give 965 mg of oleos residue (quantitative yield), that was subjected to next step without any purification. Hydrogenation on $Pd(OH)_2$ in the same operative condition described in example 1A, step d furnished 975 mg of 9 (quantitative yield), that was subjected to next step without any purification.

Step d) Preparation of 5β-cholan-7α,24-diol $LiBH_4$ treatment on compound 9 in the same operative condition described in example 1A step b and purification by silica gel (ethyl acetate-hexane, 85:15) gave 5β-cholan-7α,24-diol as a white solid (714 mg, 79%).

Step e) Preparation of 7α-hydroxy-5β-cholan-24-yl-24-sodium sulfate (BAR402)

Sulfation on C24 was performed in the same operative conditions described in example 1B step g) to give crude BAR402 as ammonium salt. RP18/HPLC on a Nucleodur 100-5 C18 (5 μm; 10 mm i.d.×250 mm) with $MeOH/H_2O$ (90:10) as eluent (flow rate 3 mL/min) afforded BAR402 ($t_R$=6.6 min) as sodium salt.

BAR402: $C_{24}H_{41}NaO_5S$

The $^1H$ NMR was recorded on Varian Inova 400 MHz, using $CD_3OD$ as solvent: δ 3.96 (2H, t, J=6.6 Hz, $H_2$-24), 3.78 (1H, br s, H-7), 0.96 (3H, d, J=6.5 Hz, $H_3$-21), 0.92 (3H, s, $H_3$-19), 0.69 (3H, s, $H_3$-18);

The $^{13}C$ NMR was recorded on Varian Inova 100 MHz, using $CD_3OD$ as solvent: δ 69.7, 69.4, 57.7, 51.6, 45.0, 43.8, 41.2, 41.0, 39.0, 37.1, 37.0 36.3, 34.2, 33.3, 31.7, 29.5, 29.0, 27.3, 24.8, 24.3, 22.7, 21.9, 19.2, 12.3.

Example 2. Preparation of Compounds of Formula (I) Wherein $R_2$=Et or =CH—$CH_3$ Example 2A. Synthesis of 6β-ethyl-3α,7β-dihydroxy-5β-cholan-24-ol (BAR501)

Methyl ester formation and acetylation at C-3 hydroxyl group on 7-KLCA furnished intermediate 10 in 84% yield over two steps. Aldolic addition to a silyl enol ether intermediate generated 11 that was hydrogenated at the exocyclic double bond ($H_2$ on $Pd(OH)_2$) affording 12 in 80% yield over three steps. $NaBH_4$ treatment in methanol followed by $LiBH_4$ reduction on the crude reaction product afforded a mixture whose HPLC purification (88% $MeOH:H_2O$) gave pure BAR501 in a 79% yield respect to its C7 epimer, BAR504-6b.

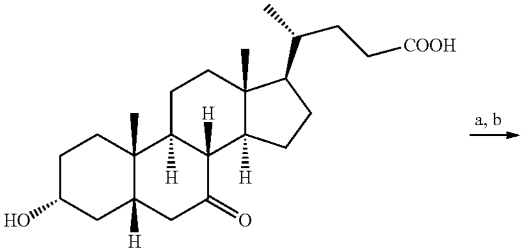

7-KLCA

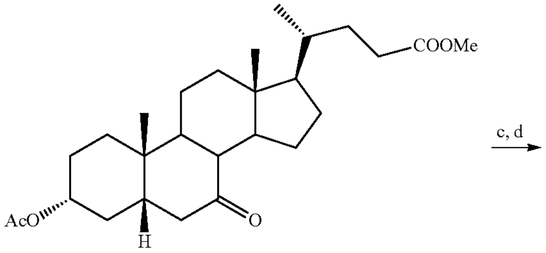

10

-continued

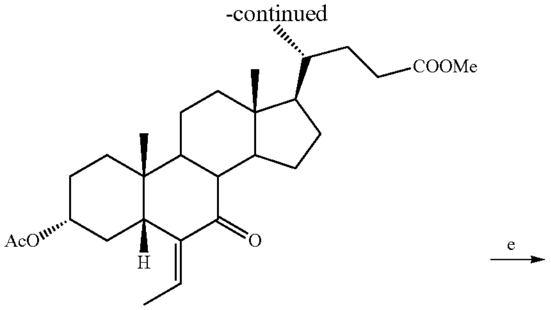

11

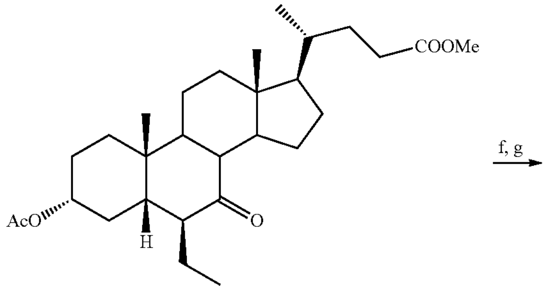

12

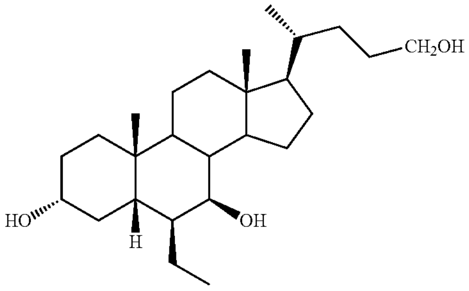

BAR501

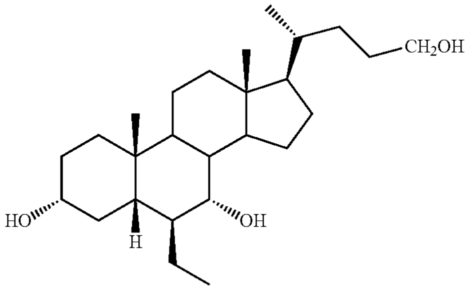

BAR504-6b a) p-TsOH, MeOH dry; b) acetic anhydride, pyridine, 84% yield over two steps; c) DIPA, n-BuLi, TMSCl, TEA dry -78° C.; d) acetaldehyde, $BF_3(OEt)_2$, $CH_2Cl_2$, -60° C., 80% over two steps; e) $H_2$, $Pd(OH)_2$, THF/MeOH 1:1. quantitative yield; f) $NaBH_4$, MeOH; g) $LiBH_4$, MeOH dry, THF, 0° C., 79% over two steps.

Steps a-d). Preparation of methyl 3α-acetoxy-6-ethylidene-7-keto-5β-cholan-24-oate (11)

To a solution of 7-ketolithocholic acid (5 g, 12.8 mmol), dissolved in 100 mL of dry methanol was added p-toluenesulfonic acid (11 g, 64.1 mmol). The solution was left to stand at room temperature for 2 h. The mixture was quenched by addition of $NaHCO_3$ saturated solution. After the evaporation of the methanol, the residue was extracted with EtOAc (3×150 mL). The combined extract was washed with brine, dried with $Na_2SO_4$, and evaporated to give the methyl ester as amorphous solid (5.13 g, quantitative yield).

At the solution of the methyl ester (5.13 g, 12.7 mmol) in dry pyridine (100 mL), an excess of acetic anhydride (8.4 mL, 89 mmol) was added. When the reaction was complete, the pyridine was concentrated under vacuum. The residue was poured into cold water (100 mL) and extracted with AcOEt (3×150 mL). The combined organic phases were dried ($Na_2SO_4$) and concentrated to give a residue that was further purified by flash chromatography on silica gel using hexane/ethyl acetate 8:2 and 0.5% of triethylamine as eluent (4.8 g of 10 as a white solid, 84% yield over two steps).

To a solution of diisopropylamine (23 mL, 0.16 mol) in dry THF (50 mL) was added dropwise a solution of n-butyllithium (60 mL, 2.5 M in hexane, 0.15 mol) at −78° C. After 30 min, trimethylchlorosilane (27.1 mL, 0.21 mol) was added. After additional 30 min, a solution of compound 10 (4.8 g, 10.7 mmol) in dry THF (70 mL) was added. The reaction was stirred at −78° C. for an additional 45 min and then triethylamine (54 mL, 0.38 mol) was added. After 1 h, the reaction mixture was allowed to warm to −20° C., treated with aqueous saturated solution of $NaHCO_3$ (100 mL) and brought up to room temperature in 2 h. The aqueous phase was extracted with ethyl acetate (3×50 mL). The combined organic phases were washed then with saturated solution of $NaHCO_3$, water and brine. After drying over anhydrous $Na_2SO_4$, the residue was evaporated under vacuum to give 6 g of yellow residue, that was diluted in dry $CH_2Cl_2$ (50 mL) and cooled at −78° C. At this stirred solution acetaldehyde (3 mL, 53 mmol) and $BF_3.OEt_2$ (13.5 mL, 0.107 mol) were added dropwise. The reaction mixture was stirred for 2 h at −60° C. and allowed to warm to room temperature. The mixture was quenched with saturated aqueous solution of $NaHCO_3$ and extracted with $CH_2Cl_2$. The combined organic phases were washed with brine, dried over anhydrous $Na_2SO_4$ and concentrated under vacuum.

Purification by silica gel (hexane-ethyl acetate 9:1 and 0.5% TEA) gave compound 11 (4.1 g, 80%). NMR analysis demonstrated a diasteromeric ratio E/Z>95%. The E configuration at the exocyclic double bond was established by dipolar coupling $H_3$-26 (δ 1.67)/H-5 (δ 2.62) in Noesy spectrum (400 MHz, mixing time 400 ms).

(E)-3α-acetoxy-6-ethylidene-7-keto-5β-cholan-24-oate (11): $C_{29}H_{44}O_5$

The $^1H$ NMR was recorded on Varian Inova 400 MHz, using $CDCl_3$ as solvent: δ 6.16 (1H, q, J=7.0 Hz, H-25), 4.74 (1H, m, H-3), 3.64 (3H, s, $COOCH_3$), 2.62 (1H, dd, J=13.0, 3.6 Hz, H-5), 1.98 (3H, s, $COCH_3$), 1.67 (3H, d, J=7.0 Hz, $H_3$-26), 1.00 (3H, s, $H_3$-19), 0.92 (3H, d, J=6.0 Hz, $H_3$-21), 0.67 (3H, s, $H_3$-18).

The $^{13}C$ NMR was recorded on Varian Inova 100 MHz, using $CDCl_3$ as solvent: δ 204.5, 174.6, 170.7, 143.1, 130.2, 72.5, 54.5, 51.4, 50.7, 48.6, 45.2, 43.5, 39.1, 38.9, 35.1, 34.9, 34.1, 33.4, 31.0, 30.9, 28.4, 25.9 (2C), 22.8, 21.4, 21.2, 18.4, 12.7, 12.2.

Steps e) Preparation of methyl 3α-acetoxy-6β-ethyl-7-keto-5β-cholan-24-oate (12)

A solution of 11 (4.0 g, 8.5 mmol) in THF dry/MeOH dry (100 mL, 1:1 v/v) was hydrogenated in presence of $Pd(OH)_2$ 20% wt on activated carbon (100 mg) degussa type. The mixture was transferred to a standard PARR apparatus and flushed with nitrogen and then with hydrogen several times. The apparatus was shacked under 50 psi of $H_2$. The reaction was stirred at room temperature for 8 h. The catalyst was filtered through Celite, and the recovered filtrate was concentrated under vacuum to give 12 (4.0 g, quantitative yield).

Methyl 3α-acetoxy-6β-ethyl-7-keto-5β-cholan-24-oate (12): $C_{29}H_{46}O_5$

The $^1H$ NMR was recorded on Varian Inova 400 MHz, using $CD_3OD$ as solvent: δ 4.65 (1H, m, H-3), 3.66 (3H, s, $COOCH_3$), 2.56 (1H, t, J=11.5 Hz, H-8), 2.35 (1H, m, H-23a), 2.22 (1H, m, H-23b), 1.99 (3H, s, $COCH_3$), 1.22 (3H, s, $H_3$-19), 0.92 (3H, d, J=6.3 Hz, $H_3$-21), 0.83 (3H, t, J=7.2 Hz, $H_3$-26), 0.67 (3H, s, $H_3$-18).

The $^{13}C$ NMR was recorded on Varian Inova 100 MHz, using $CD_3OD$ as solvent: δ 214.7, 174.3, 170.2, 72.6, 61.7, 54.8, 51.3, 49.0, 48.5, 45.3, 42.7, 42.3 (2C), 38.6, 35.4, 35.1, 35.0, 31.0, 30.8, 28.0 (2C), 26.4, 25.7, 24.7, 21.3, 21.1, 18.2, 12.9, 11.9.

The β configuration of ethyl group at C-6 was determined by dipolar couplings $H_3$-26 (δ 0.83)/$H_3$-19 (δ 1.22) and H-8 (δ 2.56)/H-25 (δ 1.83) in Noesy spectrum (400 MHz, mixing time 400 ms).

Steps f,g) Preparation of 6β-ethyl-3α,7β-dihydroxy-5β-cholan-24-ol (BAR501)

To a methanol solution of compound 12 (1.18 g, 2.5 mmol), a large excess of $NaBH_4$ was added at 0° C. The mixture was left at room temperature for 2 h and then water and MeOH were added dropwise during a period of 15 min at 0° C. with effervescence being observed. After evaporation of the solvents, the residue was diluted with water and extracted with AcOEt (3×50 mL). The combined extract was washed with brine, dried with $Na_2SO_4$, and evaporated to give 1.3 g of a crude residue that was subjected to the next step without further purification. The crude residue was treated with $LiBH_4$ (2 M in THF) in the same operative condition described in example 1A step b). HPLC purification on a Nucleodur 100-5 C18 (5 μm; 10 mm i.d.×250 mm) with MeOH/$H_2O$ (88:12) as eluent (flow rate 3 mL/min), gave 802 mg of BAR501 (79%, $t_R$=11 min).

Alternatively step f was performed with $Ca(BH_4)_2$, produced in situ.

To a solution of compound 12 (500 mg, 1.05 mmol) and absolute ethanol (4 mL), at 0° C., $CaCl_2$ (466 mg, 4.2 mmol) was added. At the same solution was added a solution of $NaBH_4$ (159 mg, 4.2 mmol) in absolute ethanol (4 mL). After 4 h at −5° C., MeOH was added dropwise. Then after evaporation of the solvents, the residue was diluted with water and extracted with AcOEt (3×50 mL). The combined extract was washed with brine, dried with $Na_2SO_4$, and evaporated to give 500 mg of a crude residue that was subjected to the step g without further purification.

BAR501: $C_{26}H_{46}O_3$

The $^1H$ NMR was recorded on Varian Inova 700 MHz, using $CD_3OD$ as solvent: δ 3.74 (1H, dd, J=10.3, 6.0 Hz, H-7), 3.51 (1H, ovl, H-3), 3.49 (2H, ovl, $H_2$-24), 1.00 (3H, s, $H_3$-19), 0.97 (3H, d, J=6.5 Hz, $H_3$-21), 0.96 (3H, t, J=7.6 Hz, $H_3$-26), 0.72 (3H, s, $H_3$-18).

The $^{13}C$ NMR was recorded on Varian Inova 175 MHz, using $CD_3OD$ as solvent: δ 75.3 71.9, 63.6, 57.5, 56.5, 51.6, 45.7, 44.9, 42.1, 41.5, 40.4, 40.3, 37.1, 35.8, 32.4, 30.7, 30.3, 29.7, 29.6, 28.3, 26.2, 23.4, 22.1, 19.4, 14.8, 12.7.

Example 2B. Preparation of 6β-ethyl-3α,7α-dihydroxy-5β-cholan-24-ol (BAR504-6b)

BAR504-6b was prepared as described in the Example 2A ($t_R$=20.4 min).

BAR504-6b: $C_{26}H_{46}O_3$

The $^1$H NMR was recorded on Varian Inova 700 MHz, using $CD_3OD$ as solvent: δ 3.60 (1H, s, H-7), 3.51 (2H, m, $H_2$-24), 3.35 (1H, ovl, H-3), 2.30 (1H, q, J=13.5 Hz, H-4a), 0.97 (3H, d, J=6.8 Hz, $H_3$-21), 0.95 (3H, t, J=7.3 Hz, $H_3$-26), 0.94 (3H, s, $H_3$-19), 0.70 (3H, s, $H_3$-18).

The $^{13}$C NMR was recorded on Varian Inova 175 MHz, using $CD_3OD$ as solvent: δ 71.9, 71.8, 62.7, 56.8, 51.7, 50.5, 46.7, 42.5, 41.4, 40.1, 36.6, 36.4, 36.2, 36.0, 33.2, 32.4, 30.1, 29.5, 28.8, 28.5, 25.3, 23.9, 20.7, 18.4, 13.7, 11.4.

Example 2C. Synthesis of 6α-ethyl-3α, 7α-dihydroxy-24-nor-5β-cholan-23-ol (BAR502), 6β-ethyl-3α, 7β-dihydroxy-24-nor-5β-cholan-23-ol (BARn501) and 6β-ethyl-3α, 7α-dihydroxy-24-nor-5β-cholan-23-ol (BARn504-6b)

7-KLCA (1 g, 2.56 mmol) was subjected to Beckmann degradation at C24 and methylation at C-23 furnishing 13 in 66% yield. Acetylation at C-3 and alkylation furnished 14 that was hydrogenated affording 15. MeONa/MeOH treatment gave concomitant hydrolysis at C-3 and epimerization at C-6. Simultaneous reduction at C-23 methyl ester function and at C-7 carbonyl group furnished BAR502 in 89% yield. Intermediate 15 (250 mg, 0.54 mmol) was also used as starting material in the preparation of BARn501 and BARn504-6b.

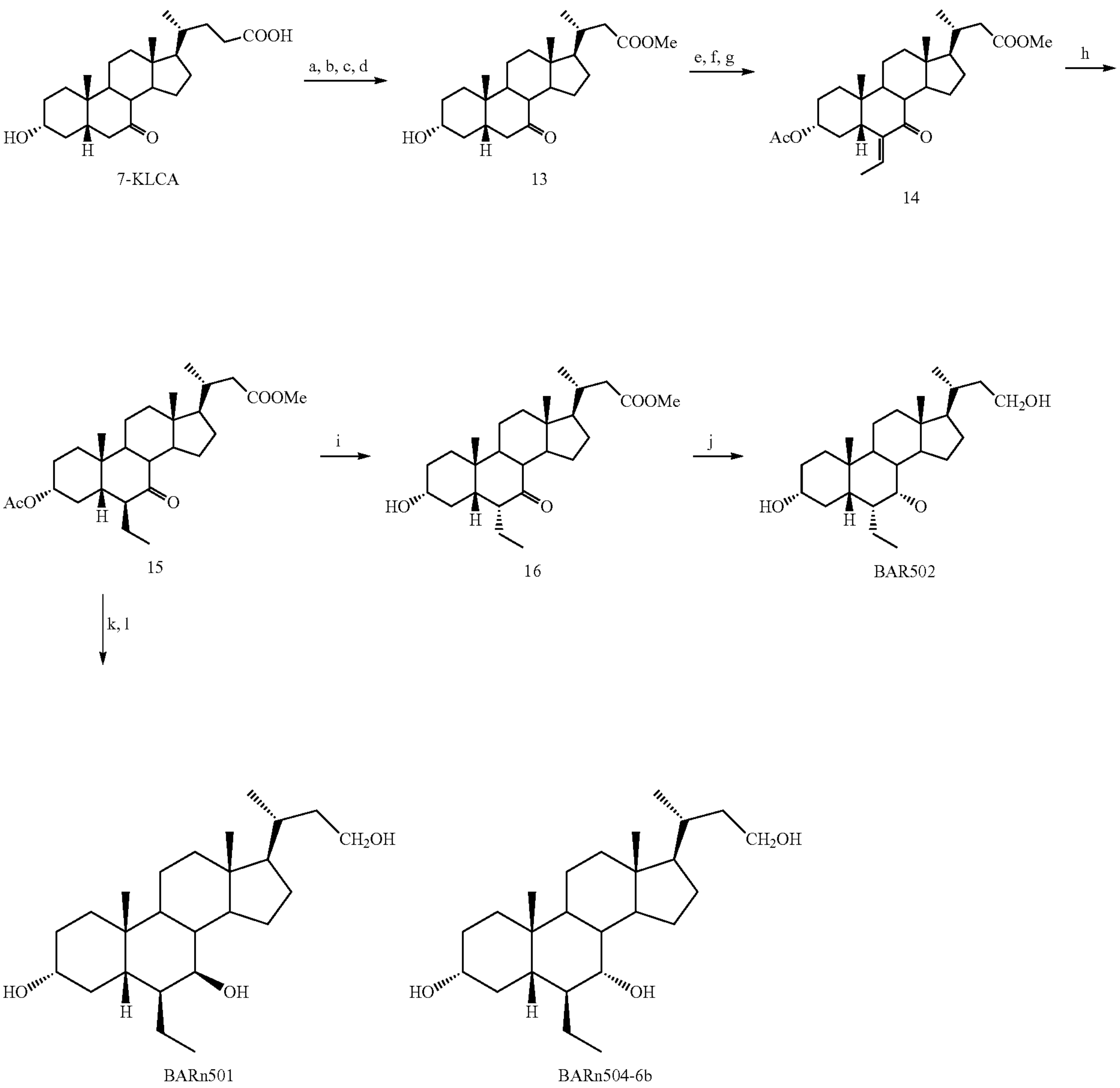

a) HCOOH, $HClO_4$; b) TFA, trifluoroacetic anhydride, $NaNO_2$; c) KOH 30% in $MeOH/H_2O$ 1:1 v/v, 88% over three steps; d) p-TsOH, MeOH dry; e) acetic anhydride, pyridine; f) DIPA, n-BuLi, TMSCl, TEA dry, THF dry -78° C.; g) acetaldehyde, $BF_3(OEt)_2$, $CH_2Cl_2$, -60° C., 60% over four steps; h) $H_2$, $Pd(OH)_2$, THF/MeOH 1:1, quantitative yield; i) MeONa; MeOH; j) $LiBH_4$, MeOH, THF dry, 0° C., 70% over two steps; k) $NaBH_4$, MeOH dry, 0° C.; l) $LiBH_4$, MeOH, THF dry, 0° C., 77% over two steps.

Steps a-d) Preparation of methyl 7-keto-24-nor-LCA (13)

Compound 13 (660 mg, 1.69 mmol, 66% over four steps) was prepared from 7-KLCA in the same operative condition described in example 1B, steps a-d).

Steps e-h) Preparation of methyl 3α-acetoxy-6β-ethyl-7-keto-24-nor-5β-cholan-23-oate (15)

Compound 13 (660 mg, 1.69 mmol) was subjected to the same operative condition described in example 2A, steps b-d to obtain 603 mg of 14 (78% over three steps). NMR analysis demonstrated a diasteromeric ratio E/Z>95%. The E configuration at the exocyclic double bond was established by dipolar coupling $H_3$-25 (δ 1.67)/H-5 (δ 2.61) in Noesy spectrum (400 MHz, mixing time 400 ms).

(E)-3α-acetoxy-6-ethylidene-7-keto-24-nor-5β-cholan-23-oate (14): $C_{28}H_{42}O_5$ The $^1$H NMR was recorded on Varian Inova 400 MHz, using $CDCl_3$ as solvent: δ 6.17 (1H, q, J=7.2 Hz, H-24), 4.75 (1H, m, H-3), 3.64 (3H, s, $COOCH_3$), 2.61 (1H, dd, J=13.1, 4.0 Hz, H-5), 1.98 (3H, s, $COCH_3$), 1.67 (3H, d, J=7.2 Hz, $H_3$-25), 1.00 (3H, s, $H_3$-19), 0.97 (3H, d, J=6.8 Hz, $H_3$-21), 0.67 (3H, s, $H_3$-18).

The $^{13}$C NMR was recorded on Varian Inova 100 MHz, using $CDCl_3$ as solvent: δ 204.5, 174.2, 170.5, 143.0, 130.6, 72.5, 54.7, 51.4, 50.7, 48.6, 45.3, 43.7, 41.5, 39.1, 38.8, 34.6, 34.2, 33.6, 33.4, 28.5, 25.9 (2C), 22.8, 21.3 (2C), 19.7, 12.7, 12.1. Hydrogenation on $Pd(OH)_2$ in the same operative condition described in example 2A, step e, furnished 600 mg of 15 (quantitative yield).

The β configuration of ethyl group at C-6 was determined by dipolar couplings $H_3$-25 (δ 0.83)/$H_3$-19 (δ 1.22) in Noesy spectrum (400 MHz, mixing time 400 ms).

3α-acetoxy-6β-ethyl-7-keto-24-nor-5β-cholan-23-oate (15): $C_{28}H_{44}O_5$

The $^1$H NMR was recorded on Varian Inova 400 MHz, using $CDCl_3$ as solvent: δ 4.65 (1H, m, H-3), 3.67 (3H, s, $COOCH_3$), 2.60 (1H, t, J=11.2 Hz, H-8), 2.43 (1H, dd, J=14.2, 2.6 Hz, H-22a), 1.98 (3H, s, $COCH_3$), 1.88 (1H, m ovl, H-6), 1.22 (3H, s, $H_3$-19), 0.98 (3H, d, J=6.4 Hz, $H_3$-21), 0.83 (3H, t, J=7.0 Hz, $H_3$-25), 0.70 (3H, s, $H_3$-18).

The $^{13}$C NMR was recorded on Varian Inova 100 MHz, using $CDCl_3$ as solvent: δ 215.3, 174.0, 170.5, 72.8, 61.9, 55.0, 51.4, 49.2, 48.7, 45.5, 42.9, 42.6, 41.4, 38.7 (2C), 35.6, 35.3, 34.9, 28.3 (2C), 26.5, 25.9, 24.8, 21.4, 21.3, 19.6, 13.0, 12.1.

Steps i,j) Preparation of 6α-ethyl-3α, 7α-dihydroxy-24-nor-5β-cholan-23-ol (BAR502)

To a solution of compound 15 (450 mg, 1.0 mmol) and dry methanol (4 mL), MeONa (20 mL, 0.5 M in MeOH, 10 mmol) was added. After 24 h, $H_2O$ was added dropwise. Then after evaporation of the solvents, the residue was diluted with water and extracted with AcOEt (3×50 mL). The combined extract was washed with water, dried with $Na_2SO_4$, and evaporated to give 16 that was subjected to the step g without further purification.

Methyl 6α-ethyl-3α-hydroxy-7-keto-24-nor-5β-cholan-23-oate (16): $C_{26}H_{42}O_4$ The $^1$H NMR was recorded on Varian Inova 400 MHz, using $CDCl_3$ as solvent: δ 3.64 (3H, s, $COOCH_3$), 3.45 (1H, m, H-3), 2.83 (1H, q, J=7.3 Hz, H-6), 2.51 (1H, t, J=11.2 Hz, H-8), 2.45 (1H, dd, J=14.5, 3.2 Hz, H-22a), 1.26 (3H, s, $H_3$-19), 0.98 (3H, d, J=6.6 Hz, $H_3$-21), 0.81 (3H, t, J=7.0 Hz, $H_3$-25), 0.73 (3H, s, $H_3$-18).

The $^{13}$C NMR was recorded on Varian Inova 100 MHz, using $CDCl_3$ as solvent: δ 214.9, 175.4, 71.6, 56.2, 53.2, 52.0, 51.9, 51.0, 50.5, 45.2, 43.8, 42.2, 40.2, 36.7, 35.3, 34.8, 32.5, 30.5, 29.4, 25.6, 24.0, 22.9, 20.1, 20.0, 12.6, 12.4.

Compound 16 was subjected to $LiBH_4$ reduction in the same operative condition described in example 1A, step g. Silica gel chromatography eluting with hexane/EtOAc 6:4 afforded BAR502 (274 mg, 70% over two steps). An analytic sample was obtained by HPLC on a Nucleodur 100-5 C18 (5 μm; 4.6 mm i.d.×250 mm) with $MeOH/H_2O$ (88:12) as eluent (flow rate 1 mL/min, $t_R$=10.8 min).

BAR502: $C_{25}H_{44}O_3$

The $^1$H NMR was recorded on Varian Inova 400 MHz, using $CD_3OD$ as solvent: δ 3.65 (1H, s, H-7), 3.61 (1H, m, H-23a), 3.53 (1H, m, H-23b) 3.31 (1H, m, H-3), 0.97 (3H, d, J=6.6 Hz, $H_3$-21), 0.92 (3H, s, $H_3$-19), 0.91 (3H, t, J=7.0 Hz, $H_3$-25), 0.71 (3H, s, $H_3$-18).

The $^{13}$C NMR was recorded on Varian Inova 100 MHz, using $CD_3OD$ as solvent: δ 73.2, 71.1, 60.7, 57.7, 51.4, 46.9, 43.8, 42.9, 41.3, 40.9, 39.8, 36.7, 36.5, 34.6, 34.5, 34.2, 31.2, 29.4, 24.5, 23.7, 23.4, 21.8, 19.3, 12.1, 11.9.

Steps k,l). Preparation of 6β-ethyl-3α, 7β-dihydroxy-24-nor-5β-cholan-23-ol (BARn501) and 6β-ethyl-3α,7α-dihydroxy-24-nor-5β-cholan-23-ol (BARn504-6b)

Compound 15 (100 mg, 0.22 mmol) was subjected to the same operative condition described in example 2A, steps f-g. HPLC purification on a Nucleodur 100-5 C18 (5 μm; 10 mm i.d.×250 mm) with $MeOH/H_2O$ (86:14) as eluent (flow rate 3 mL/min), gave 47 mg of BARn501 (54%, $t_R$=11 min) and 20 mg of BARn504-6b (23%, $t_R$=15 min).

BARn501: $C_{25}H_{44}O_3$

The $^1$H NMR was recorded on Varian Inova 400 MHz, using $CD_3OD$ as solvent: δ 3.73 (1H, dd, J=10.5, 5.5 Hz, H-7), 3.61 (1H, m, H-23a), 3.51 (1H, m, ovl, H-23b), 3.51 (1H, m, ovl, H-3), 0.98 (3H, d, ovl, $H_3$-21), 0.97 (3H, s, $H_3$-19), 0.96 (3H, t, ovl, $H_3$-25), 0.70 (3H, s, $H_3$-18).

The $^{13}$C NMR was recorded on Varian Inova 100 MHz, using $CD_3OD$ as solvent: δ 75.2, 71.8, 60.8, 57.5, 56.6, 51.5, 45.5, 44.8, 42.0, 41.4, 40.7, 40.3, 39.9, 36.9, 36.0, 34.2, 30.5, 29.6, 28.3, 26.2, 23.4, 22.0, 19.4, 14.7, 12.9.

BARn504-6b: $C_{25}H_{44}O_3$

The $^1$H NMR was recorded on Varian Inova 400 MHz, using $CD_3OD$ as solvent: δ 3.63 (1H, m, H-23a), 3.60 (1H, m, H-7), 3.55 (1H, m, H-23b), 3.37 (1H, m, H-3), 2.30 (1H, q, J=12.5 Hz, H-4a), 0.97 (3H, d, J=6.6 Hz, $H_3$-21), 0.95 (3H, s, $H_3$-19), 0.95 (3H, t, J=7.0 Hz, $H_3$-25), 0.72 (3H, s, $H_3$-18).

The $^{13}$C NMR was recorded on Varian Inova 100 MHz, using $CD_3OD$ as solvent: δ 72.8, 72.7, 60.8, 57.9, 52.7, 51.4, 47.5, 43.7, 42.3, 41.0, 39.9, 37.5, 37.3, 36.7, 34.2, 33.3, 31.0, 29.6, 29.4, 26.2, 24.8, 21.6, 19.3, 14.5, 12.1.

Example 2D. Synthesis of 6-ethylidene-3α,7β-dihydroxy-5β-cholan-24-ol (BAR503), 6α-ethyl-3α,7β-dihydroxy-5β-cholan-24-ol (BAR501-6a), 6-ethylidene-3α,7β-dihydroxy-24-nor-5β-cholan-23-ol (BARn503) and 6α-ethyl-3α,7β-dihydroxy-24-nor-5β-cholan-23-ol (BARn501-6a)

Intermediate 11 was subjected to $NaBH_4$ reduction followed by treatment with $LiBH_4$. Alternatively $LiAlH_4$ treatment proceeded in a straightforward manner affording the concomitant reduction at C-24 and C-7. BAR503 was also used as starting material for BAR501-6a by hydrogenation on $Pd(OH)_2$ catalyst. The same synthetic protocol was performed on intermediate 14 producing the corresponding 23-derivatives, BARn503 and BARn501-6a.

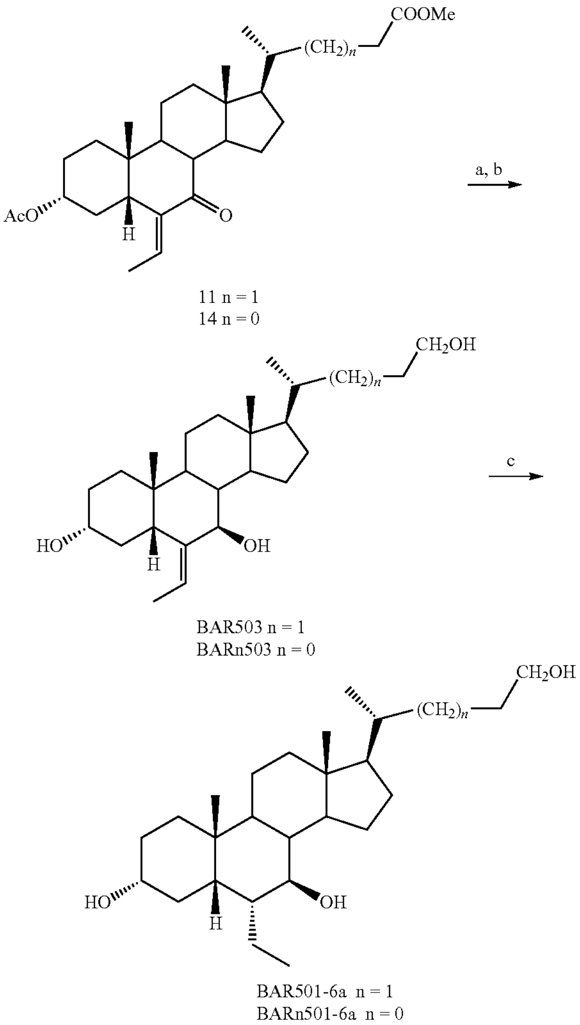

11 n = 1
14 n = 0

BAR503 n = 1
BARn503 n = 0

BAR501-6a n = 1
BARn501-6a n = 0 a) $NaBH_4$, MeOH; b) $LiBH_4$, MeOH dry, THF, 0° C, 85% over two steps; c) $H_2$, $Pd(OH)_2$, THF:MeOH 1:1 v/v.

Steps a,b). Preparation of 6-ethylidene-3α, 7β-dihydroxy-5β-cholan-24-ol (BAR503) and 6-ethylidene-3α,7β-dihydroxy-24-nor-5β-cholan-23-ol (BARn503)

Compound 11 (1 g, 2.11 mmol) was subjected to the same operative condition described in example 2A, steps f, g. HPLC purification on a Nucleodur 100-5 C18 (5 μm; 10 mm i.d.×250 mm) with $MeOH/H_2O$ (88:12) as eluent (flow rate 3 mL/min), gave 727 mg of BAR503 (85% over two steps, $t_R$=9.2 min). Alternatively $LiAlH_4$ treatment on 11 furnished BAR503.

BAR503: $C_{26}H_{44}O_3$

The $^1H$ NMR was recorded on Varian Inova 400 MHz, using $CD_3OD$ as solvent: δ 5.66 (1H, q, J=6.9 Hz, H-25), 3.90 (1H, d, J=9.8 Hz, H-7), 3.55 (1H, m, H-3), 3.50 (2H, m, $H_2$-24), 2.50 (1H, dd, J=4.0, 13.1 Hz, H-5), 1.62 (3H, d, J=6.9 Hz, $H_3$-26), 0.97 (3H, d, J=6.8 Hz, $H_3$-21), 0.81 (3H, s, $H_3$-19), 0.70 (3H, s, $H_3$-18).

The $^{13}C$ NMR was recorded on Varian Inova 100 MHz, using $CD_3OD$ as solvent: δ 142.7, 114.5, 73.4, 71.1, 63.6, 57.1, 56.1, 45.2, 44.9, 44.2, 40.7, 40.2, 36.3, 36.2, 35.9, 34.7, 32.4, 30.2, 29.5, 28.8, 27.4, 22.6, 21.5, 18.5, 11.8, 11.7.

The same synthetic protocol was performed on intermediate 14. HPLC purification on a Nucleodur 100-5 C18 (5 μm; 10 mm i.d.×250 mm) with $MeOH/H_2O$ (86:14) as eluent (flow rate 3 mL/min), gave BARn503 ($t_R$=8 min).

BARn503: $C_{25}H_{42}O_3$

The $^1H$ NMR was recorded on Varian Inova 400 MHz, using $CD_3OD$ as solvent: δ 5.66 (1H, q, J=6.8 Hz, H-24), 3.92 (1H, d, J=9.9 Hz, H-7), 3.60 (1H, m, H-23a), 3.56 (1H, m, H-3), 3.55 (1H, m, H-23b), 2.52 (1H, dd, J=3.7, 13.2 Hz, H-5), 1.63 (3H, d, J=6.8 Hz, $H_3$-25), 0.98 (3H, d, J=6.5 Hz, $H_3$-21), 0.95 (3H, s, $H_3$-19), 0.71 (3H, s, $H_3$-18).

The $^{13}C$ NMR was recorded on Varian Inova 100 MHz, using $CD_3OD$ as solvent: δ 143.7, 115.4, 74.1, 71.8, 60.8, 58.0, 57.1, 46.1, 45.9, 45.1, 41.6, 41.1, 39.9, 37.0, 36.4, 35.8, 34.1, 30.9, 29.8, 28.1, 23.5, 22.5, 19.5, 12.7, 12.6.

Step c). Preparation of 6α-ethyl-3α,7β-dihydroxy-5β-cholan-24-ol (BAR501-6a) and 6α-ethyl-3α,7β-dihydroxy-24-nor-5β-cholan-23-ol (BARn501-6a)

BAR503 (350 mg, 0.86 mmol) was subjected to the same operative condition described in example 2A step e, obtaining BAR501-6a in quantitative yield.

BAR501-6a: $C_{26}H_{46}O_3$

The $^1H$ NMR was recorded on Varian Inova 400 MHz, using $CD_3OD$ as solvent: δ 3.50 (2H, t, J=6.8 Hz, $H_3$-24), 3.44 (1H, m, H-3), 3.07 (1H, t, J=9.8 Hz, H-7), 0.96 (3H, d, J=6.8 Hz, $H_3$-21), 0.95 (3H, s, $H_3$-19), 0.86 (3H, t, J=7.4 Hz, $H_3$-26), 0.71 (3H, s, $H_3$-18).

The $^{13}C$ NMR was recorded on Varian Inova 100 MHz, using $CD_3OD$ as solvent: δ 76.5, 72.3, 63.6, 57.9, 57.3, 46.3, 45.0, 44.8, 41.8, 41.0, 39.9, 37.0, 36.4, 35.5, 33.3, 31.3, 31.0, 30.3, 29.8, 27.8, 24.3, 22.5, 22.0, 19.3, 12.8, 11.8.

BARn503 was subjected to the same operative condition described in example 2A step e, obtaining BARn501-6a in quantitative yield.

BARn501-6a: $C_{25}H_{44}O_3$

The $^1H$ NMR was recorded on Varian Inova 400 MHz, using $CD_3OD$ as solvent: δ 3.62 (1H, m, H-23a), 3.54 (1H, m, H-23b), 3.45 (1H, m, H-3), 3.08 (1H, t, J=9.8 Hz, H-7), 0.97 (3H, d, J=6.5 Hz, $H_3$-21), 0.95 (3H, s, $H_3$-19), 0.86 (3H, t, J=7.4 Hz, $H_3$-25), 0.73 (3H, s, $H_3$-18).

The $^{13}C$ NMR was recorded on Varian Inova 100 MHz, using $CD_3OD$ as solvent: δ 76.4, 72.5, 60.8, 57.9, 57.2, 46.2, 45.1, 44.7, 41.8, 41.2, 40.0, 39.8, 36.5, 35.6, 34.2, 31.2, 30.9, 29.9, 27.9, 24.1, 22.7, 22.0, 19.5, 12.7, 11.7.

Example 2E Synthesis of 6α-ethyl-3α,7α-dihydroxy-24-nor-5β-cholan-23-nitrile (BAR506)

7-KLCA was transformed in nitrile 17 following the same synthetic procedure described in Example 1B steps a-b. Alkylation followed by double bond reduction and epimerization at C-6 in the same operative condition described in example 2A steps c-d and example 2C step i, respectively furnished 18. $LiBH_4$ treatment as in example 2C step j afforded the desired 7a hydroxyl group in BAR506.

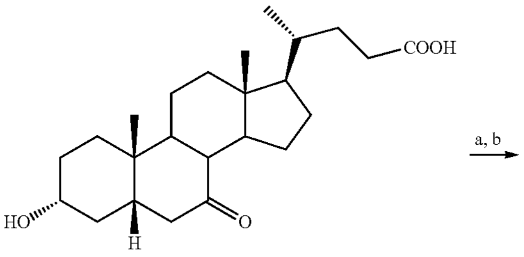

7-KLCA

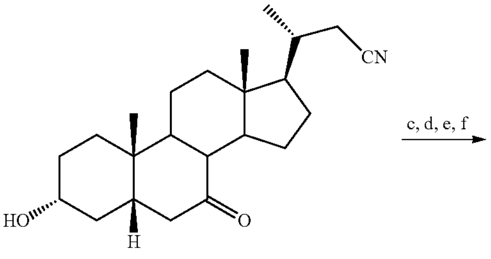

17

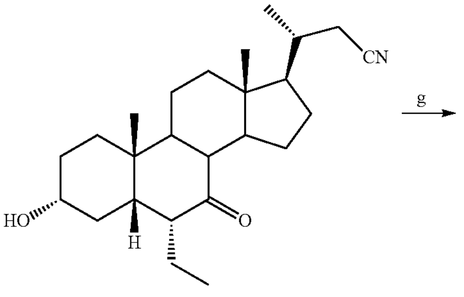

18

-continued

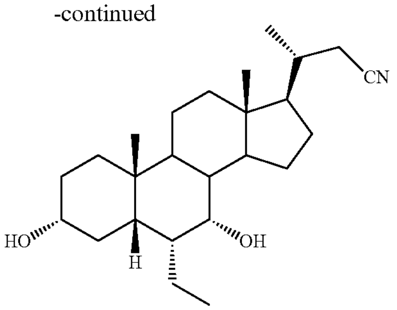

BAR506 a) HCOOH, $HClO_4$; b) TFA, trifluoroacetic anhydride, $NaNO_2$; c) DIPA, n-BuLi, TMSCl, TEA dry, THF dry -78° C.; d) acetaldehyde, $BF_3(OEt)_2$, $CHCl_2$, -60° C.; e) $H_2$, $Pd(OH)_2$, THF/MeOH 1:1; f) MeONa, MeOH; g) $LiBH_4$, MeOH, THF dry, 0° C.

BAR506: $C_{25}H_{41}NO_2$

The $^1H$ NMR was recorded on Varian Inova 700 MHz, using $CD_3OD$ as solvent: δ 3.66 (1H, br s, H-7), 3.31 (1H, ovl, H-3), 2.46 (1H, dd, J=3.8, 16.9 Hz, H-22a), 2.34 (1H, dd, J=7.4, 16.9 Hz, H-22b), 1.16 (3H, d, J=6.5 Hz, $H_3$-21), 0.91 (3H, t, J=7.5 Hz, $H_3$-25), 0.92 (3H, s, $H_3$-19), 0.73 (3H, s, $H_3$-18).

The $^{13}C$ NMR was recorded on Varian Inova 175 MHz, using $CD_3OD$ as solvent: δ 120.3, 72.9, 70.9, 56.1, 51.5, 46.7, 43.4, 42.9, 41.4, 40.2, 36.5, 36.2, 34.3 (2C), 34.2, 30.7, 29.2, 24.9, 24.4, 23.4, 23.3, 21.9, 18.5, 12.1, 11.6.

Example 2F. Synthesis of 6α-ethyl-7α-hydroxy-5β-cholan-24-ol (BAR701), 6α-ethyl-7α-hydroxy-5β-cholan-24-yl 24-sodium sulfate (BAR701solf), 6β-ethyl-7β-hydroxy-5β-cholan-24-ol (BAR702), 6α-ethyl-7β-hydroxy-5β-cholan-24-ol (BAR703), 6α-ethyl-7α-hydroxy-5β-cholan-24-oic acid (BAR704), 6α-ethyl-7α-hydroxy-5β-cholan-24-oyl taurine sodium sulfate (BART704), 6β-ethyl-7α-hydroxy-5β-cholan-24-ol (BAR705) and 6α-ethyl-7β-hydroxy-5β-cholan-24-oic acid (BAR711)

Compound 12 was treated with MeONa in methanol to obtain deacetylation at C-3 and inversion at C-6. Tosylation, elimination and hydrogenation of the double bound on ring A gave 20. Hydrolysis at methyl ester function followed by $LiBH_4$ treatment furnished BAR704 in high chemical yield. Intermediate 20 was also used as starting material for BAR701. Sulfation on C-24 on a small aliquot of BAR701 furnished BAR701solf.

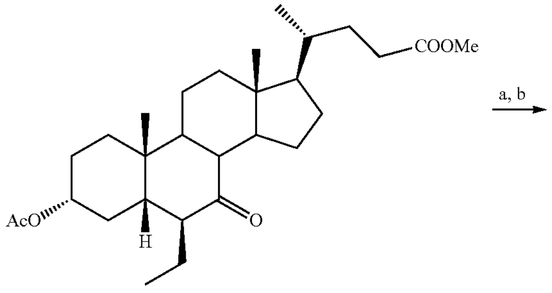

12

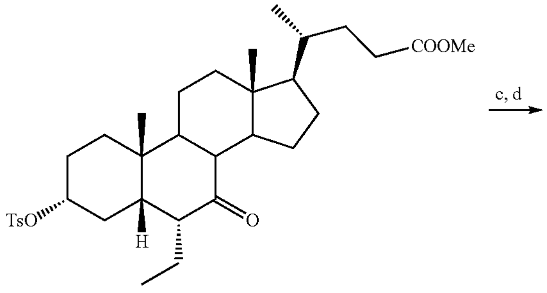

19

-continued

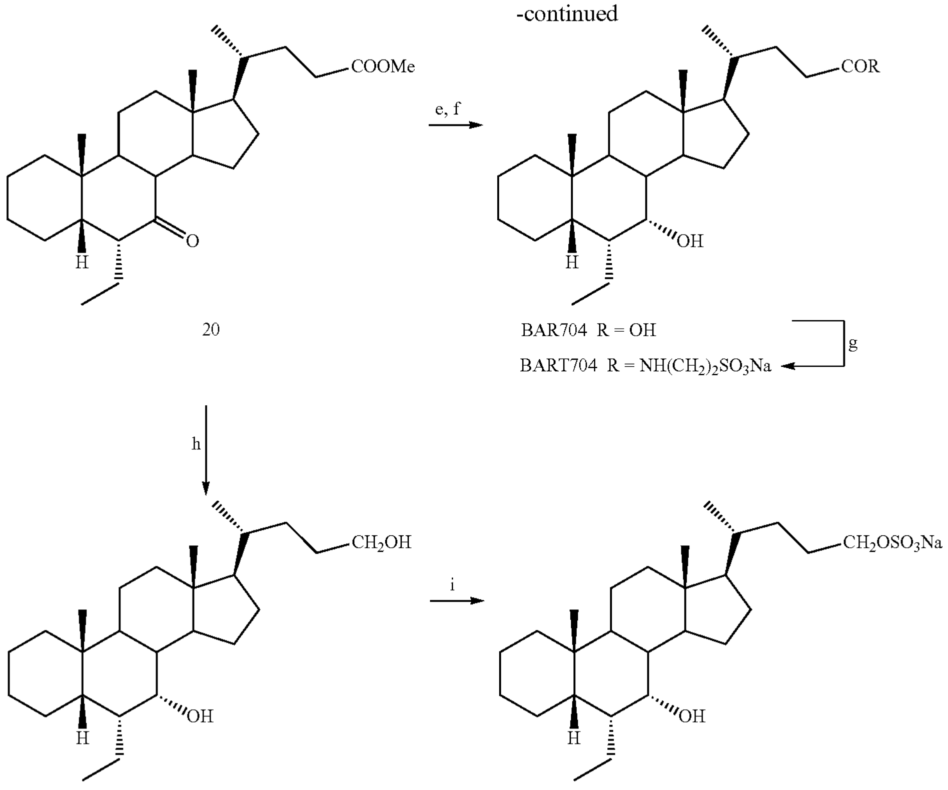

20

BAR704 R = OH

BART704 R = $NH(CH_2)_2SO_3Na$

BAR701

BAR701solf a) MeONa, MeOH; b) p-TsCl, pyridine, quantitative yield over two steps; c) LiBr, $Li_2CO_3$, DMF, reflux, d) $H_2$, $Pd(OH)_2$, THF/MeOH 1:1, room temperature, 88% over two steps; e) NaOH, $MeOH:H_2O$ 1:1 v/v, 82%; f) $LiBH_4$, MeOH dry, THF, 0° C., 83%; g) DMT—MM, $Et_3N$, taurine, DMF dry; h) $LiBH_4$, MeOH dry, THF, 0° C., 77%; i) $Et_3N{\bullet}SO_3$, DMF, 95° C.

Steps a-f) Preparation of 6α-ethyl-7α-hydroxy-5β-cholan-24-oic acid (BAR704)

Compound 12 (500 mg, 1.05 mmol) was treated with MeONa (2.1 mL, 0.5 M in MeOH, 1.05 mmol) in MeOH (5 mL) overnight in the same operative condition of Example 2C step i. Tosylation on the crude reaction product in the same operative condition of Example 1C, step a, furnished 19 (620 mg, quantitative yield over two steps). Intermediate 19 (500 mg, 0.85 mmol) was subjected to the same operative condition of Example 1C, steps b,c, to obtain 312 mg of 20 (88% over two steps). Compound 20 (200 mg, 0.48 mmol) was hydrolyzed with NaOH (96 mg, 2.4 mmol) in a solution of $MeOH:H_2O$ 1:1 v/v (10 mL) in the same operative condition of Example 1A step f. Crude carboxylic acid intermediate (190 mg, 0.47 mmol) was treated with $LiBH_4$ (1.65 mL, 2 M in THF, 3.3 mmol) and MeOH (133 μL, 3.3 mmol) in THF dry (5 mL). Purification by silica gel ($CH_2Cl_2$-MeOH 99:1) furnished 157 mg of BAR704 (83%). In same embodiments $LiBH_4$ treatment after alkaline hydrolysis produced small amounts (about 10%) of 6α-ethyl-7β-hydroxy-5β-cholan-24-oic acid (BAR711) that was isolated by HPLC purification on a Nucleodur 100-5 C18 (5 μm; 10 mm i.d.x250 mm) with $MeOH/H_2O$ (88:12) as eluent (flow rate 3 mL/min, $t_R$=16 min).

BAR704: $C_{26}H_{44}O_3$

The $^1H$ NMR was recorded on Varian Inova 400 MHz, using $CD_3OD$ as solvent: δ 3.65 (1H, br s, H-7), 2.34 (1H, m, H-23a), 2.20 (1H, m, H-23b), 0.96 (3H, d, J=6.3 Hz, $H_3$-21), 0.92 (3H, s, $H_3$-19), 0.89 (3H, t, J=7.4 Hz, $H_3$-26), 0.70 (3H, s, $H_3$-18).

The $^{13}C$ NMR was recorded on Varian Inova 100 MHz, using $CD_3OD$ as solvent: δ 178.0, 71.6, 57.4, 51.7, 48.7, 43.8, 43.3, 41.5, 41.1, 39.3, 37.4, 36.8, 34.6, 32.5 (2C), 29.3, 28.8, 25.1, 24.6 (2C), 23.5, 22.5, 22.0, 18.8, 12.2, 12.1.

BAR711: $C_{26}H_{44}O_3$

The $^1H$ NMR was recorded on Varian Inova 500 MHz, using $CD_3OD$ as solvent: δ 3.08 (1H, t, J=9.6 Hz, H-7), 2.32 (1H, m, H-23a), 2.20 (1H, m, H-23b), 0.96 (3H, d, J=6.2 Hz, $H_3$-21), 0.95 (3H, s, $H_3$-19), 0.85 (3H, t, J=7.0 Hz, $H_3$-26), 0.70 (3H, s, $H_3$-18).

Step g) Preparation of 6α-ethyl-7α-hydroxy-5β-cholan-24-oyl taurine sodium sulfate (BART704)

An aliquot of BAR704 (10 mg, 0.024 mmol) in DMF dry (5 mL) was treated with DMT-MM (20.5 mg, 0.07 mmol) and triethylamine (83 μL, 0.6 mmol) and the mixture was stirred at room temperature for 10 min. Then to the mixture was added taurine (18 mg, 0.14 mmol). After 3 h, the reaction mixture was concentrated under vacuo and dissolved in water (5 mL). Purification on C18 silica gel column and then HPLC on a Nucleodur 100-5 C18 (5 μm; 10 mm i.d.x250 mm) with $MeOH/H_2O$ (83:17) as eluent (flow rate 3 mL/min), gave 4.5 mg BART704 ($t_R$=10 min).

BART704: $C_{28}H_{48}NNaO_5S$

The $^1H$ NMR was recorded on Varian Inova 400 MHz, using $CD_3OD$ as solvent: δ 3.65 (1H, br s, H-7), 3.58 (2H, t, J=7.0 Hz, $CH_2$—N), 2.96 (2H, t, J=9.6 Hz, $CH_2$—S), 2.25

(1H, m, H-23a), 2.10 (1H, m, H-23b), 0.97 (3H, d, J=6.4 Hz, $H_3$-21), 0.92 (3H, s, $H_3$-19), 0.89 (3H, t, J=7.1 Hz, $H_3$-26), 0.70 (3H, s, $H_3$-18).

Step h) Preparation of 6α-ethyl-7α-hydroxy-5β-cholan-24-ol (BAR701)

Compound 20 (100 mg, 0.24 mmol) was treated in the same operative condition of Example 2C step j. HPLC purification on a Nucleodur 100-5 C18 (5 μm; 10 mm i.d.×250 mm) with MeOH/$H_2O$ (92:8) as eluent (flow rate 3 mL/min), gave 64 mg of BAR701 ($t_R$=31 min) and a small amount of 6α-ethyl-7β-hydroxy-5β-cholan-24-ol (BAR703) (8 mg, $t_R$=24.8 min).

BAR701: $C_{26}H_{46}O_2$

The $^1$H NMR was recorded on Varian Inova 400 MHz, using $CD_3OD$ as solvent: δ 3.65 (1H, br s, H-7), 3.51 (2H, m, $H_2$-24), 0.97 (3H, d, J=6.3 Hz, $H_3$-21), 0.92 (3H, s, $H_3$-19), 0.89 (3H, t, J=7.3 Hz, $H_3$-26), 0.71 (3H, s, $H_3$-18).

The $^{13}$C NMR was recorded on Varian Inova 100 MHz, using $CD_3OD$ as solvent: δ 71.6, 63.6, 57.6, 51.8, 48.7, 43.7, 43.3, 41.5, 41.1, 39.3, 37.5, 37.0, 34.6, 33.2, 30.3, 29.4, 28.8, 25.1, 24.6 (2C), 23.5, 22.5, 22.0, 19.2, 12.3, 12.1.

BAR703 $C_{26}H_{46}O_2$

The $^1$H NMR was recorded on Varian Inova 500 MHz, using $CD_3OD$ as solvent: δ 3.51 (2H, m, $H_2$-24), 3.07 (1H, t, J=10.0 Hz, H-7), 0.96 (3H, d, J=6.6 Hz, $H_3$-21), 0.84 (3H, t, J=7.0 Hz, $H_3$-26), 0.95 (3H, s, $H_3$-19), 0.71 (3H, s, $H_3$-18).

The $^{13}$C NMR was recorded on Varian Inova 100 MHz, using $CD_3OD$ as solvent: δ 76.3, 63.6, 57.9, 56.8, 46.3, 45.3, 45.0, 44.7, 41.7, 41.1, 38.8, 37.0, 36.3, 33.3, 30.3, 28.1, 27.9 (2C), 25.0 (2C), 22.0, 21.9 (2C), 19.4, 12.7, 11.6.

Step i) Preparation of 6α-ethyl-7α-hydroxy-5β-cholan-24-yl 24-sodium sulfate (BAR701solf)

Sulfation on C-24 on a small aliquot of BAR701 was performed in the same operative conditions described in example 1B step g) to give crude BAR701solf as ammonium salt. RP18/HPLC on a Nucleodur 100-5 C18 (5 μm; 10 mm i.d.×250 mm) with MeOH/$H_2O$ (82:18) as eluent (flow rate 3 mL/min) afforded BAR701solf ($t_R$=14.2 min) as sodium salt.

BAR701solf: $C_{26}H_{45}NaO_5S$

The $^1$H NMR was recorded on Varian Inova 400 MHz, using $CD_3OD$ as solvent: δ 3.96 (2H, t, J=6.3 Hz, $H_2$-24), 3.64 (1H, br s, H-7), 0.96 (3H, d, J=6.6 Hz, $H_3$-21), 0.91 (3H, s, $H_3$-19), 0.88 (3H, t, J=7.4 Hz, $H_3$-26), 0.69 (3H, s, $H_3$-18).

Preparation of 6β-ethyl-7β-hydroxy-5β-cholan-24-ol (BAR702) and 6β-ethyl-7α-hydroxy-5β-cholan-24-ol (BAR705)

Compound 12 (500 mg, 1.05 mmol) was treated with MeONa (2.1 mL, 0.5 M in MeOH, 1.05 mmol) in MeOH (10 mL) in the same operative condition of Example 2C, step i, except for reaction time (2 h). Tosylation on the crude reaction product in the same operative condition of Example 1C, step a, furnished 21 (620 mg, quantitative yield over two steps). Intermediate 21 (600 mg, 1.02 mmol) was subjected to the same operative condition of Example 1C, steps b,c, to obtain 400 mg of 22 (94%). Compound 22 (350 mg, 0.84 mmol) was reduced with $NaBH_4$/$LiBH_4$ in the same operative condition of Example 2A steps f,g. HPLC purification on a Nucleodur 100-5 C18 (5 μm; 10 mm i.d.×250 mm) with MeOH/$H_2O$ (92:8) as eluent (flow rate 3 mL/min), furnished 180 mg of BAR702 ($t_R$=25 min) and 75.4 mg of BAR705 ($t_R$=13 min). Alternatively step e was performed with $Ca(BH_4)_2$, produced in situ.

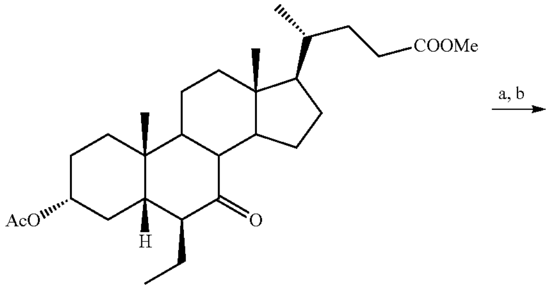

12

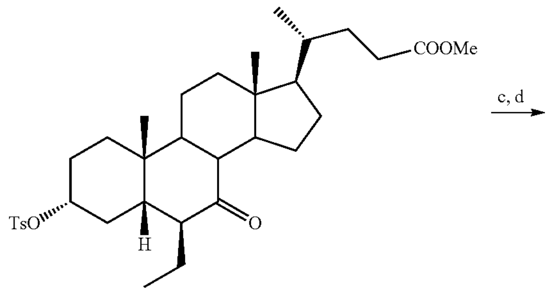

21

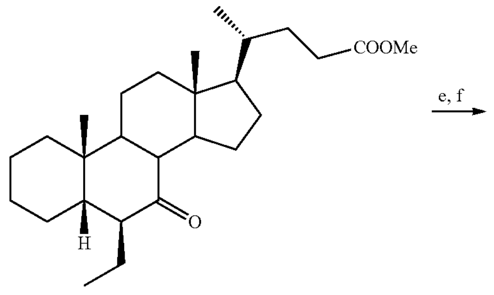

22

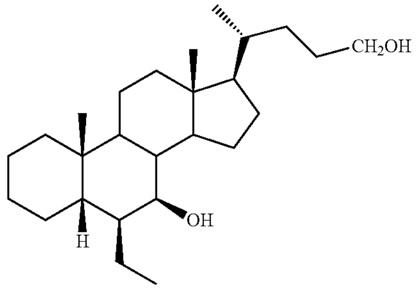

BAR702

-continued

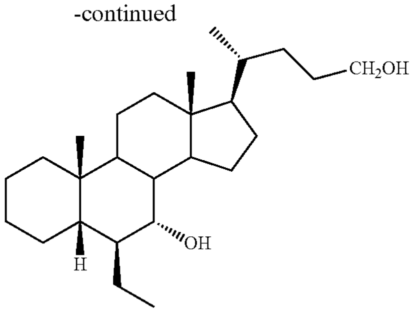

BAR705 a) MeONa, MeOH; b) p-TsCl, pyridine, quantitative yield over two steps; c) LiBr, $Li_2CO_3$, DMF, reflux; d) $H_2$, $Pd(OH)_2$, THF/MeOH 1:1, room temperature, 94% over two steps; e) $NaBH_4$, MeOH; f) $LiBH_4$, MeOH dry, THF, 0° C., 78% over two steps.

BAR702: $C_{26}H_{46}O_2$

The $^1H$ NMR was recorded on Varian Inova 700 MHz, using $CD_3OD$ as solvent: δ 3.67 (1H, dd, J=8.7, 4.7 Hz, H-7), 3.51 (2H, m, $H_2$-24), 0.98 (3H, s, $H_3$-19), 0.97 (3H, d, J=6.6 Hz, $H_3$-21), 0.96 (3H, t, J=7.4 Hz, $H_3$-26), 0.71 (3H, s, $H_3$-18).

The $^{13}C$ NMR was recorded on Varian Inova 175 MHz, using $CD_3OD$ as solvent: δ 75.5, 63.8, 57.6, 56.5, 44.2, 43.7, 42.8, 41.0, 40.9, 40.8, 38.2 (2C), 36.9, 34.4, 32.8, 29.7, 28.9, 27.0, 26.1, 24.7, 22.2, 22.0 (2C), 19.2, 13.9, 12.3.

BAR705: $C_{26}H_{46}O_2$

The $^1H$ NMR was recorded on Varian Inova 700 MHz, using $CD_3OD$ as solvent: δ 3.59 (1H, br s, H-7), 3.51 (2H, m, $H_2$-24), 2.23 (1H, dq, J=13.9, 4.0 Hz, H-4a), 0.97 (3H, d, J=6.6, $H_3$-21), 0.95 (3H, t, J=7.1 Hz, $H_3$-26), 0.94 (3H, s, $H_3$-19), 0.70 (3H, s, $H_3$-18).

The $^{13}C$ NMR was recorded on Varian Inova 175 MHz, using $CD_3OD$ as solvent: δ 73.1, 63.2, 57.3, 52.8, 51.4, 49.4, 43.8, 41.3, 39.7, 37.4 (2C), 37.2, 34.2, 32.6 (2C), 29.9, 29.5, 28.9, 28.3, 27.3, 24.5, 21.7, 21.2, 18.8, 14.3, 12.3.

Example 2G. Synthesis of 6α-ethyl-3β,7α-dihydroxy-5β-cholan-24-oic acid (BAR710), 6α-ethyl-3β,7α-dihydroxy-5β-cholan-24-oyl taurine sodium sulfate (BART710), 6α-ethyl-3β,7α-dihydroxy-5β-cholan-24-ol (BAR706), 6α-ethyl-3β,7α-dihydroxy-5β-cholan-24-yl 24-sodium sulfate (BAR706solf), 6α-ethyl-3β,7β-dihydroxy-5β-cholan-24-ol (BAR707), 6β-ethyl-3β,7β-dihydroxy-5β-(BAR708) and 6β-ethyl-3β,7α-dihydroxy-5β-cholan-24-ol (BAR709) and 6α-ethyl-3β,7β-dihydroxy-5β-cholan-24-oic acid (BAR712)

In a convergent protocol inversion at C-3 on derivative 19 followed by treatment with MeONa/MeOH gave 23 that was used as starting material in the synthesis of BAR706, BAR706solf, BAR710 and BART710. Inversion at C-3 followed by reduction at C-7 and C-24, produced BAR708 and BAR709.

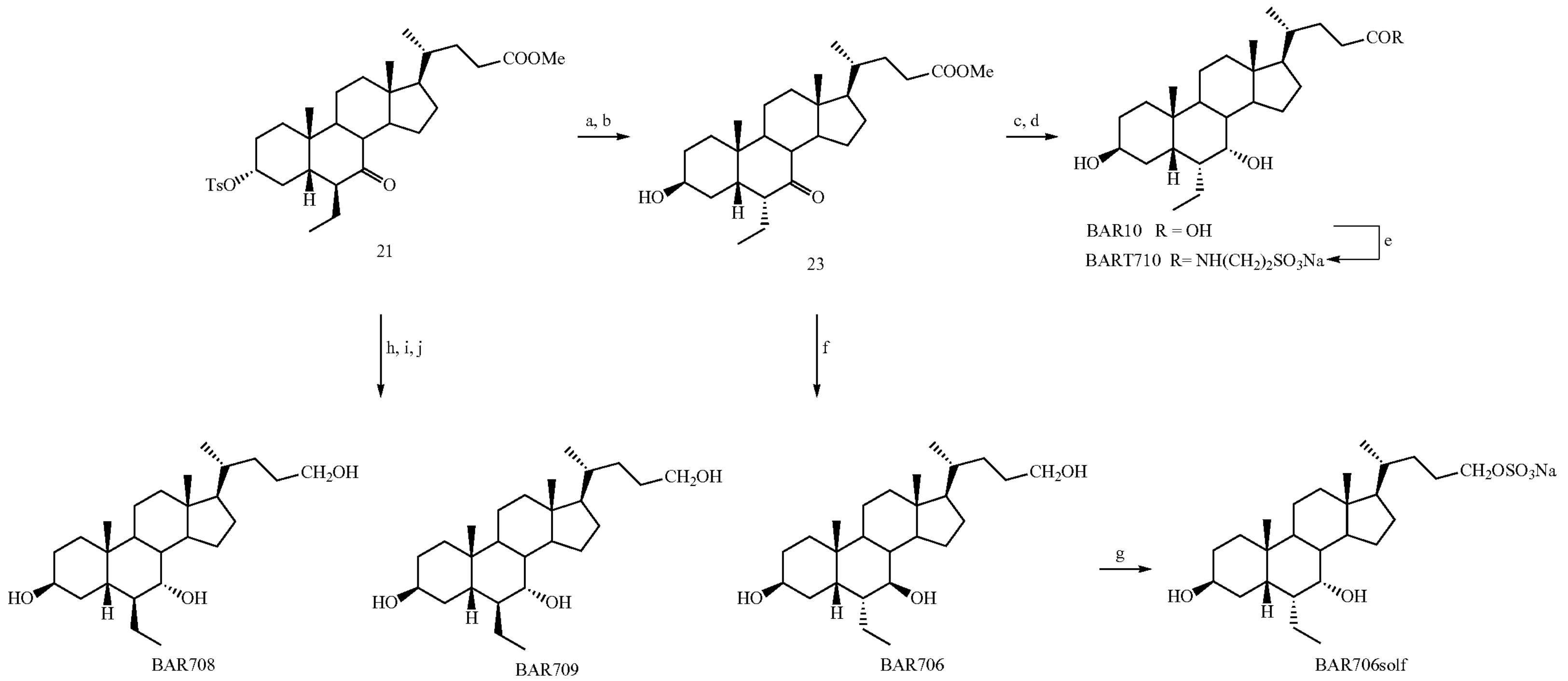
21
23
BAR10 R = OH
BART710 R= $NH(CH_2)_2SO_3Na$
BAR708
BAR709
BAR706
BAR706solf
a) $CH_3COOK$, $DMF:H_2O$ 5:1 v/v; b) NaOMe, MeOH, 74% over two steps; c) NaOH, $MeOH:H_2O$ 1:1 v/v; d) $LiBH_4$, MeOH dry, THF, 0° C., 65% over two steps; e) DMT—MM, $Et_3N$, taurine, DMF dry; f) $LiBH_4$, MeOH dry, THF, 0° C., 58%; g) $Et_3N{\bullet}SO_3$, DMF, 95° C.; h) $CH_3COOK$, $DMF:H_2O$ 5:1; i) $NaBH_4$, MeOH; j) $LiBH_4$, MeOH dry, THF, 0° C., 74% over three steps.

Steps a-d) Preparation of 6α-ethyl-3β,7α-dihydroxy-5β-cholan-24-oic acid (BAR710)

A solution of 21 (600 mg, 1.0 mmol) and $CH_3COOK$ (98 mg, 1.0 mmol) dissolved in water (2 mL) and N,N'-dimethylformamide (DMF, 10 mL) was refluxed for 2 h. The solution was cooled at room temperature and then ethyl acetate and water were added. The separated aqueous phase was extracted with ethyl acetate (3×30 mL). The combined organic phases were washed with water, dried ($Na_2SO_4$) and evaporated to dryness to give 600 mg of mixture. Purification by silica gel (hexane-ethyl acetate 8:2 and 0.5% TEA) gave 350 mg of oleos oil. C-6 inversion in the same operative condition as described in Example 2C step i, furnished 23 (320 mg, 74% over two steps) that was subjected to hydrolysis followed to $LiBH_4$ treatment as described in Example 2F, steps e,f. HPLC purification on a Nucleodur 100-5 C18 (5 μm; 10 mm i.d.×250 mm) with $MeOH/H_2O$ (88:12) as eluent (flow rate 3 mL/min), gave 208 mg of BAR710 (65%, $t_R$=11 min). Alternatively inversion at C-3 on 21 followed by alkaline hydrolysis and then $LiBH_4$ treatment afforded BAR710 in a straightforward manner.

In same embodiments $LiBH_4$ treatment after alkaline hydrolysis produced small amounts (about 10%) of 6α-ethyl-3β,7β-dihydroxy-5β-cholan-24-oic acid (BAR712) that was isolated by HPLC purification on a Nucleodur 100-5 C18 (5 μm; 10 mm i.d.×250 mm) with $MeOH/H_2O$ (88:12) as eluent (flow rate 3 mL/min, $t_R$=8 min)

BAR710: $C_{26}H_{44}O_4$

The $^1H$ NMR was recorded on Varian Inova 400 MHz, using $CD_3OD$ as solvent: δ 3.97 (1H, br s, H-3), 3.67 (1H, br s, H-7), 2.33 (1H, m, H-23a), 2.21 (1H, m, H-23b), 0.96 (3H, d, J=6.5 Hz, $H_3$-21), 0.94 (3H, s, $H_3$-19), 0.91 (3H, t, J=7.6 Hz, $H_3$-26), 0.70 (3H, s, $H_3$-18).

The $^{13}C$ NMR was recorded on Varian Inova 100 MHz, using $CD_3OD$ as solvent: δ 178.3, 71.3, 67.5, 57.4, 51.7, 43.8, 42.8, 41.5, 41.2, 41.0, 37.0, 36.7, 33.8, 32.4, 32.0, 31.1 (2C), 29.3, 28.3, 24.6, 24.2, 23.3, 22.2, 18.8, 12.3, 12.2.

BAR712: $C_{26}H_{44}O_4$

The $^1H$ NMR was recorded on Varian Inova 500 MHz, using $CD_3OD$ as solvent: δ 4.01 (1H, br s, H-3), 3.06 (1H, t, J=9.7 Hz, H-7), 2.32 (1H, m, H-23a), 2.19 (1H, m, H-23b), 0.97 (3H, s, $H_3$-19), 0.96 (3H, d, ovl, $H_3$-21), 0.87 (3H, t, J=7.7 Hz, $H_3$-26), 0.71 (3H, s, $H_3$-18).

Step e) Preparation of 6α-ethyl-3β,7α-dihydroxy-5β-cholan-24-oyl taurine sodium sulfate (BART710)

An aliquot of BAR710 (10 mg) was treated in the same operative condition of Example 2F step g.

BART710: $C_{28}H_{48}NNaO_6S$

The $^1H$ NMR was recorded on Varian Inova 500 MHz, using $CD_3OD$ as solvent: δ 3.97 (1H, br s, H-3), 3.67 (1H, br s, H-7), 3.59 (2H, t, J=6.8 Hz, $CH_2$—N), 2.96 (2H, t, J=6.8 Hz, $CH_2$—S), 0.97 (3H, d, J=6.4 Hz, $H_3$-21), 0.95 (3H, s, $H_3$-19), 0.91 (3H, t, J=7.1 Hz, $H_3$-26), 0.70 (3H, s, $H_3$-18).

Steps f) Preparation of 6α-ethyl-3β,7α-dihydroxy-5β-cholan-24-ol (BAR706) and 6α-ethyl-3β,7β-dihydroxy-5β-cholan-24-ol (BAR707)

Intermediate 23 (500 mg, 1.16 mmol) was treated with $LiBH_4$ (4 mL, 8.1 mmol) and MeOH (327 μL, 8.1 mmol) in THF dry (10 mL) as described in Example 2C, step j. HPLC purification on a Nucleodur 100-5 C18 (5 μm; 10 mm i.d.×250 mm) with $MeOH/H_2O$ (88:12) as eluent (flow rate 3 mL/min), gave BAR706 (250 mg, $t_R$=12.6 min) and a small amount of 6α-ethyl-3β,7β-dihydroxy-5β-cholan-24-ol (BAR707) (23 mg, $t_R$=8.2 min).

BAR706: $C_{26}H_{46}O_3$

The $^1H$ NMR was recorded on Varian Inova 500 MHz, using $CD_3OD$ as solvent: δ 3.97 (1H, br s, H-3), 3.66 (1H, br s, H-7), 3.51 (2H, m, $H_2$-24), 0.96 (3H, d, J=6.6 Hz, $H_3$-21), 0.94 (3H, s, $H_3$-19), 0.91 (3H, t, J=7.5 Hz, $H_3$-26), 0.70 (3H, s, $H_3$-18).

The $^{13}C$ NMR was recorded on Varian Inova 125 MHz, using $CD_3OD$ as solvent: δ 71.4, 67.4, 63.6, 57.6, 51.7, 43.7, 42.8, 41.5, 41.2, 41.1, 37.1 (2C), 33.8, 33.2, 31.3 (2C), 30.3, 29.4, 28.3, 24.6, 24.2, 23.3, 22.3, 19.2, 12.7, 12.1.

BAR707: $C_{26}H_{46}O_3$

The $^1H$ NMR was recorded on Varian Inova 500 MHz, using $CD_3OD$ as solvent: δ 4.01 (1H, br s, H-3), 3.51 (2H, m, $H_2$-24), 3.05 (1H, t, J=9.7 Hz, H-7), 0.97 (3H, s, $H_3$-19), 0.96 (3H, d, J=6.4 Hz, $H_3$-21), 0.88 (3H, t, J=7.6 Hz, $H_3$-26), 0.72 (3H, s, $H_3$-18).

The $^{13}C$ NMR was recorded on Varian Inova 100 MHz, using $CD_3OD$ as solvent: δ 76.3, 67.1, 63.6, 57.8, 56.8, 45.0, 44.8, 44.5, 41.7, 40.3, 39.1, 37.0, 35.9, 33.0, 31.2, 30.2, 29.8, 28.4, 28.0, 27.9, 24.8, 22.9, 21.8, 19.3, 12.8, 11.6.

Step g) Preparation of 6α-ethyl-3β,7α-dihydroxy-5β-cholan-24-yl 24-sodium sulfate (BAR706solf)

Sulfation on C-24 on a small aliquot of BAR706 was performed in the same operative conditions described in example 1B step g.

BAR706solf: $C_{26}H_{45}NaO_6S$

The $^1H$ NMR was recorded on Varian Inova 500 MHz, using $CD_3OD$ as solvent: δ 3.97 (1H, br s ovl, H-3), 3.96 (2H, t ovl, $H_2$-24), 3.65 (1H, br s, H-7), 0.96 (3H, d, J=6.6 Hz, $H_3$-21), 0.94 (3H, s, $H_3$-19), 0.90 (3H, t, J=7.5 Hz, $H_3$-26), 0.70 (3H, s, $H_3$-18).

Steps h,i,j) Preparation of 6β-ethyl-3β,7β-dihydroxy-5β-cholan-24-ol (BAR708) and 6β-ethyl-3β,7α-dihydroxy-5β-cholan-24-ol (BAR709)

Compound 19 was treated in the same operative condition of step a. $NaBH_4/LiBH_4$ reduction of 100 mg (0.23 mmol) in the same operative conditions of Example 2A, steps f,g, afforded a mixture whose HPLC purification (88% MeOH:$H_2O$) gave pure 6β-ethyl-3β,7β-dihydroxy-5β-cholan-24-ol (BAR708) (48.3 mg, $t_R$=11 min) and 6β-ethyl-3β,7α-dihydroxy-5β-cholan-24-ol (BAR709) (20.7 mg, $t_R$=13 min). Alternatively step i was performed with $Ca(BH_4)_2$, produced in situ.

BAR708: $C_{26}H_{46}O_3$

The $^1H$ NMR was recorded on Varian Inova 700 MHz, using $CD_3OD$ as solvent: δ 3.59 (1H, br s, H-3), 3.57 (1H, dd, J=12.6, 2.3 Hz, H-7), 3.51 (2H, m, $H_2$-24), 0.98 (3H, s, $H_3$-19), 0.96 (3H, ovl, $H_3$-21), 0.96 (3H, t, ovl, $H_3$-26), 0.70 (3H, s, $H_3$-18).

The $^{13}C$ NMR was recorded on Varian Inova 175 MHz, using $CD_3OD$ as solvent: δ□ 75.2, 68.3, 63.6, 58.3, 57.1, 45.7 (2C), 44.2, 41.8 (2C), 41.2, 40.0, 37.0, 35.9, 33.3, 31.1, 30.3, 29.4 (2C), 26.6 (2C), 23.2 (2C), 19.3, 13.0, 12.3.

BAR709: $C_{26}H_{46}O_3$

The $^1H$ NMR was recorded on Varian Inova 700 MHz, using $CD_3OD$ as solvent: δ 3.91 (1H, br s, H-3), 3.60 (1H, br s, H-7), 3.51 (2H, m, $H_2$-24), 2.45 (1H, t, J=13.3 Hz, H-4a), 0.97 (3H, s, $H_3$-19), 0.97 (3H, ovl, $H_3$-21), 0.95 (3H, t, J=7.4 Hz, $H_3$-26), 0.71 (3H, s, $H_3$-18).

The $^{13}C$ NMR was recorded on Varian Inova 175 MHz, using $CD_3OD$ as solvent: δ 72.8, 67.4, 63.4, 57.2, 51.3, 51.2, 43.2, 41.6, 40.5, 37.3, 37.1 (2C), 36.9, 34.0, 33.3, 32.1, 30.3, 29.3, 28.9, 28.6, 26.3, 24.9, 22.0, 19.3, 13.8, 12.1.

Example 2H. Synthesis of 6α-ethyl-7α-hydroxy-24-nor-5β-cholan-23-oic acid (BARn704), 6α-ethyl-7α-hydroxy-24-nor-5β-cholan-23-oyl taurine sodium sulfate (BARTn704), 6α-ethyl-7α-hydroxy-24-nor-5β-cholan-23-ol (BARn701) and 6α-ethyl-7α-hydroxy-24-nor-5β-cholan-23-yl 23-sodium sulfate (BARn701solf)

BARn704, BARTn704, BARn701 and BARn701solf were prepared starting from 15 and following the same synthetic protocol described for their C24 homologues (Example 2F, steps a-i).

BARn704: $C_{25}H_{42}O_3$

The $^1H$ NMR was recorded on Varian Inova 400 MHz, using $CD_3OD$ as solvent: δ 3.64 (1H, br s, H-7), 2.41 (1H, dd, J=11.0, 2.6 Hz, H-22a), 1.00 (3H, d, J=6.0 Hz, $H_3$-21), 0.90 (3H, s, $H_3$-19), 0.87 (3H, t, J=7.4 Hz, $H_3$-25), 0.71 (3H, s, $H_3$-18).

The $^{13}C$ NMR was recorded on Varian Inova 100 MHz, using $CD_3OD$ as solvent: δ 178.9, 71.6, 57.5, 51.7, 48.6, 43.8, 43.4, 43.3, 41.5, 40.9, 39.1, 37.4, 35.2, 34.6, 29.4, 28.8, 25.0, 24.6 (2C), 23.5, 22.4, 22.0, 20.1, 12.2, 12.1.

BARTn704: $C_{27}H_{46}NNaO_5S$

The $^1H$ NMR was recorded on Varian Inova 400 MHz, using $CD_3OD$ as solvent: δ 3.64 (1H, br s, H-7), 3.59 (2H, t, J=6.8 Hz, $CH_2$—N), 2.96 (2H, t, J=6.8 Hz, $CH_2$—S), 2.40 (1H, dd, J=11.0, 2.8 Hz, H-22a), 1.00 (3H, d, J=6.0 Hz,

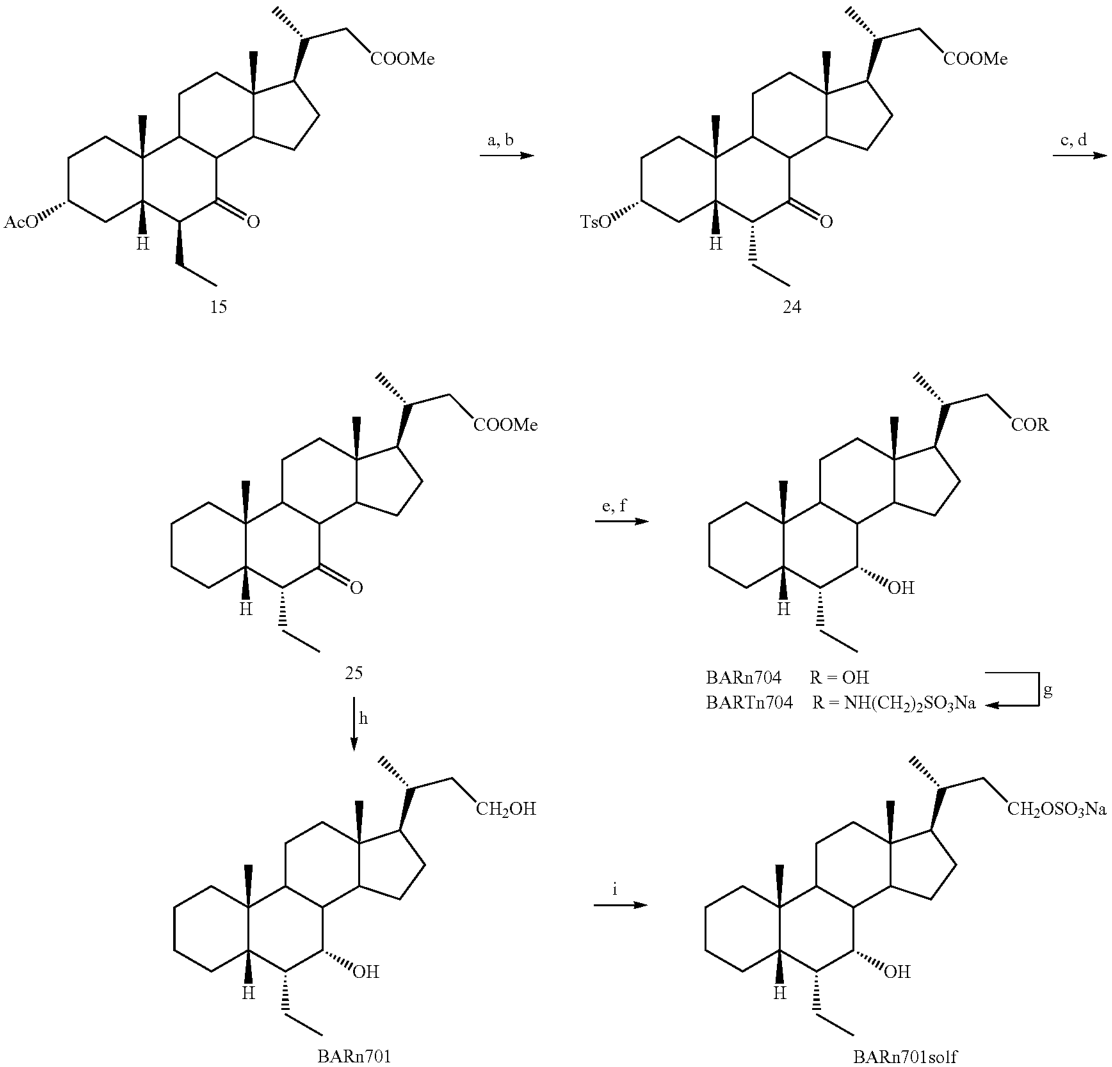

15

24

25

BARn704 R = OH

BARTn704 R = $NH(CH_2)_2SO_3Na$

BARn701

BARn701solf a) MeONa, MeOH; b) p-TsCl, pyridine, 73% over two steps; c) LiBr, $Li_2CO_3$, DMF, reflux, d) $H_2$, $Pd(OH)_2$, THF/MeOH 1:1, room temperature, quantitative yield over two steps; e) NaOH, MeOH:$H_2O$ 1:1 v/v, 80%; f) $LiBH_4$, MeOH dry, THF, 0° C., 92%; g) DMT-MM, $Et_3N$, taurine, DMF dry; h) $LiBH_4$, MeOH dry, THF, 0° C., 70%; i) $Et_3N•SO_3$, DMF, 95° C.

$H_3$-21), 0.89 (3H, s, $H_3$-19), 0.86 (3H, t, J=7.4 Hz, $H_3$-25), 0.70 (3H, s, $H_3$-18).

BARn701: $C_{25}H_{44}O_2$

The $^1H$ NMR was recorded on Varian Inova 400 MHz, using $CD_3OD$ as solvent: δ 3.66 (1H, br s, H-7), 3.61 (1H, m, H-23a), 3.54 (1H, m, H-23b), 0.96 (3H, d, J=6.7 Hz, $H_3$-21), 0.91 (3H, s, $H_3$-19), 0.89 (3H, t, J=7.3 Hz, $H_3$-25), 0.70 (3H, s, $H_3$-18).

The $^{13}C$ NMR was recorded on Varian Inova 100 MHz, using $CD_3OD$ as solvent: δ 71.5, 60.8, 57.8, 51.7, 48.6, 43.8, 43.3, 41.5, 41.1, 39.9, 39.2, 37.4, 34.5, 34.2, 29.4, 28.8, 25.0, 24.6 (2C), 23.5, 22.5, 22.0, 19.4, 12.2, 12.1.

BARn701solf: $C_{25}H_{43}NaO_5S$

The $^1H$ NMR was recorded on Varian Inova 400 MHz, using $CD_3OD$ as solvent: δ 4.02 (2H, m, $H_2$-23), 3.65 (1H, br s, H-7), 0.97 (3H, d, J=6.7 Hz, $H_3$-21), 0.91 (3H, s, $H_3$-19), 0.88 (3H, t, J=7.5 Hz, $H_3$-25), 0.70 (3H, s, $H_3$-18).

Example 21. Synthesis of 6α-ethyl-3β,7α-dihydroxy-24-nor-5β-cholan-23-oic acid (BARn710), 6α-ethyl-3β,7α-dihydroxy-24-nor-5β-cholan-23-oyl taurine sodium sulfate (BARTn710), 6α-ethyl-3β,7α-dihydroxy-24-nor-5β-cholan-23-ol (BARn706), and 6α-ethyl-3β,7α-dihydroxy-24-nor-5β-cholan-23-yl 23-sodium sulfate (BARn706solf)

d, J=6.0 Hz, $H_3$-21), 0.94 (3H, s, $H_3$-19), 0.91 (3H, t, J=7.3 Hz, $H_3$-25), 0.73 (3H, s, $H_3$-18).

The $^{13}C$ NMR was recorded on Varian Inova 100 MHz, using $CD_3OD$ as solvent: δ 177.7, 71.3, 67.4, 57.4, 51.8, 43.8 (2C), 42.8, 41.5, 41.2, 41.0, 37.0, 35.1, 33.8, 31.3, 31.2, 29.4, 28.3, 24.6, 24.2, 23.3, 22.2, 20.0, 12.2, 12.1.

BARTn710: $C_{27}H_{46}NNaO_6S$

The $^1H$ NMR was recorded on Varian Inova 400 MHz, using $CD_3OD$ as solvent: δ 3.97 (1H, br s, H-3), 3.66 (1H, br s, H-7), 3.59 (2H, t, J=6.8 Hz, $CH_2$—N), 2.96 (2H, t, J=6.8 Hz, $CH_2$—S), 2.42 (1H, dd, J=11.3, 3.3 Hz, H-22a), 1.00 (3H, d, J=6.3 Hz, $H_3$-21), 0.94 (3H, s, $H_3$-19), 0.90 (3H, t, J=7.0 Hz, $H_3$-25), 0.70 (3H, s, $H_3$-18).

BARn706: $C_{25}H_{44}O_3$

The $^1H$ NMR was recorded on Varian Inova 400 MHz, using $CD_3OD$ as solvent: δ 3.97 (1H, br s, H-3), 3.67 (1H, br s, H-7), 3.61 (1H, m, H-23a), 3.55 (1H, m, H-23b), 0.97 (3H, d, J=6.6 Hz, $H_3$-21), 0.95 (3H, s, $H_3$-19), 0.91 (3H, t, J=7.4 Hz, $H_3$-25), 0.71 (3H, s, $H_3$-18).

The $^{13}C$ NMR was recorded on Varian Inova 100 MHz, using $CD_3OD$ as solvent: δ 71.4, 67.4, 60.8, 57.9, 51.8, 43.8, 42.8, 41.5, 41.2, 41.1, 39.9, 37.0, 34.2, 33.8, 31.3, 31.2, 29.4, 28.3, 24.6, 24.2, 23.3, 22.3, 19.4, 12.2, 12.1.

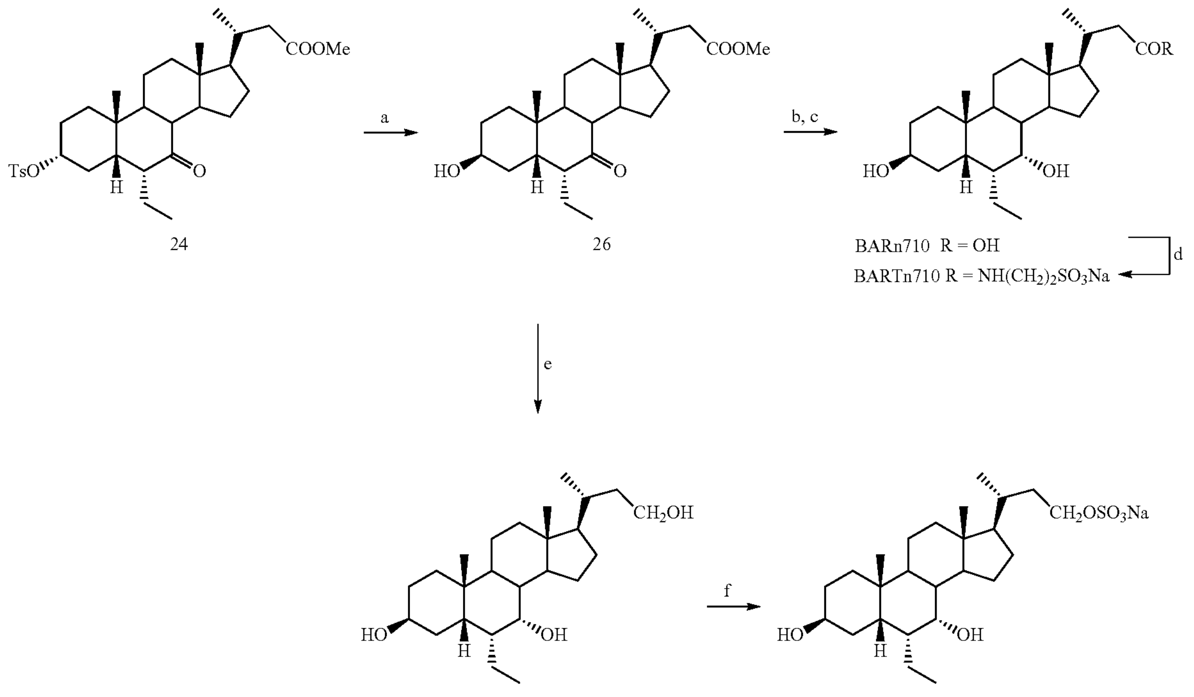

24

26

BARn710 R = OH

BARTn710 R = $NH(CH_2)_2SO_3Na$

BARn706

BARn706solf a) $CH_3COOK$, DMF:$H_2O$ 5:1 v/v; b) NaOH, MeOH:$H_2O$ 1:1 v/v; c) $LiBH_4$, MeOH dry, THF, 0° C., 58% over two steps; d)DMT—MM, $Et_3N$, taurine, DMF dry; e) $LiBH_4$, MeOH dry, THF, 0° C., 57%; f) $Et_3N$•$SO_3$, DMF, 95° C.

BARn710, BARTn710, BARn706 and BARn706solf were prepared starting from 24 and following the same synthetic protocol described for their C24 homologues (Example 2G, steps c-g).

BARn710: $C_{25}H_{42}O_4$

The $^1H$ NMR was recorded on Varian Inova 400 MHz, using $CD_3OD$ as solvent: δ 3.97 (1H, br s, H-3), 3.66 (1H, br s, H-7), 2.42 (1H, dd, J=11.3, 3.3 Hz, H-22a), 1.02 (3H, BARn706solf: $C_{25}H_{43}NaO_6S$ The $^1H$ NMR was recorded on Varian Inova 400 MHz, using $CD_3OD$ as solvent: δ 4.05 (2H, m, $H_2$-23), 3.97 (1H, br s, H-3), 3.66 (1H, br s, H-7), 1.00 (3H, d, J=6.0 Hz, $H_3$-21), 0.94 (3H, s, $H_3$-19), 0.91 (3H, t, J=6.9 Hz, $H_3$-25), 0.71 (3H, s, $H_3$-18).

Example 2J. Preparation of 6α-ethyl-3α, 7α-dihydroxy-25, 26-bishomo-5β-cholan-26-oic acid (BAR802), 6α-ethyl-3α, 7α-dihydroxy-25, 26-bishomo-5β-cholan-26-ol (BAR803), and 6α-ethyl-3α, 7α-dihydroxy-25, 26-bishomo-5β-cholan-26-yl-26-sodium sulfate (BAR804)

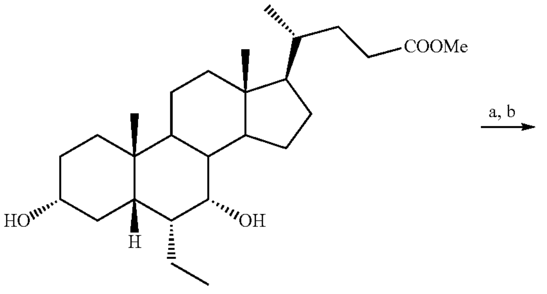

27

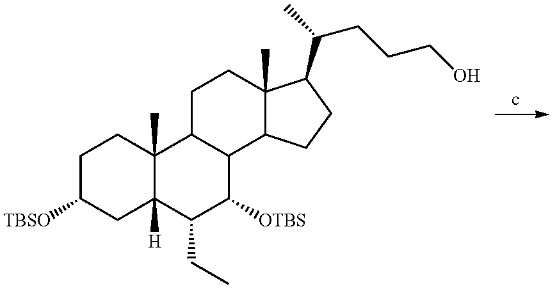

28

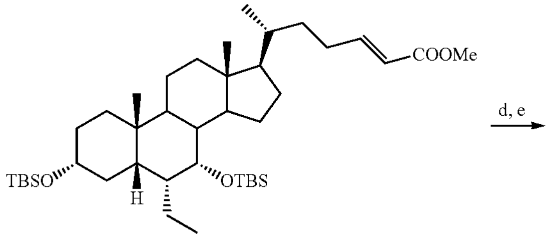

29

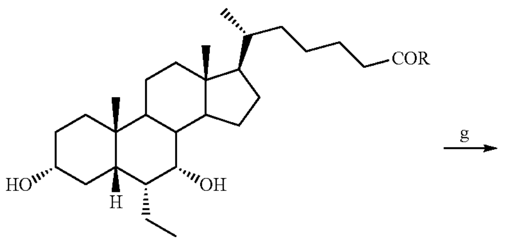

R = OMe 30 f
R = OH BAR802

-continued

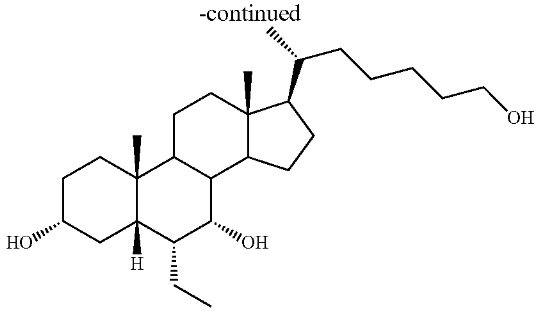

BAR803

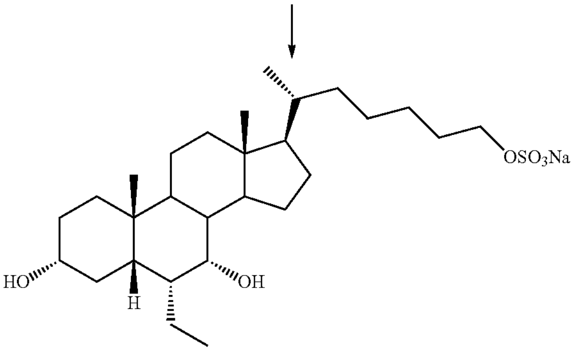

BAR804 a) 2,6-lutidine, t-butyldimethylsilyl trifluoromethanesulfonate, $CH_2Cl_2$, 0° C.; b) $LiBH_4$, MeOH dry, THF, 0° C., 68% over two steps; c) DMSO, oxalyl chloride, TEA dry, $CH_2Cl_2$, -78° C. then methyl(triphenylphosphoranylidene)acetate, 79%; d) $H_2$, $Pd(OH)_2/C$ Degussa type, THF/MeOH 1:1, quantitative yield; e) HCl 37%, MeOH, 87%; f) NaOH 5% in $MeOH/H_2O$ 1:1 v/v, 89%; g) $LiBH_4$, MeOH dry, THF, 0° C, 78%; h) $Et_3N•SO_3$, DMF, 95° C., 25%.

BAR802-804 were prepared following the same synthetic protocols as in Example 1A, steps a-g. Sulfation on a small aliquot of BAR803 in the same operative conditions of Example 1B step g afforded BAR804.

BAR802: $C_{28}H_{48}O_4$

The $^1H$ NMR was recorded on Varian Inova 400 MHz, using $CD_3OD$ as solvent: δ 3.66 (1H, br s, H-7), 3.31 (1H, m ovl, H-3), 2.24 (2H, t, J=7.3 Hz, $H_2$-25), 0.95 (3H, d, J=6.4 Hz, $H_3$-21), 0.92 (3H, s, $H_3$-19), 0.91 (3H, t, J=6.9 Hz, $H_3$-28), 0.70 (3H, s, $H_3$-18).

The $^{13}C$ NMR was recorded on Varian Inova 175 MHz, using $CD_3OD$ as solvent: δ 186.7, 73.3, 71.3, 57.7, 51.7, 47.0, 43.7, 43.1, 41.6, 41.1, 37.1, 36.9, 36.8, 36.6, 34.5, 34.4 (2C), 31.3, 29.4, 27.0 (2C), 24.6, 23.8, 23.5, 22.0, 19.2, 12.2, 12.0.

BAR803: $C_{28}H_{50}O_3$

The $^1H$ NMR was recorded on Varian Inova 400 MHz, using $CD_3OD$ as solvent: δ 3.64 (1H, br s, H-7), 3.53 (2H, t, J=6.6 Hz, $H_2$-26), 3.30 (1H, m ovl, H-3), 0.94 (3H, d, J=6.7 Hz, $H_3$-21), 0.91 (3H, s, $H_3$-19), 0.90 (3H, t, J=7.0 Hz, $H_3$-28), 0.68 (3H, s, $H_3$-18).

The $^{13}C$ NMR was recorded on Varian Inova 175 MHz, using $CD_3OD$ as solvent: δ 73.3, 71.3, 63.1, 57.7, 51.7, 47.0, 43.7, 43.1, 41.6, 41.1, 37.1, 36.8 (2C), 36.6, 34.5, 34.4, 33.7, 31.3, 29.5, 27.4, 27.0, 24.6, 23.8, 23.5, 22.0, 19.3, 12.3, 12.0.

BAR804: $C_{28}H_{49}NaO_6S$

The $^1H$ NMR was recorded on Varian Inova 400 MHz, using $CD_3OD$ as solvent: δ 3.99 (2H, t, J=6.6 Hz, $H_2$-26), 3.65 (1H, br s, H-7), 3.31 (1H, m ovl, H-3), 0.94 (3H, d, J=6.2 Hz, $H_3$-21), 0.91 (3H, s, $H_3$-19), 0.90 (3H, t, J=7.0 Hz, $H_3$-28), 0.69 (3H, s, $H_3$-18).

Biological Activities.

Activity of selected compounds was tested in vitro using a whole cell model transfected with a reporter genes to establish selectivity of compounds shown in table 1 toward FXR and TGR5/GPBAR1 in comparison with chenodeoxycholic acid (CDCA) and TLCA. CDCA is a primary bile acid that functions as an endogenous ligand for FXR, while TLCA is a physiological ligand for TGR5/GPBAR1. In this assay, HepG2 cells (a liver-derived cell line) were cultured at 37° C. in minimum essential medium with Earl's salts containing 10% fetal bovine serum (FBS), 1% L-glutamine, and 1% penicillin/streptomycin. HEK-293T cells were cultured at 37° C. in D-MEM containing 10% fetal bovine serum (FBS), 1% L-glutamine, and 1% penicillin/streptomycin. The transfection experiments were performed using Fugene HD according to manufactured specifications. Cells were plated in a 24-well plate at $5\times10^4$ cells/well. For FXR mediated transactivation, HepG2 cells were transfected with 100 ng of pSG5-FXR, 100 ng of pSG5-RXR, 100 ng of pGL4.70 a vector encoding the human *Renilla* gene and 250 ng of the reporter vector p(hsp27)-TK-LUC containing the FXR response element IR1 cloned from the promoter of heat shock protein 27 (hsp27).

For GPBAR1 mediated transactivation, HEK-293T cells were transfected with 200 ng of pGL4.29, a reporter vector containing a cAMP response element (CRE) that drives the transcription of the luciferase reporter gene luc2P, with 100 ng of pCMVSPORT6-human GPBAR1, and with 100 ng of pGL4.70 a vector encoding the human *Renilla* gene. In control experiments HEK-293T cells were transfected only with vectors pGL4.29 and pGL4.70 to exclude any possibility that compounds could activate the CRE in a GPBAR1 independent manner. At 24 h post-transfection, cells were stimulated for 18 h with 10 μM TLCA as a control agent or putative GPBAR1 agonists as the same concentration. After treatments, cells were lysed in 100 μL of lysis buffer (25 mM Tris-phosphate, pH 7.8; 2 mM DTT; 10% glycerol; 1% Triton X-100), and 20 μL of cellular lysate was assayed for luciferase activity using the luciferase assay system. Luminescence was measured using Glomax 20/20 luminometer. Luciferase activities were normalized against *Renilla* activities. Antagonism against FXR of GPBAR1/TGR5 was measured as percent of activity in transactivation assay suing activity of TLCA as example of agonism.

Animals and Protocols.

GPBAR1 null mice (GPBAR1-B6=GPBAR12/2 mice, generated directly into C57BL/6NCrl background), and congenic littermates on C57BL/6NCrl were housed under controlled temperatures (22° C.) and photoperiods (12:12-hour light/dark cycle), allowed unrestricted access to standard mouse chow and tap water and allowed to acclimate to these conditions for at least 5 days before inclusion in an experiment.

Scratching Test.

Male GPBAR1$^{-/-}$ mice and their congenic littermates (8-12 weeks of age) were used for this studies. The fur at the base of the neck was shaved, and mice were placed in individual cylinders on a glass shelf. A circumference of approx. 0.5 cm of diameter was drawn in the neck and test agents injected in this area. Mice were acclimatized to the experimental room, restraint apparatus and investigators for 2 h periods on 2 successive days before experiments. Scratching behavior was quantified by 2 observers unaware of tested agents or genotypes. A scratch was defined as lifting the hind limb to the injection site and then a placing of the paw on the floor, regardless of the number of strokes. If counts differed by greater than 5 scratches over a 30-minute period, both observers reevaluated the records. Results were expressed as the number of scratching events during 30 or 60 min of observation. Tested agents were: DCA (25 μg), TLCA (25 μg), UDCA (25 μg), and BAR502 (25 μg), or with betulinic acid (50 μg), oleanolic acid (50 μg). LCA and DCA were dissolved in DMSO and the other agents in 0.9% NaCl (10 μL). In another experimental setting GPBAR1$^{-/-}$ mice and their congenic littermates were administered alpha-naphthylisothiocyanate (ANIT) (25 mg/kg, per os) dissolved in olive oil or olive oil alone (control mice) or with the combination of ANIT plus BAR502 (15 mg/Kg once a day, per os) for 10 days. At day 5 spontaneous scratching was evaluated for 60 min and after subcutaneous injection of 25 μg DCA. Serum levels of total bilirubin, aspartate aminotransferase (AST) and alkaline phosphatase were measured by routine clinical chemistry testing performed on a Hitachi 717 automatic analyzer. For the estrogen model, wild type C57BL6 mice were administered 10 mg/Kg i.p. with 17α-Ethynylestradiol ($17\alpha E_2$) dissolved in PEG or PEG alone (control mice) or the combination of $17\alpha E_2$ and BAR502 (15 mg/Kg daily, per os) for 8 days. At the end of the study the spontaneous scratching and scratching induced by s.c. injection of 25 μg DCA was recorded. Gallbladder weight and serum levels of bilirubin and alkaline phosphatase were also measured. Throughout the studies animals were visually assessed at least twice a day from Monday to Friday and once a day over the week end by investigators and by highly trained animal facility personnel's including animal facility's veterinarian. Animals were weighted daily and sacrificed at indicated time points or when their clinical conditions become critical as assessed by a reduction of body weight higher than 25% of basal body weight in 7 days. In addition, animals were sacrificed when at the daily evaluation they demonstrate inability to rise or ambulate. Mice were euthanized by an overdose of sodium pentobarbital (>100 mg/kg i.p.).

The invention claimed is:

1. A method of treating FXR and/or TGR5/GPBAR1 mediated diseases, comprising administering an effective amount of a compound of formula (I)

(I)

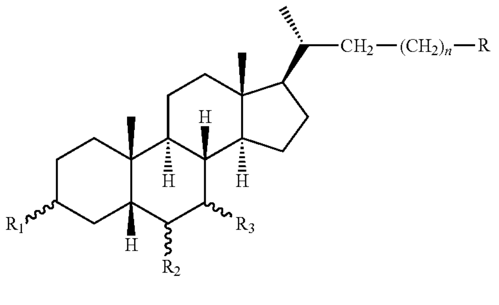

wherein $R_1$ is OH or H;

$R_2$ is Et or $=CH-CH_3$;

$R_3$ is OH or H;

n is 0, 1, or 3;

R is $CH_2OH$, COOH, or $CH_2OSO_3H$;

proviso that when $R_2$ is Et or $=CH-CH_3$ and $R_3$ is OH:

if n is 0 or 1, then R is $CH_2OH$ when $R_1$ is alpha-OH, or R is $CH_2OH$, $CH_2OSO_3H$ or COOH when $R_1$ is beta-OH or H;

if n is 3, then $R_1$ and R are as defined above;

or inorganic or organic pharmaceutically acceptable salts, solvates or amino acid conjugates thereof, wherein the FXR and/or TGR5/GPBAR1 mediated diseases are selected from the group consisting of chronic liver diseases, inflammatory bowel disease (IBD), Crohn's disease, ulcerative colitis and undetermined colitis, irritable bowel syndrome (IBS), bacterial overgrowth, acute and chronic pancreatitis, malabsorption, post-radiation colitis, and microscopic colitis, diabetic nephropathy, hypertensive nephropathy, acute and chronic kidney diseases, chronic tubulointerstitial diseases and vascular disorders of the kidney, atherosclerosis, dyslipidemia, hypercholesterolemia, hypertriglyceridemia, hypertension also known as arterial hypertension, inflammatory heart diseases, myocarditis, endocarditis, cardiopulmonary diseases, pulmonary artery hypertension, pulmonary fibrosis, insulin resistance, metabolic syndrome, Type I and Type II diabetes, hypoglycemia, obesity and conditions associated to bariatric surgery, liver cancer, bile duct cancers, pancreatic cancer, gastric cancer, colon-rectal cancer, breast cancer, human immunodeficiency associated disease (AIDS), Virus B infection, rheumatoid arthritis, systemic lupus erythematosus.

2. The method according to claim 1, wherein $R_2$ is Et or $=CH-CH_3$, $R_3$ is OH and if n is 0 or 1, then R is $CH_2OH$ when $R_1$ is alpha-OH, or R is $CH_2OH$, $CH_2OSO_3H$ or COOH when $R_1$ is beta-OH or H;

if n is 3, then $R_1$, $R_3$ and R are as defined in claim 1.

3. The method according to claim 1, said compound of formula (I) being selected in group consisting of

BAR501

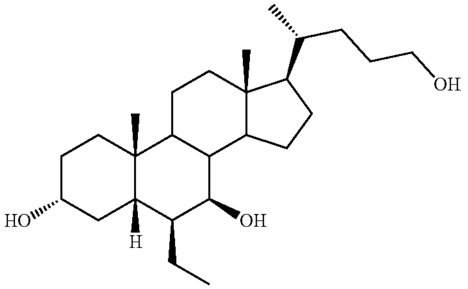

BARn501

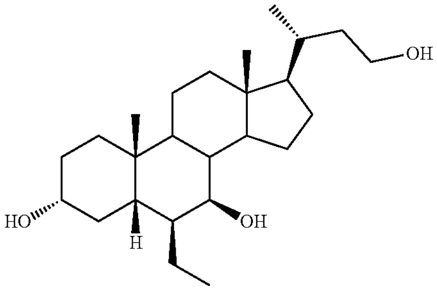

BAR501-6a

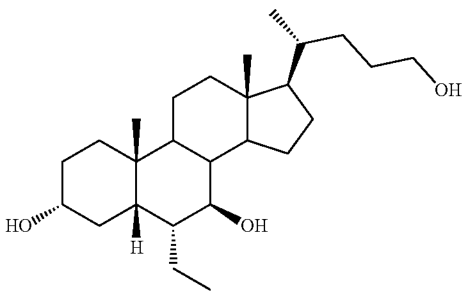

-continued

BAR502

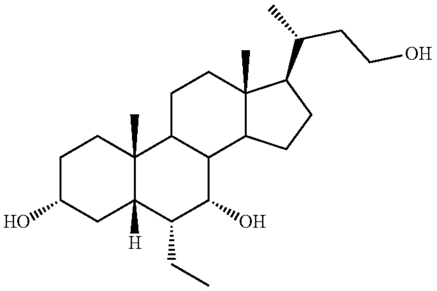

BAR503

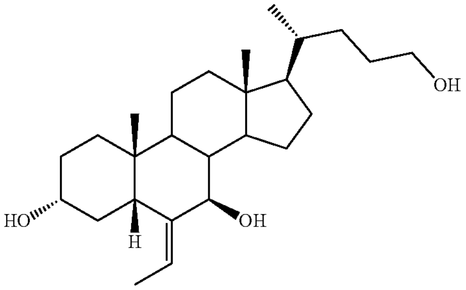

BAR504

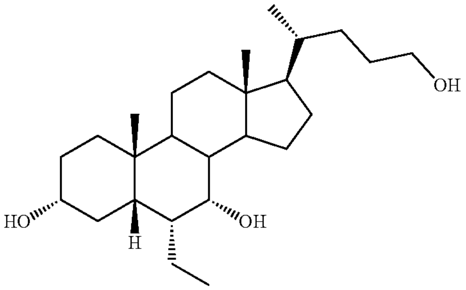

BAR504-6b

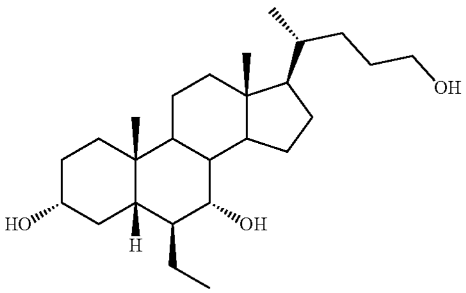

BAR701

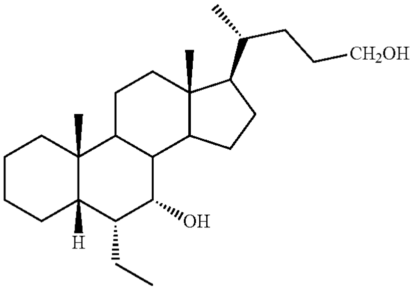

-continued
BAR701solf
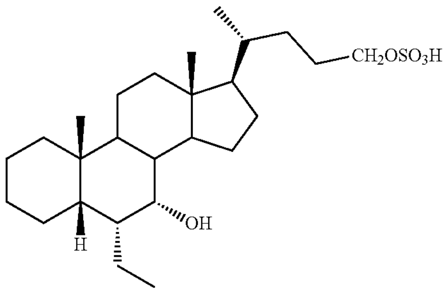
BARn701
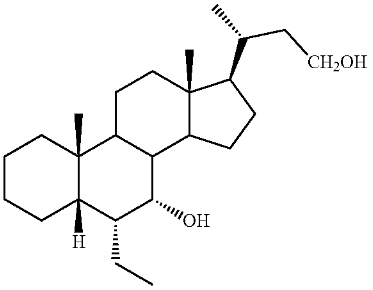
BAR702
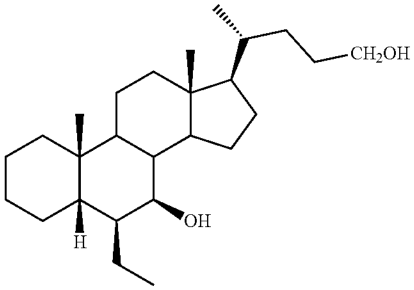
BAR703
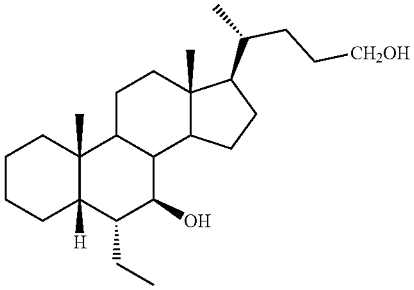
BAR704
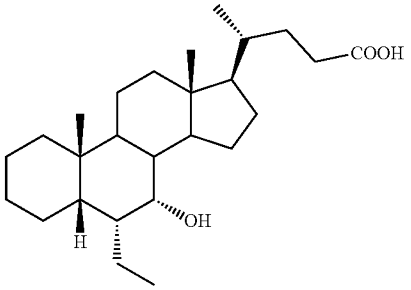
-continued
BARn704
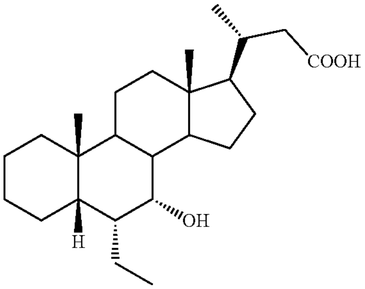
BAR705
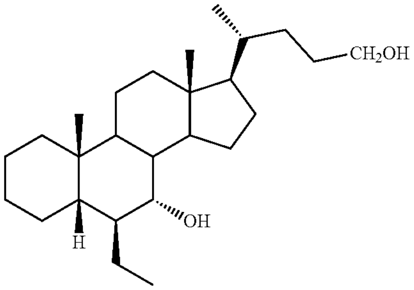
BAR706
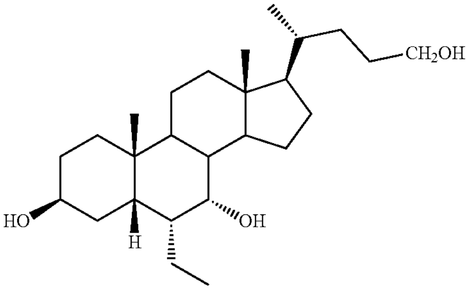
BARn706
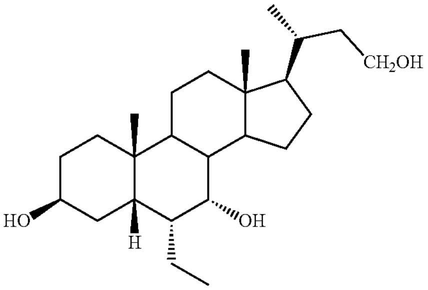
BARn706solf
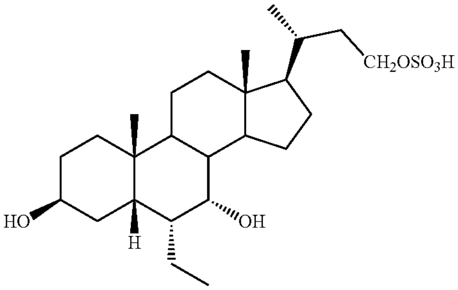

-continued
BAR707
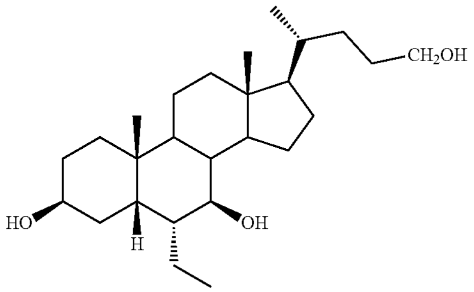
BAR708
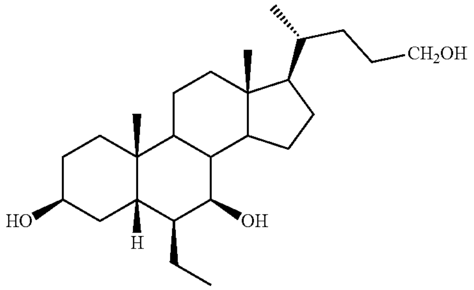
BAR709
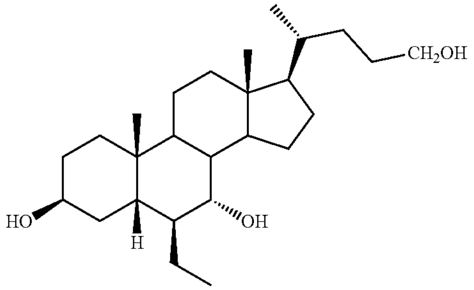
BAR710
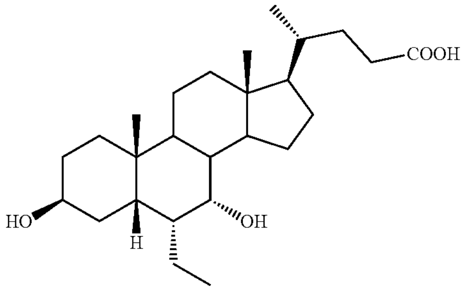
BARn710
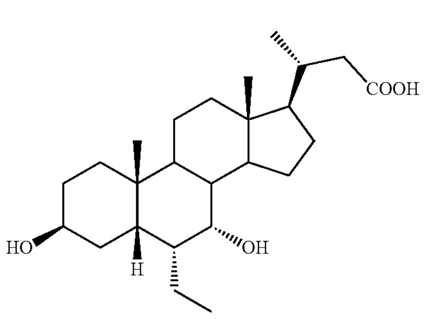
-continued
BAR711
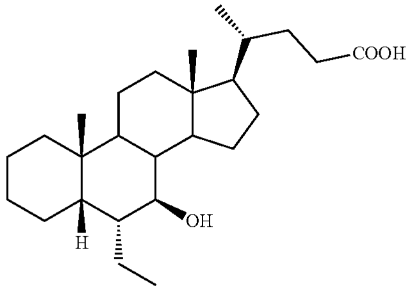
BAR712
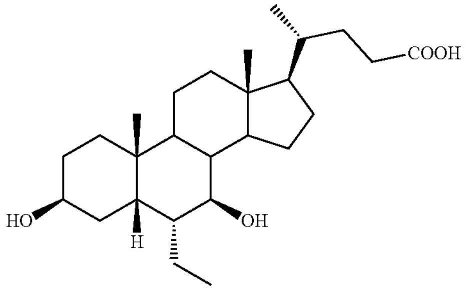
BAR802
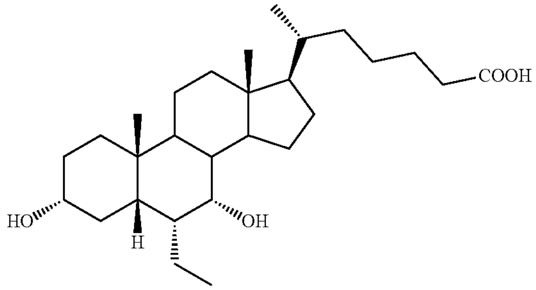
BAR803
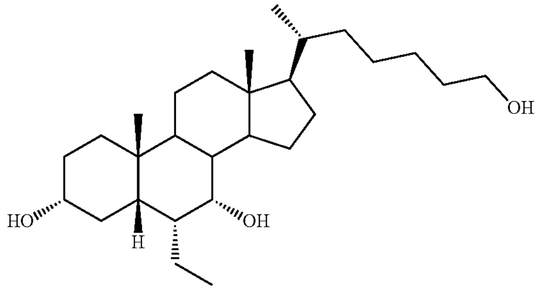
BAR804
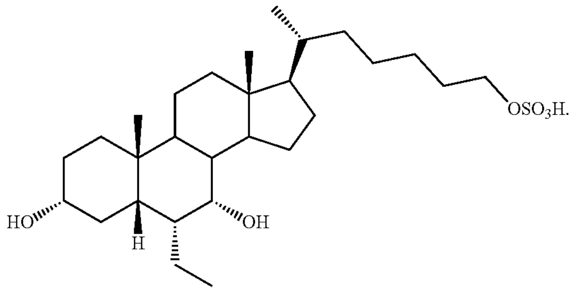

BAR106
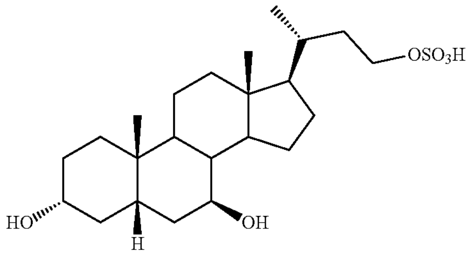
BAR107
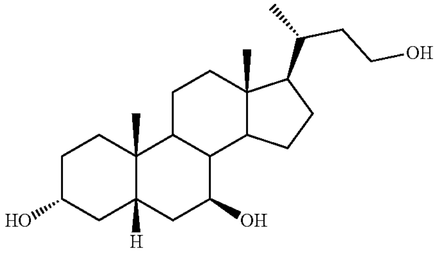
BAR304
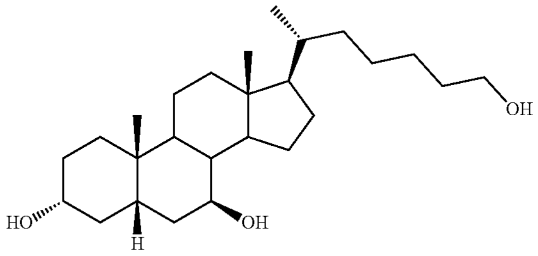
BAR305
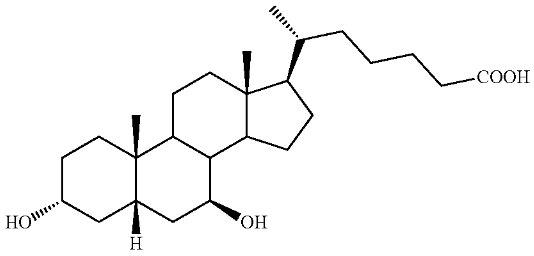
BAR402
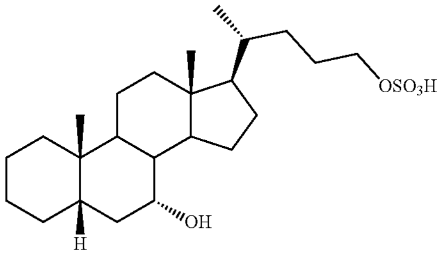
BARn406
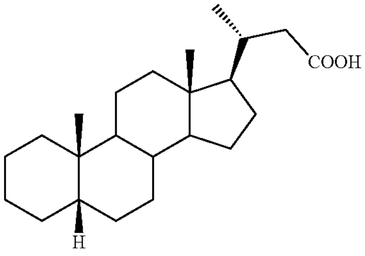
-continued
BAR407
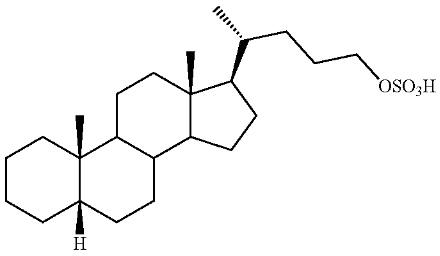
BAR501
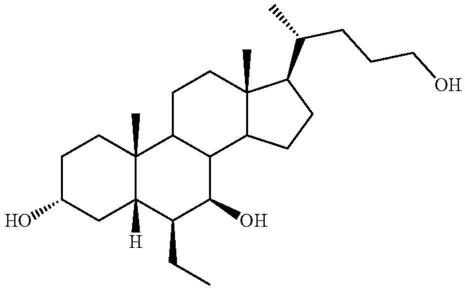
BARn501
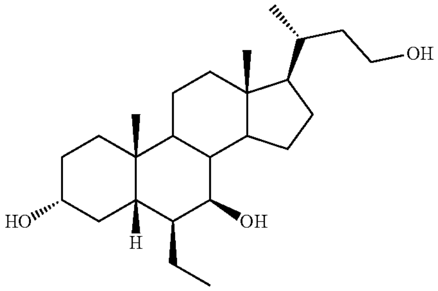
BAR501-6a
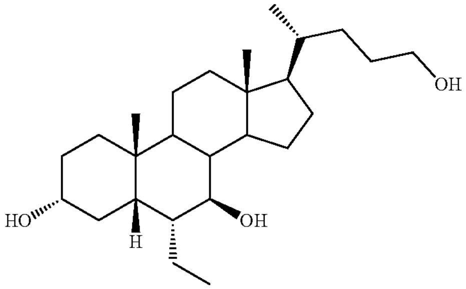
BAR502
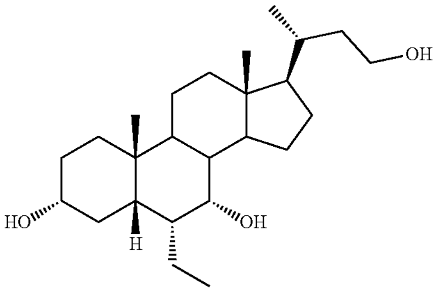

-continued
BAR503
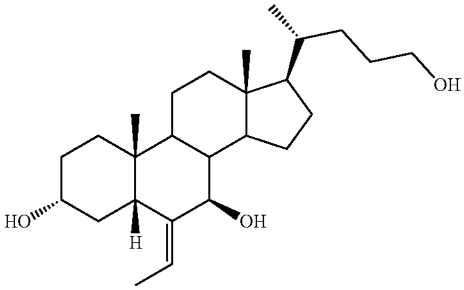
BAR504
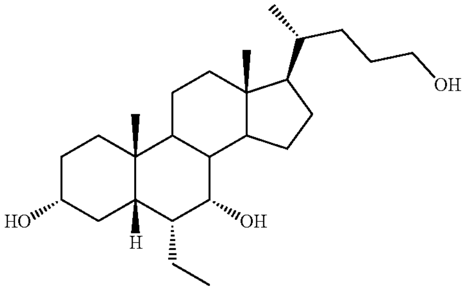
BAR504-6b
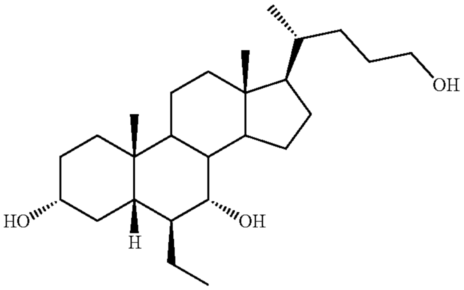
BAR506
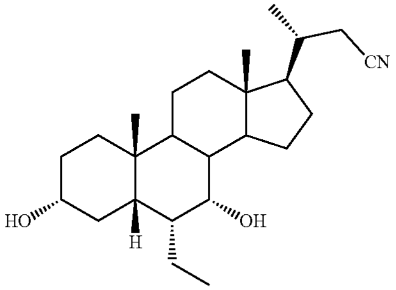
BAR701
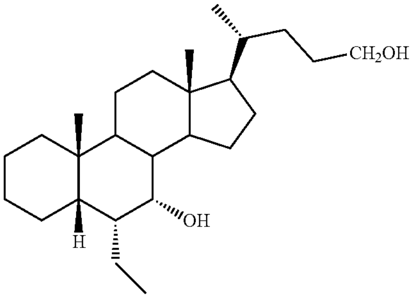
-continued
BAR701solf
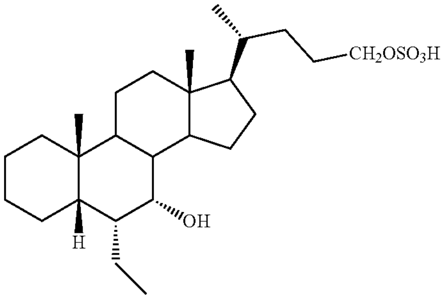
BARn701
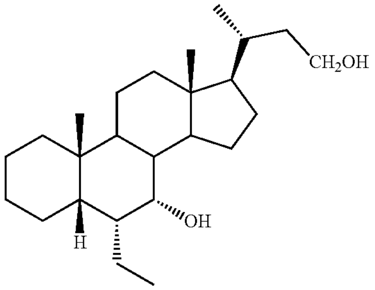
BAR702
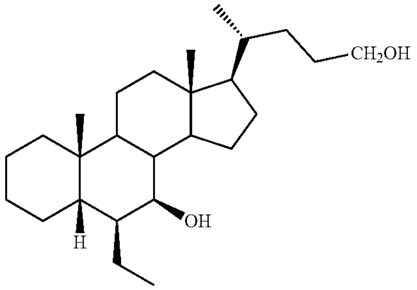
BAR703
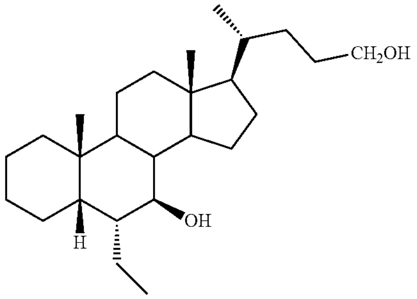
BAR704
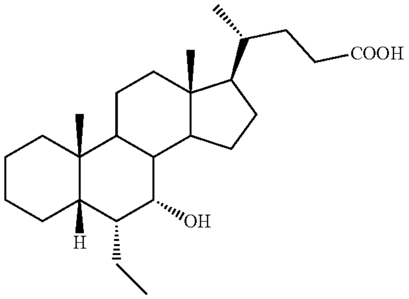

-continued
BARn704
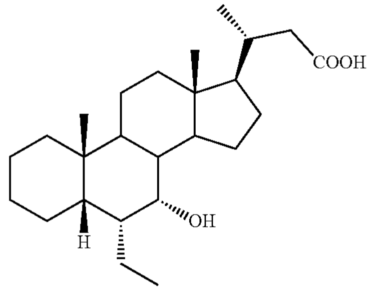
BAR705
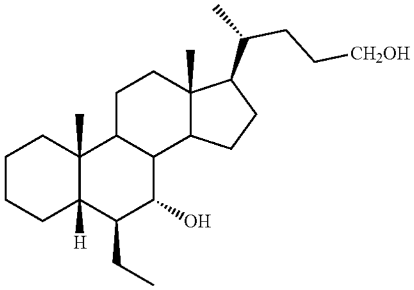
BAR706
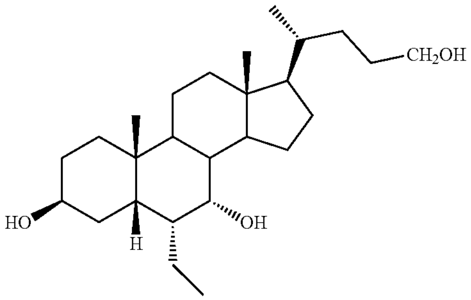
BARn706
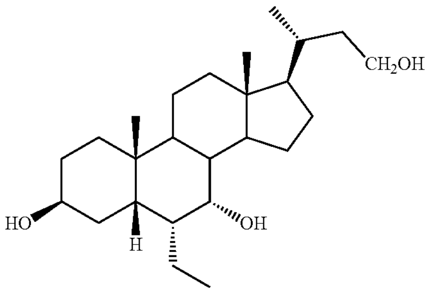
BARn706solf
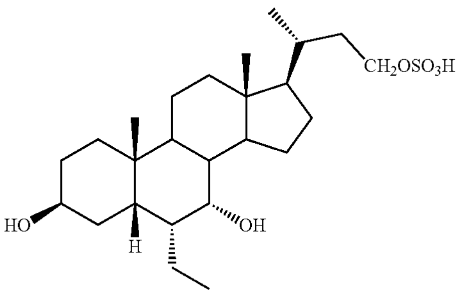
-continued
BAR707
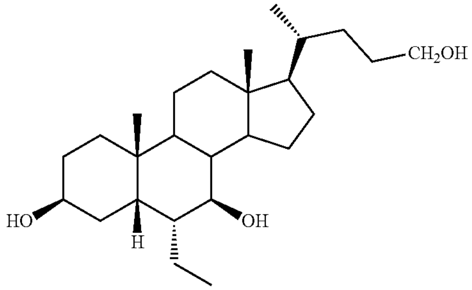
BAR708
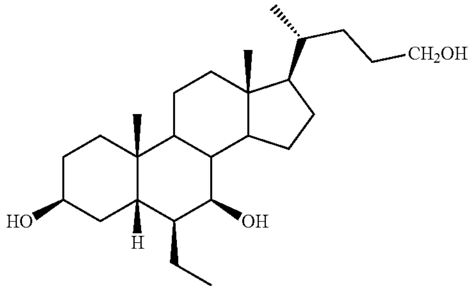
BAR709
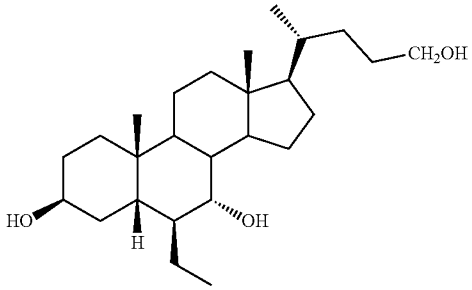
BAR710
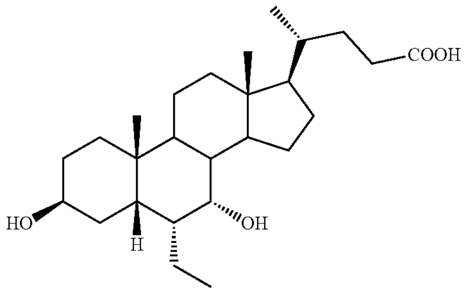
BARn710
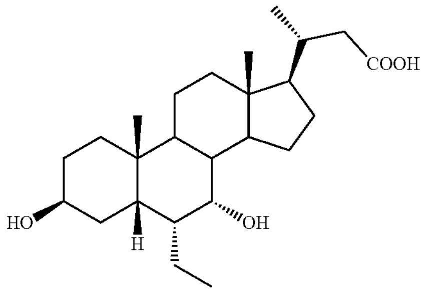

-continued

BAR711

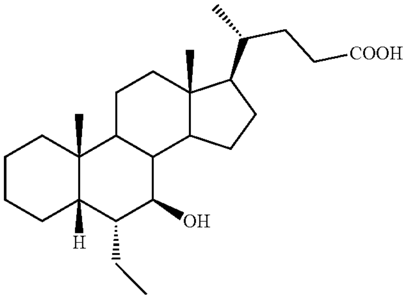

BAR712

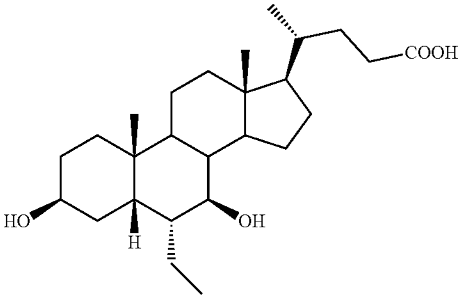

BAR802

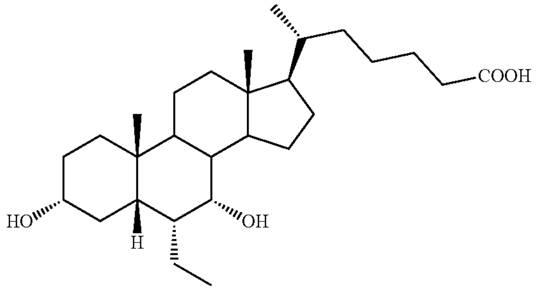

BAR803

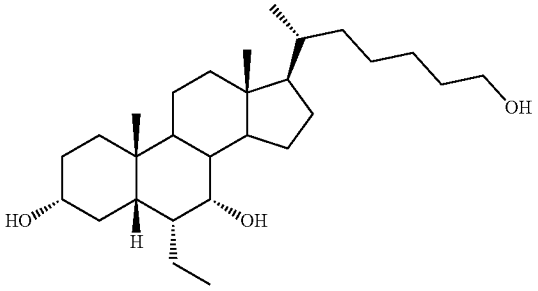

BAR804

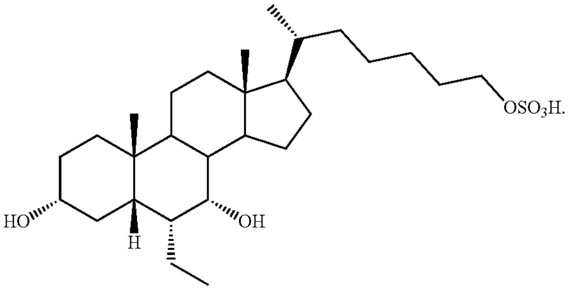

4. The method according to claim 1, wherein the diseases are chronic liver diseases selected from the group consisting of primary biliary cirrhosis (PBC), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), congenital hepatic fibrosis, granulomatous liver disease, intra- or extrahepatic malignancy, and Wilson's disease.

5. A method of treating FXR and/or TGR5/GPBAR1 mediated diseases, comprising administering an effective amount of a compound of formula (I)

(I)

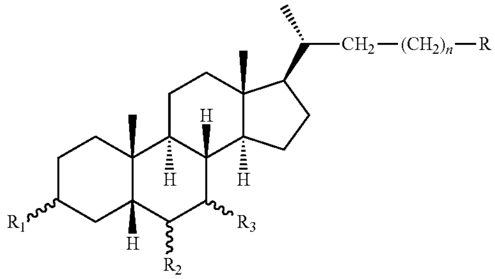

wherein $R_1$ is OH or H;

$R_2$ is Et or $=CH-CH_3$;

$R_3$ is OH or H;

n is 0, 1, or 3;

R is $CH_2OH$, COOH, or $CH_2OSO_3H$;

proviso that when $R_2$ is Et or $=CH-CH_3$ and $R_3$ is OH:

if n is 0 or 1, then R is $CH_2OH$ when $R_1$ is alpha-OH, or R is $CH_2OH$, $CH_2OSO_3H$ or COOH when $R_1$ is beta-OH or H;

if n is 3, then $R_1$ and R are as defined above;

or pharmaceutically acceptable salts thereof, wherein the FXR and/or TGR5/GPBAR1 mediated diseases are selected from the group consisting of chronic liver diseases, inflammatory bowel disease (IBD), Crohn's disease, ulcerative colitis and undetermined colitis, irritable bowel syndrome (IBS), bacterial overgrowth, acute and chronic pancreatitis, malabsorption, post-radiation colitis, and microscopic colitis, diabetic nephropathy, hypertensive nephropathy, acute and chronic kidney diseases, chronic tubulointerstitial diseases and vascular disorders of the kidney, atherosclerosis, dyslipidemia, hypercholesterolemia, hypertriglyceridemia, hypertension also known as arterial hypertension, inflammatory heart diseases, myocarditis, endocarditis, cardiopulmonary diseases, pulmonary artery hypertension, pulmonary fibrosis, insulin resistance, metabolic syndrome, Type I and Type II diabetes, hypoglycemia, obesity and conditions associated to bariatric surgery, liver cancer, bile duct cancers, pancreatic cancer, gastric cancer, colon-rectal cancer, breast cancer, human immunodeficiency associated disease (AIDS), Virus B infection, rheumatoid arthritis, systemic lupus erythematosus.

6. The method according to claim 5, wherein $R_2$ is Et or $=CH-CH_3$, $R_3$ is OH and if n is 0 or 1, then R is $CH_2OH$ when $R_1$ is alpha-OH, or R is $CH_2OH$, $CH_2OSO_3H$ or COOH when $R_1$ is beta-OH or H;

if n is 3, then $R_1$, $R_3$ and R are as defined in claim 5.

7. The method according to claim 5, said compound of formula (I) being selected in group consisting of
BAR501
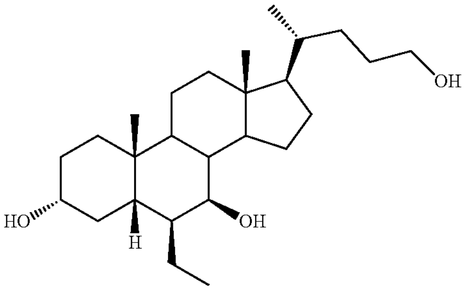
BARn501
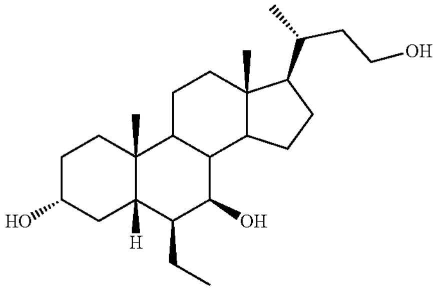
BAR501-6a
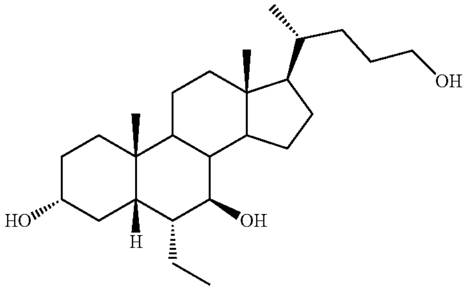
BAR502
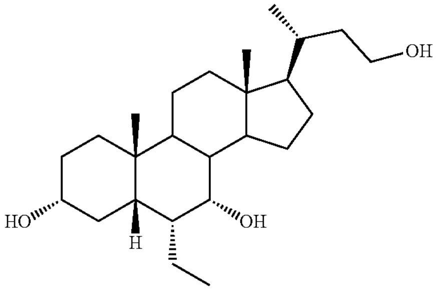
BAR503
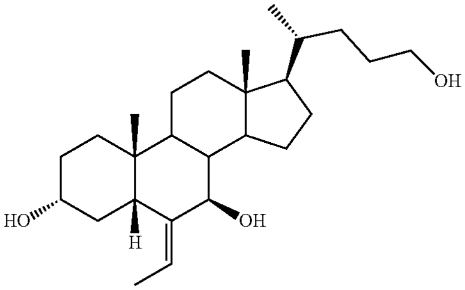
-continued
BAR504
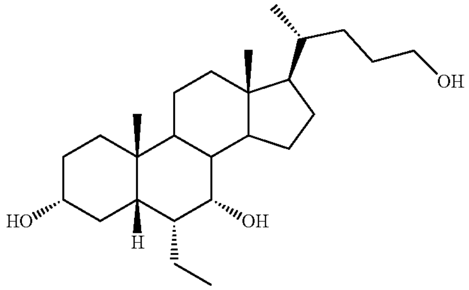
BAR504-6b
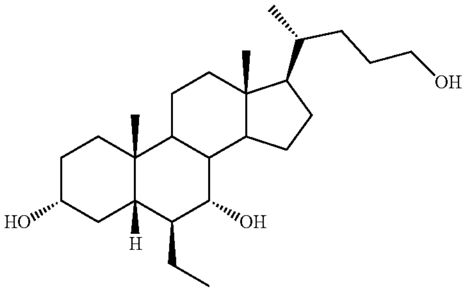
BAR701
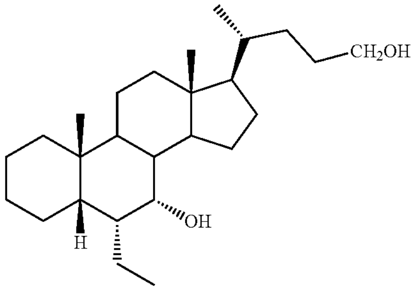
BAR701solf
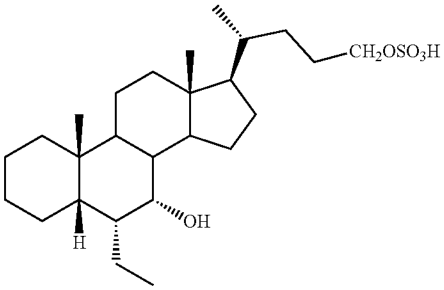
BARn701
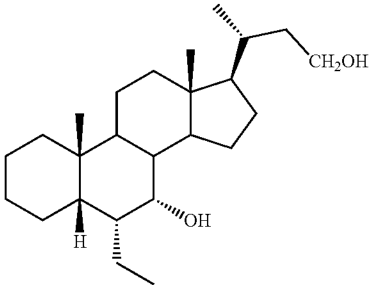

-continued
BAR702
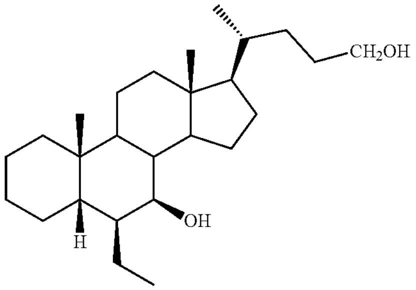
BAR703
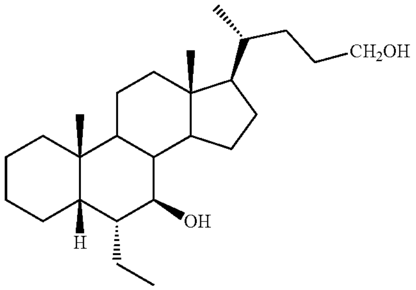
BAR704
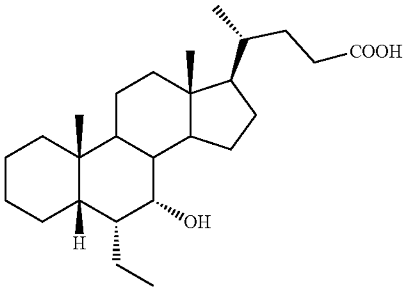
BARn704
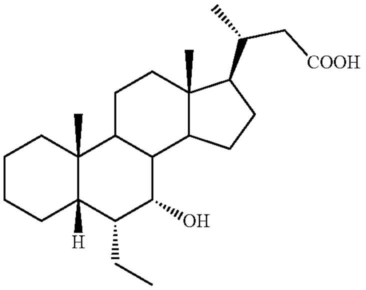
BAR705
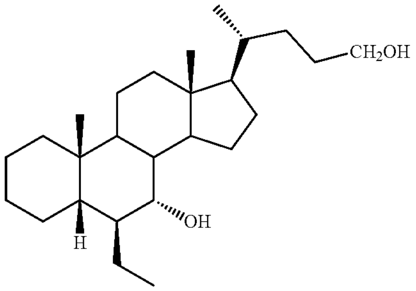
-continued
BAR706
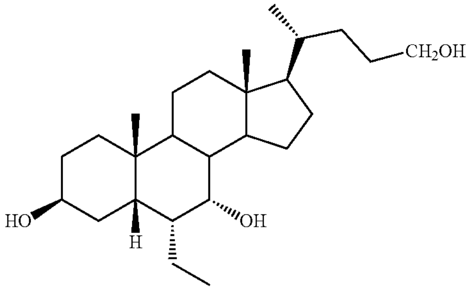
BARn706
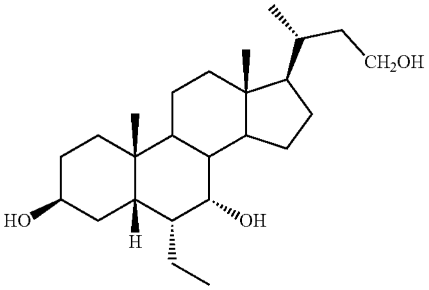
BARn706solf
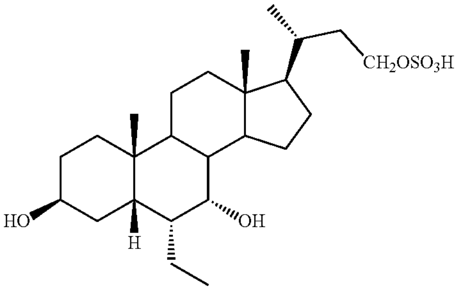
BAR707
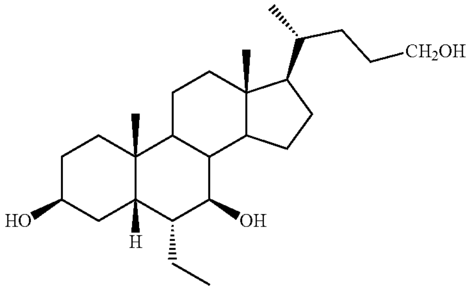
BAR708
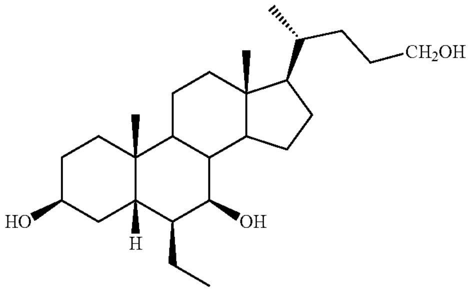

-continued

BAR709

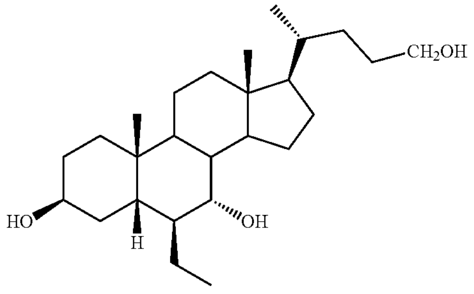

BAR710

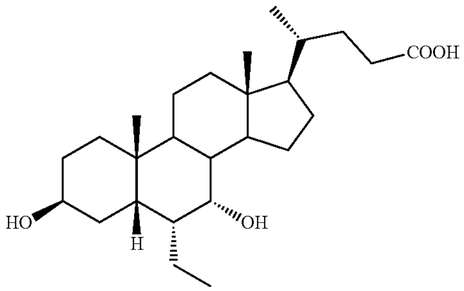

BARn710

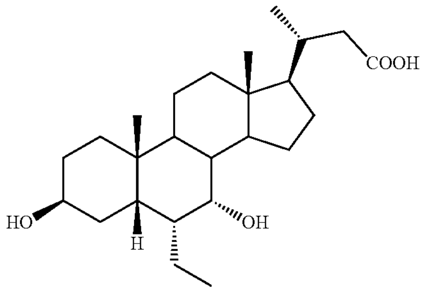

BAR711

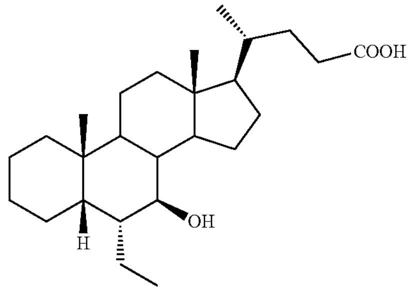

BAR712

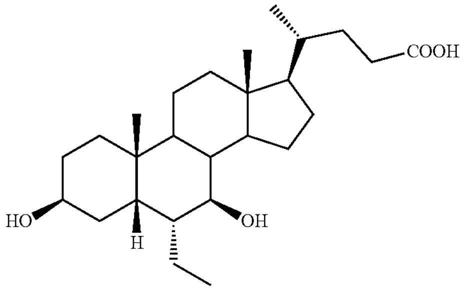

-continued

BAR802

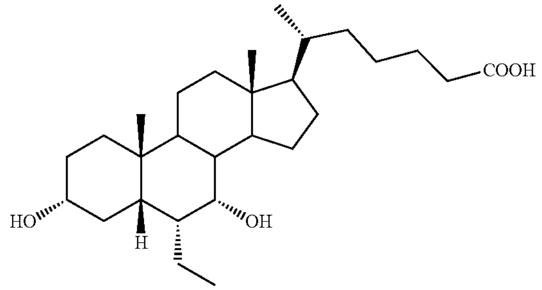

BAR803

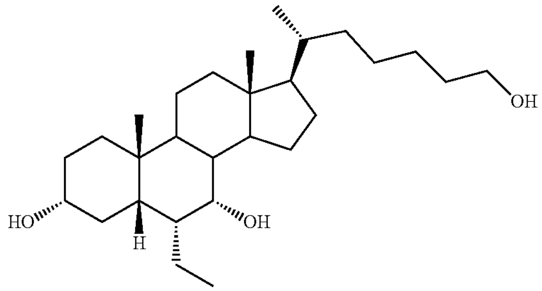

BAR804

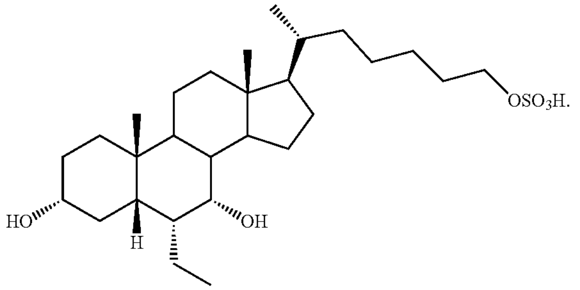

8. The method according to claim 5, wherein the diseases are chronic liver diseases selected from the group consisting of primary biliary cirrhosis (PBC), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), congenital hepatic fibrosis, granulomatous liver disease, intra- or extrahepatic malignancy, and Wilson's disease.

9. The method according to claim 7, wherein the diseases are chronic liver diseases selected from the group consisting of primary biliary cirrhosis (PBC), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), congenital hepatic fibrosis, granulomatous liver disease, intra- or extrahepatic malignancy, and Wilson's disease.

10. The method according to claim 3, wherein the diseases are chronic liver diseases selected from the group consisting of primary biliary cirrhosis (PBC), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), congenital hepatic fibrosis, granulomatous liver disease, intra- or extrahepatic malignancy, and Wilson's disease.

11. A method of treating FXR and/or TGR5/GPBAR1 mediated diseases, comprising administering an effective amount of a compound, wherein the compound is:

BAR502

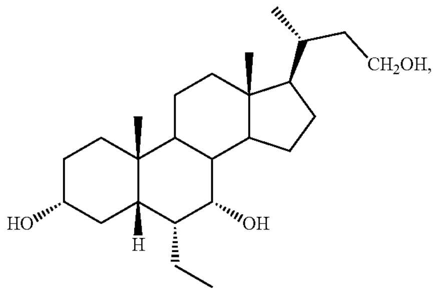

or pharmaceutically acceptable salts thereof, wherein the FXR and/or TGR5/GPBAR1 mediated diseases are selected from the group consisting of primary biliary cirrhosis (PBC), primary sclerosing cholangitis (PSC), drug induced cholestasis, intrahepatic cholestasis of pregnancy, parenteral nutrition associated cholestasis, bacterial overgrowth and sepsis associated cholestasis, autoimmune hepatitis, chronic viral hepatitis, alcoholic liver disease, nonalcoholic fatty liver disease (NAFLD), nonalcoholic steatohepatitis (NASH), congenital hepatic fibrosis, granulomatous liver disease, intra- or extrahepatic malignancy, Wilson's disease, acute and chronic kidney diseases, chronic tubulointerstitial diseases and vascular disorders of the kidney, atherosclerosis, dyslipidemia, hypercholesterolemia, hypertriglyceridemia, hypertension also known as arterial hypertension, inflammatory heart diseases, myocarditis, endocarditis, insulin resistance, metabolic syndrome, Type I and Type II diabetes, hypoglycemia, and obesity and conditions associated to bariatric surgery.

* * * * *

UNITED STATES PATENT AND TRADEMARK OFFICE
CERTIFICATE OF CORRECTION

PATENT NO. : 10,407,462 B2  
APPLICATION NO. : 15/314771  
DATED : September 10, 2019  
INVENTOR(S) : Angela Zampella et al.

It is certified that error appears in the above-identified patent and that said Letters Patent is hereby corrected as shown below:

In the Claims

In Claim 3, please delete all the 36 compounds (from Compound BAR106 to Compound BAR804) listed from Column 69, Line 1 to Column 75, Line 64.

Signed and Sealed this  
Seventeenth Day of December, 2019

Andrei Iancu  
*Director of the United States Patent and Trademark Office*